Figure 1:
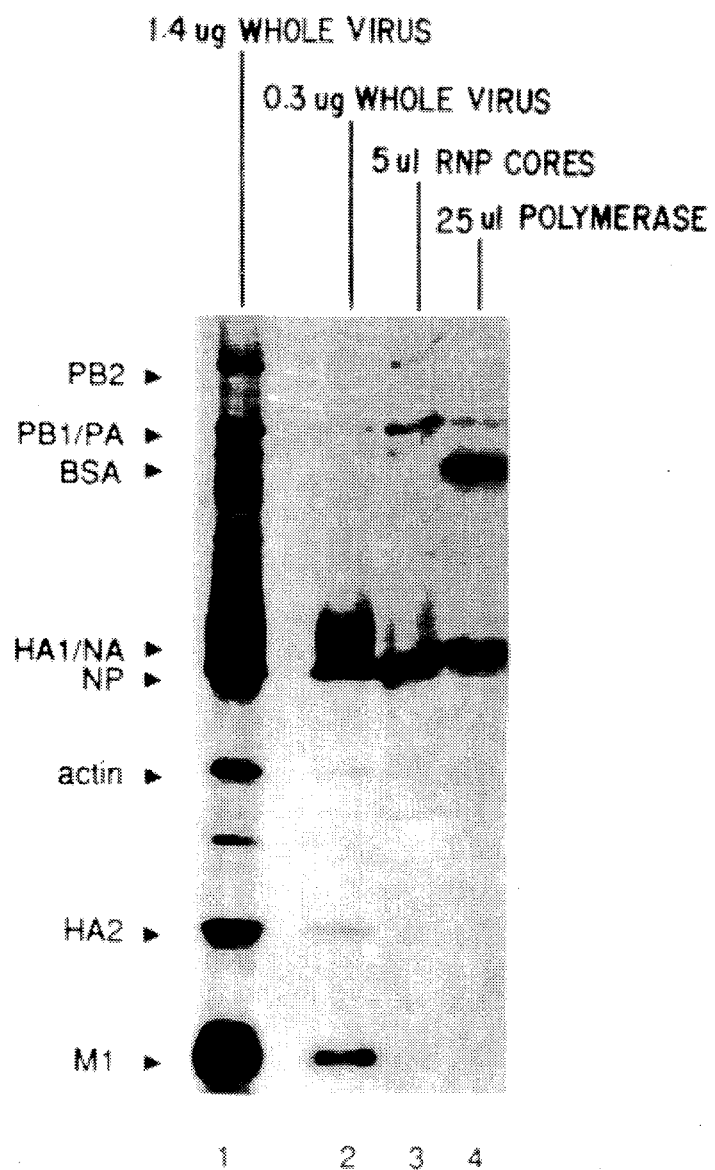

United States Patent [19]
Palese et al.

[11] Patent Number: 5,578,473
[45] Date of Patent: *Nov. 26, 1996

[54] RECOMBINANT NEGATIVE STRAND RNA VIRUS

[75] Inventors: Peter Palese, Leonia, N.J.; Jeffrey D. Parvin, Belmont, Mass.; Mark Krystal, Leonia, N.J.

[73] Assignee: Aviron, Inc., Mountain View, Calif.

[ * ] Notice: The portion of the term of this patent subsequent to Nov. 24, 2009, has been disclaimed.

[21] Appl. No.: 209,178

[22] Filed: Mar. 10, 1994

Related U.S. Application Data

[62] Division of Ser. No. 190,698, Feb. 1, 1994, abandoned, which is a continuation of Ser. No. 925,061, Aug. 4, 1992, abandoned, which is a division of Ser. No. 527,237, May 22, 1990, Pat. No. 5,166,057, which is a continuation-in-part of Ser. No. 440,053, Nov. 21, 1989, abandoned, which is a continuation-in-part of Ser. No. 399,728, Aug. 28, 1989, abandoned.

[51] Int. Cl.⁶ ............................ C12N 15/09; C12N 7/01; C12N 7/02; C12N 7/04
[52] U.S. Cl. .................................. 435/172.3; 435/235.1; 435/320.1; 435/236; 935/32
[58] Field of Search ............................ 435/172.3, 235.1, 435/320.1, 236, 172.1; 935/32, 65; 536/23.72, 24.1

[56] References Cited

U.S. PATENT DOCUMENTS

| | | | |
|---|---|---|---|
| 4,786,600 | 11/1988 | Kramer et al. | 435/320.1 |
| 5,166,057 | 11/1992 | Palese et al. | 435/69.1 |

OTHER PUBLICATIONS

Tyler, K. L. et al. 1991, *Fundamental Virology*, 2nd Ed., B. N. Fields et al, Raven Press, N.Y., pp. 191–239.
Westrop, G. D. et al. 1987, *In The Molecular Biology of the Positive Strand RNA Viruses*, Academic Press, London, pp. 53–60.
Lustig, S. et al., 1988, *J. Virol.* vol. 62 pp. 2329–2336.
Kinney, R. M. et al. 1989, *Virology* vol. 170 pp. 19–30.
Emerson and Yu, 1975, "Both NS and L Proteins Are Required for In Vitro RNA Synthesis by Vesicular Stomatitis Virus", J. Virol. 15: 1348–1356.
Naito and Ishihama, 1976, "Function and Structure of RNA Polymerase from Vesicular Stomatitis Virus", J. Biol. Chem. 251: 4307–4314.
Hay et al., 1977, "Transcription of the Influenza Virus Genome", Virol. 83: 337–355.
Racaniello et al., 1981, "Cloned Poliovirus Complementary DNA Is Infectious in Mammalian Cells", Science 214: 916–919.
Lamb and Choppin, 1983, "The Gene Structure and Replication of Influenza Virus", Ann. Rev. Biochem 52: 467–506.
Krug, Transcription and Replication of Influenza Viruses. In: Genetics of Influenza Viruses, Ed., Palese, P. and Kingsbury, D. W. New York, Springer–Verlag, 1983, pp. 70–98.

Dreher et al., 1984, "Mutant Viral RNAs Synthesized In Vitro Show Altered Aminoacylation and Replicase Template Activities", Nature 311: 171–175.
Dreher et al., 1988, "Mutational Analysis of the Sequence and Structural Requirements in Brome Mosaic Virus RNA for Minus Strand Promoter Activity", J. Mol. Biol. 201: 31–40.
Kaplan et al., 1985, "In Vitro Synthesis of Infectious Poliovirus RNA", Proc. Natl. Acad. Sci. USA. 82: 8424–8428.
Kato et al., 1985, "Purification and Enzymatic Properties of an RNA Polymerase–RNA Complex from Influenza Virus", Virus Research 3: 115–127.
De and Banerjee, 1985, "Requirements and Functions of Vesicular Stomatitis Virus L and NS Proteins in the Transcription Process In Vitro", Biochem. Biophys. Res. Commun. 126: 40–49.
Beaton and Krug, 1986, "Transcription Antitermination During Influenza Viral Template RNA Synthesis Requires the Nucleocapsid Protein and the Absence of a 5' Capped End", Proc. Natl. Acad. Sci. USA. 83: 6282–6286.
Levis et al., 1986, "Deletion Mapping of Sindbis Virus DI RNAs Derived from a cDNAs Defines the Sequences Essential for Replication and Packaging", Cell 44: 137–145.
Takeuchi et al., 1987, "In Vitro Synthesis of Influenza Viral RNA: Characterization of an Isolated Nuclear System That Supports Transcription of Influenza Viral RNA", J. Biochem. 101:837–845.
Hsu et al., 1987, "Genomic RNAs of Influenza Viruses Are Held in a Circular Conformation In Virions and In Infected Cells by a Terminal Panhandle", Proc. Natl. Acad. Sci. USA. 84: 8140–8144.
Honda et al., "Identification of the RNA Polymerase–Binding Site on Genome RNA of Influenza Virus", J. Biochem. 102: 1241–1249.

(List continued on next page.)

*Primary Examiner*—Mary E. Mosher
*Attorney, Agent, or Firm*—Pennie & Edmonds

[57] ABSTRACT

Recombinant negative strand virus RNA templates which may be used to express heterologous gene products and/or to construct chimeric viruses are described. Influenza viral polymerase, which was prepared depleted of viral RNA, was used to copy small RNA templates prepared from plasmid-encoded sequences. Template constructions containing only the 3' end of genomic RNA were shown to be efficiently copied, indicative that the promoter lay solely within the 15 nucleotide 3' terminus. Sequences not specific for the influenza vital termini were not copied, and, surprisingly, RNAs containing termini identical to those from plus sense cRNA were copied at low levels. The specificity for recognition of the virus-sense promoter was further defined by site-specific mutagenesis. It was also found that increased levels of vital protein were required in order to catalyze both the cap-endonuclease primed and primer-free RNA synthesis from these model templates as well as from genomic length RNAs. This indicated that this reconstituted system had catalytic properties very smilar to those of native viral RNPs. High levels of expression of a heterologous gene was obtained using the constructs and methods described.

11 Claims, 20 Drawing Sheets

OTHER PUBLICATIONS

Ward et al., 1988, "Direct Measurement of the Poliovirus RNA Polymerase Error Frequency In Vitro", J. Virol. 62: 558–562.

Mirakhur and Peluso, 1988, "In Vitro Assembly of a Functional Nucleocapsid from the Negative–Stranded Genome RNA of a Defective Interfering Particle of Vesicular Stomatitis Virus", Proc. Natl. Acad. Sci. USA. 85: 7511–7515.

Ishihama and Nagata, 1988, "Viral RNA Polymerases", CRC Crlt. Rev. Biochem. 23: 27–76.

Shapiro and Krug, 1988, "Influenza Virus RNA Replication In Vitro: Synthesis of Viral Template RNAs and Virion RNAs in the Absence of an Added Primer", J. Virol. 62: 2285–2290.

Honda et al., 1988, "RNA Polymerase of Influenza Virus: Role of NP in RNA Chain Elongation", J. Biochem. 104: 1021–1026.

Szewczyk et al., 1988, "Modification, Thioredoxin Renaturation, and Reconstituted Activity of the Three Subunits of the Influenza A Virus RNA Polymerase", Proc. Natl. Acad. Sci. USA 85: 7907–7911.

Palese, 1977, "The Genes of Influenza Virus", Cell, 10: 1–10.

Bishop et al., 1971, "Transcription of the Influenza Ribonucleic Acid Genome by a Virion Polymerase", J. Virol. 8: 66–73.

Bouloy et al., 1980, "Both the 7–methyl and the 2'–O–methyl Groups in the Cap of mRNA Strongly Influence its Ability to Act as Primer for Influenza Virus RNA Transcription", Proc. Natl. Acad. Sci. USA. 77: 3952–3956.

Ulmanen et al., 1983, "Influenza Virus Temperature–Sensitive Cap ($m^7$GpppNm)–Dependent Endonuclease", J. Virol. 45: 27–35.

Beaton and Krug, 1984, "Synthesis of the Templates for Influenza Virion RNA Replication In Vitro", Proc. Natl. Acad. Sci. USA. 81: 4682–4686.

Kawakami et al., 1981, "RNA Polymerase of Influenza Virus. II. Influence of Oligonucleotide Chain Length on the Priming Activity of RNA Synthesis", J. Biochem. 89: 1759–1768.

Kawakami and Ishihama, 1983, "RNA Polymerase of Influenza Virus. III. Isolation of RNA Polymerase–RNA Complexes from Influenza Virus PR8", J. Biochem. 93: 989–996.

Detjen et al., 1987, "The Three Influenza Virus Polymerase (P) Proteins Not Associated with Viral Nucleocapsids in the Infected Cell Are in the Form of a Complex", J. Virol. 61: 16–22.

St. Angelo et al., 1987, "Two of the Three Influenza Viral Polymerase Proteins Expressed by Using Baculovirus Vectors Form a Complex in Insect Cells", J. Virol. 61: 361–365.

Khan et al., 1987, "Synthetic Templates and the RNA Polymerase of Influenza A Virus", Nucleosides & Nucleosides 6: 543–554.

Krystal et al., 1986, "Expression of the Three Influenza Virus Polymerase Proteins in a Single Cell Allows Growth Complementation of Viral Mutants", Proc. Natl. Acad. Sci. USA. 83: 2709–2713.

Li et al., 1989, "Complementation and Analysis of an NP Mutant of Influenza Virus", Virus Research, 12: 97–112.

Kingsbury, et al., 1987, "Assembly of Influenza Ribonucleoprotein In Vitro Using Recombinant Nucleoprotein", Virol. 156: 396–403.

Rochovansky, 1976, "RNA Synthesis by Ribonucleoprotein––Polymerase Complexes Isolated from Influenza Virus", Virol. 73: 327–338.

Robertson et al., 1981, "Polyadenylation Sites for Influenza Virus mRNA", J. Virol. 38: 157–163.

Schreirer et al., 1988, "Functional and Structural Analysis of the Ribonucleoprotein Complexes of Different Human Influenza Virus Strains", Acta. Virol. 32: 289–295.

Xiong et al., 1989, "Sindbis Virus: An Efficient, Broad Host Range Vector for Gene Expression in Animal Cells", Science, 243: 1188–1191.

Parvin et al., 1989, "Promoter Analysis of Influenza Virus RNA Polymerase", J. Virol. 63: 5142–5152.

Luytjes et al., 1989, "Amplification, Expression, and Packaging of a Foreign Gene by Influenza Virus", Cell 59: 1107–1113.

Enami et al., 1990, "Introduction of Site–Specific Mutations Into The Genome of Influenza Virus", Proc. Natl. Acad. Sci. 87: 3802–3805.

Ballart et al., 1990, "Infectious Measles Virus from Cloned cDNA", EMBO J. 9: 379–384; and its retraction at 8th International Conference on Negative Strand Viruses, 1991, Abstr. 43.

Huang et al., 1990, "Determination of Influenza Virus Proteins Required for Genome Replication", J. Virol. 64: 5669–5673.

Ballart, 1991, "Functional and Nonfunctional Measles Virus Matrix Genes from Lethal Human Brain Infections", J. Virol. 65: 3161–3166; and its retraction attached.

Enami & Palese, 1991, "High–Efficiency Formation of Influenza Virus Transfectants", J. Virol. 65(5): 2711–2713.

Muster et al., 1991, "An Influenza A Virus Containing Influenza B Virus 5' and 3' Noncoding Regions on the Neuraminidase Gene is Attenuated in Mice", Proc. Natl. Acad. Sci. USA 88: 5177–5181.

Enami et al., 1991, "An Influenza Virus Containing Nine Different RNA Segments", Virol. 185: 291–298.

Park et al., 1991, "Rescue of a Foreign Gene by Sendai Virus", Proc. Natl. Acad. Sci. USA 88: 5537–5541.

Collins et al., 1991, "Rescue of Synthetic Analogs of Respiratory Syncytial Virus Genomic RNA and Effect of Truncations and Mutations on the Expression of a Foreign Reporter Gene", Proc. Natl. Acad. Sci. USA 88: 5537–5541.

Macejak, D. G. and Sarnow, P., 1991, "Internal Initiation of Translation Mediated by the 5' Leader of a Cellular mRNA", Nature 353: 90–94.

Levis, R. et al., 1987, "Engineered Defective Interfering RNAs of Sindbis Virus Express Bacterial Chloramphenicol Acetyltransferase in Avian Cells", Proc. Natl. Acad. Sci. USA. 84: 4811–4815.

Chanda, P. K. et al., 1983, "In Vitro Transcription of Defective Interfering Particles of Influenza Virus Produces Polyadenylic Acid–Containing Complementary RNAs", J. Virol. 45: 55–61.

Fields, S. et al., 1982, "Nucleotide Sequences of Influenza Virus Segments 1 and 3 Reveal Mosaic Structure of a Small Viral RNA Segment", Cell 28: 303–313.

Pelletier, J. et al., 1988, "Internal Initiation of Translation of Eukaryotic mRNA Directed by a Sequence Derived from Poliovirus RNA", Nature 334: 320–325.

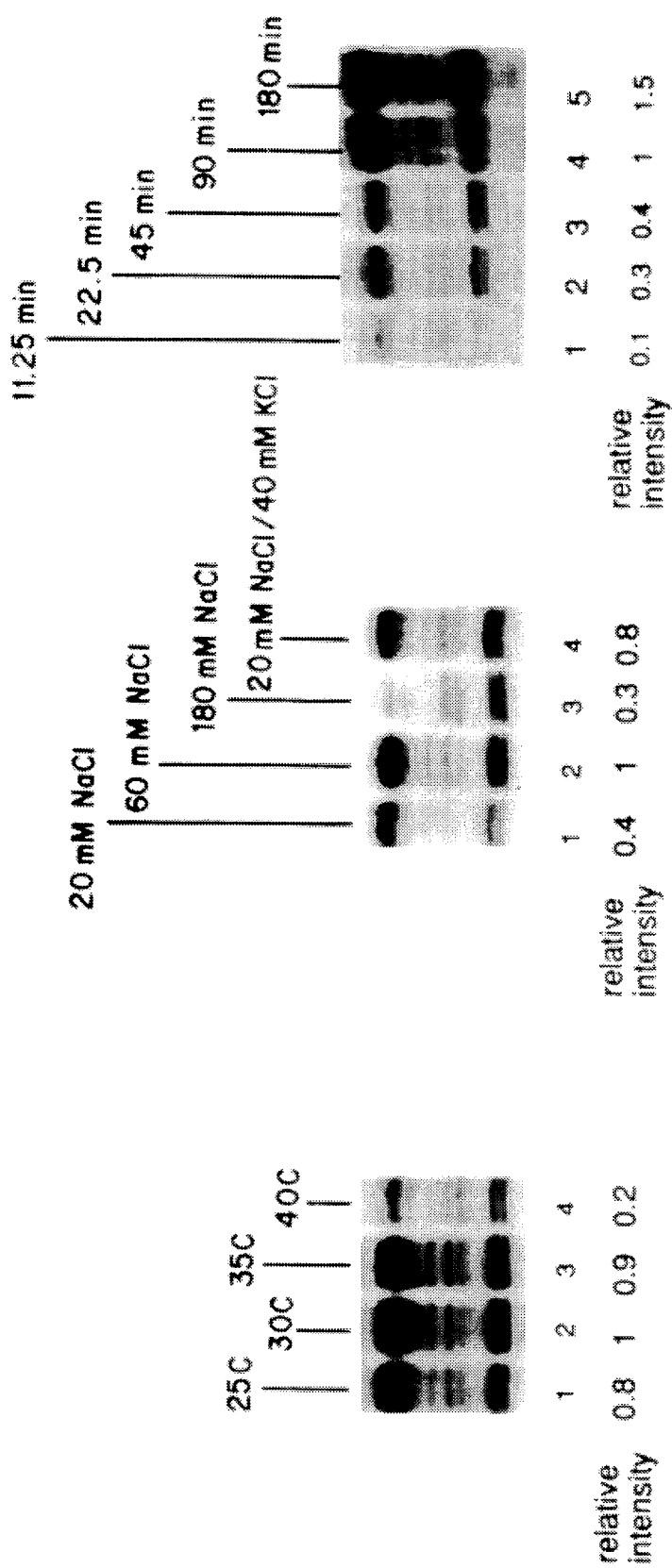

1  2  3     4

FIG.20A
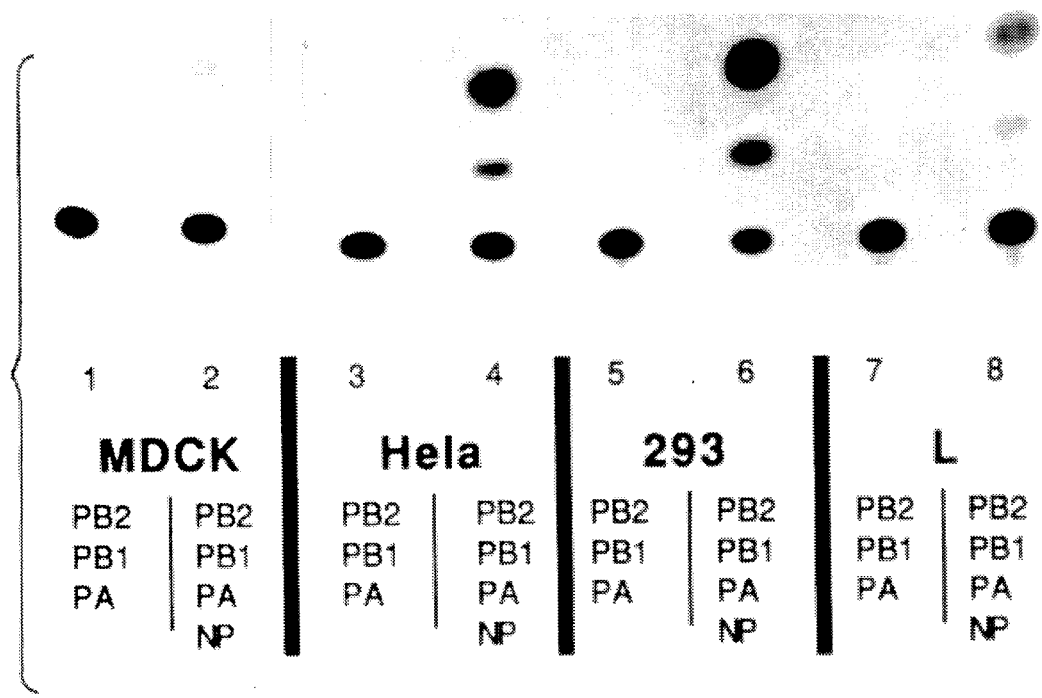
FIG.20B
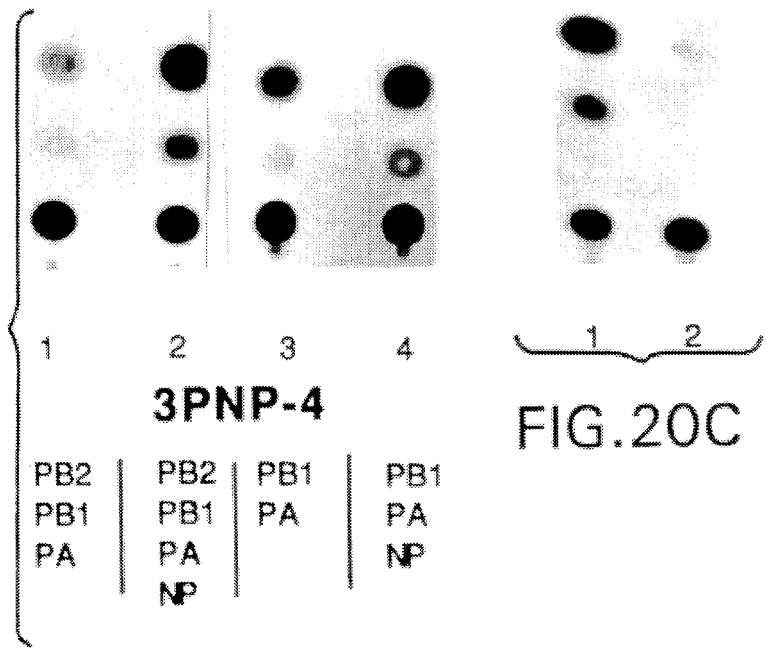
FIG.20C

RECOMBINANT NEGATIVE STRAND RNA VIRUS

This invention was funded in part by a grant by a grant from the National Institutes of Health, and the Government has certain rights in the invention.

This is a division of Ser. No. 08/190,698, filed Feb. 1, 1994, now abandoned, which is a continuation of Ser. No. 07/925,061, filed on Aug. 4, 1992, now abandoned, which is a divisional application of Ser. No. 07/527,237, filed on May 22, 1990, and issued on Nov. 24, 1992 as U.S. Pat. No. 5,166,057, which is a continuation-in-part of Ser. No. 07/440,053, filed Nov. 21, 1989, now abandoned, which is a continuation-in-part of Ser. No. 07/399,728, filed Aug. 28, 1989, now abandoned.

TABLE OF CONTENTS

1. Introduction
2. Background Of The Invention
  2.1. The Influenza Virus
  2.2. RNA Directed RNA Polymerase
  Summary Of The Invention
  3.1. Definitions
4. Description Of The Figures
5. Description Of The Invention
  5.1. Construction Of the Recombinant RNA Templates
    5.1.1. The Viral 3'-Terminus Is Required For Polymerase Activity
    5.1.2. A Terminal Panhandle Is Not Required For Optimal Recognition And Synthesis By The Viral Polymerase
    5.1.3. The RNA Polymerase Preparation Specifically Copies Negative Sense Templates
    5.1.4. Insertion Of The Heterologous Gene Sequence Into The PB2, PB1, PA Or NP Gene Segments
    5.1.5. Insertion Of The Heterologous Gene Sequence Into The HA Or NA Gene Segments
    5.1.6. Insertion Of The Heterologous Gene Into The NS And M Gene Segments
  5.2. Expression Of Heterologous Gene Products Using Recombinant RNA Template
    5.2.1. Purification of the Vital Polymerase
    5.2.2. High Concentrations Of Polymerase Are Required For Cap-Primed RNA Synthesis
    5.2.3. Genomic Length RNA Templates Are Efficiently Copied
  5.3. Preparation Of Chimeric Negative Strand RNA Virus
  5.4. Vaccine Formulations Using The Chimeric Viruses
6. Example: Promoter Analysis Of The Influenza Vital RNA Polymerase
  6.1. Materials And Methods
    6.1.1. Purification Of The Viral RNA Polymerase
    6.1.2. Preparation Of Plasmid
    6.1.3. Preparation Of RNA Templates
    6.1.4. Influenza Viral Polymerase Reactions
    6.1.5. Nuclease Analysis Of Reaction Products
  6.2. Results
    6.2.1. Preparation Of Influenza Viral RNA Polymerase And Of Template RNA
    6.2.2. Viral Polymerase Catalyzes Synthesis Of A Full Length Copy Of The Template
    6.2.3. Conditions For The Polymerase Reactions Using Model RNA Templates
    6.2.4. Specificity Of The Elongation Reaction
    6.2.5. Analysis Of The Promoter Region For The Viral RNA Polymerase
    6.2.6. The Viral Polymerase Does Not Copy RNA Templates Containing Plus-Sense Termini
    6.2.7. Cap-Endonuclease Primed RNA Synthesis
    6.2.8. Replication Of Genomic Length RNA Templates
7. Example: Expression And Packaging Of A Foreign Gene By Recombinant Influenza Virus
  7.1. Materials and Methods
    7.1.1. Viruses and Cells
    7.1.2. Construction of Plasmids
    7.1.3. T7 RNA Transcription
    7.1.4. Purification of Influenza A Virus Polymerase And In Vitro Transcription
    7.1.5. RNP-Transfection Of MDCK And 293 Cells
    7.1.6. Passaging of Virus From RNP-Transfected Cells
    7.1.7. CAT Assays
  7.2. Results
    7.2.1. Synthesis Of IVACATI Template RNA
    7.2.2. The IVACATI RNA Is Transcribed In Vitro By The Influenza A Virus RNA Polymerase
    7.2.3. RNP-Transfection And CAT Activity
    7.2.4. The CAT-RNP Is Packaged Into Virus Particles
8. Rescue Of Infectious Influenza Viruses Using RNA Derived From Specific Recombinant DNAs
  8.1. Materials and Methods
    8.1.1. Viruses and Cells
    8.1.2. Construction of Plasmids
    8.1.3. Purification Of Influenza A Virus Polymerase And RNP Transfection In MDBK Cells
  8.2. Results
    8.2.1. Rescue Of Infectious Influenza Virus In MDBK Cells Using RNA Derived From Recombinant Plasmid DNA
    8.2.2. RNA Analysis Of Rescued Virus
    8.2.3. Rescue Of Infectious Influenza Virus Using Virion RNA
    8.2.4. Introduction Of Site Specific Mutations Into The Viral Genome
9. Example: Synthetic Replication System
10. Deposit Of Microorganisms

1. INTRODUCTION

The present invention relates to recombinant negative strand virus RNA templates which may be used to express heterologous gene products in appropriate host cell systems and/or to construct recombinant viruses that express, package, and/or present, the heterologous gene product. The expression products and chimeric viruses may advantageously be used in vaccine formulations.

The invention is demonstrated by way of examples in which recombinant influenza virus RNA templates containing a heterologous gene coding sequences in the negative-polarity were constructed. These recombinant templates, when combined with purified viral RNA-directed RNA polymerase, were infectious, replicated in appropriate host cells, and expressed the heterologous gene product at high levels. In addition, the heterologous gene was expressed and packaged by the resulting recombinant influenza viruses.

2. BACKGROUND OF THE INVENTION

A number of DNA viruses have been genetically engineered to direct the expression of heterologous proteins in host cell systems (e.g., vaccinia virus, baculovirus, etc.). Recently, similar advances have been made with positive-strand RNA viruses (e.g., poliovirus). The expression products of these constructs, i.e., the heterologous gene product or the chimeric virus which expresses the heterologous gene product, are thought to be potentially useful in vaccine formulations (either subunit or whole virus vaccines). One drawback to the use of viruses such as vaccinia for constructing recombinant or chimeric viruses for use in vaccines is the lack of variation in its major epitopes. This lack of variability in the viral strains places strict limitations on the repeated use of chimeric vaccinia, in that multiple vaccinations will generate host-resistance to the strain so that the inoculated virus cannot infect the host. Inoculation of a resistant individual with chimeric vaccine will, therefore, not induce immune stimulation.

By contrast, influenza virus, a negative-strand RNA virus, demonstrates a wide variability of its major epitopes. Indeed, thousands of variants of influenza have been identified; each strain evolving by antigenic drift. The negative-strand viruses such as influenza would be attractive candidates for constructing chimeric viruses for use in vaccines because its genetic variability allows for the construction of a vast repertoire of vaccine formulations which will stimulate immunity without risk of developing a tolerance. However, achieving this goal has been precluded by the fact that, to date, it has not been possible to construct recombinant or chimeric negative-strand RNA particles that are infectious.

2.1. THE INFLUENZA VIRUS

Virus families containing enveloped single-stranded RNA of the negative-sense genome are classified into groups having non-segmented genomes (Paramyxoviridae, Rhabdoviridae) or those having segmented genomes (Orthomyxoviridae, Bunyaviridae and Arenaviridae). The Orthomyxoviridae family, described in detail below, and used in the examples herein, contains only the viruses of influenza, types A, B and C.

The influenza virions consist of an internal ribonucleoprotein core (a helical nucleocapsid) containing the single-stranded RNA genome, and an outer lipoprotein envelope lined inside by a matrix protein (M). The segmented genome of influenza A consists of eight molecules (seven for influenza C) of linear, negative polarity, single-stranded RNAs which encode ten polypeptides, including: the RNA-directed RNA polymerase proteins (PB2, PB1 and PA) and nucleoprotein (NP) which form the nucleocapsid; the matrix proteins (M1, M2); two surface glycoproteins which project from the lipoprotein envelope: hemagglutinin (HA) and neuraminidase (NA); and nonstructural proteins whose function is unknown (NS1 and NS2). Transcription and replication of the genome takes place in the nucleus and assembly occurs via budding on the plasma membrane. The viruses can reassort genes during mixed infections.

Influenza virus adsorbs via HA to sialyloligosaccharides in cell membrane glycoproteins and glycolipids. Following endocytosis of the virion, a conformational change in the HA molecule occurs within the cellular endosome which facilitates membrane fusion, thus triggering uncoating. The nucleocapsid migrates to the nucleus where viral mRNA is transcribed as the essential initial event in infection. Viral mRNA is transcribed by a unique mechanism in which viral endonuclease cleaves the capped 5'-terminus from cellular heterologous mRNAs which then serve as primers for transcription of viral RNA templates by the viral transcriptase. Transcripts terminate at sites 15 to 22 bases from the ends of their templates, where oligo(U) sequences act as signals for the template-independent addition of poly(A) tracts. Of the eight viral mRNA molecules so produced, six are monocistronic messages that are translated directly into the proteins representing HA, NA, NP and the viral polymerase proteins, PB2, PB1 and PA. The other two transcripts undergo splicing, each yielding two mRNAs which are translated in different reading frames to produce M1, M2, NS1 and NS2. In other words, the eight viral mRNAs code for ten proteins: eight structural and two nonstructural. A summary of the genes of the influenza virus and their protein products is shown in Table I below.

TABLE I

Influenza Virus Genome RNA Segments and Coding Assignments[a]

| Segment | Length[b] (Nucleotides) | Encoded Polypeptide[c] | Length[d] (Amino Acids) | Molecules Per Virion | Comments |
|---|---|---|---|---|---|
| 1 | 2341 | PB2 | 759 | 30–60 | RNA transcriptase component; host cell RNA cap binding |
| 2 | 2341 | PB1 | 757 | 30–60 | RNA transcriptase component; initiation of transcription; endonuclease activity? |
| 3 | 2233 | PA | 716 | 30–60 | RNA transcriptase component; elongation of mRNA chains? |
| 4 | 1778 | HA | 566 | 500 | Hemagglutinin; trimer; envelope glycoprotein; mediates attachment to cells |
| 5 | 1565 | NP | 498 | 1000 | Nucleoprotein; associated with RNA; structural component of RNA transcriptase |
| 6 | 1413 | NA | 454 | 100 | Neuraminidase; tetramer; envelope glycoprotein |
| 7 | 1027 | $M_1$ | 252 | 3000 | Matrix protein; lines inside of envelope |
|  |  | $M_2$ | 96 |  | Structural protein in plasma membrane; spliced mRNA |
|  |  | ? | ?9 |  | Unidentified protein |
| 8 | 890 | $NS_1$ | 230 |  | Nonstructural protein; function unknown |
|  |  | $NS_2$ | 121 |  | Nonstructural protein; function unknown; spliced mRNA |

TABLE I-continued

Influenza Virus Genome RNA Segments and Coding Assignments[a]

| Segment | Length[b] (Nucleotides) | Encoded Polypeptide[c] | Length[d] (Amino Acids) | Molecules Per Virion | Comments |
|---------|-------------------------|------------------------|-------------------------|----------------------|----------|

[a]Adapted from R. A. Lamb and P. W. Choppin (1983), Reproduced from the Annual Review of Biochemistry, Volume 52, 467–506.
[b]For A/PR/8/34 strain
[c]Determined by biochemical and genetic approaches
[d]Determined by nucleotide sequence analysis and protein sequencing Following transcription, virus genome replication is the second essential event in infection by negative-strand RNA viruses. As with other negative-strand RNA viruses, virus genome replication in influenza is mediated by virus-specified proteins. It is hypothesized that most or all of the viral proteins that transcribe influenza virus mRNA segments also carry out their replication. All viral RNA segments have common 3' and 5' termini, presumably to enable the RNA-synthesizing apparatus to recognize each segment with equal efficiency. The mechanism that regulates the alternative uses (i.e., transcription or replication) of the same complement of proteins (PB2, PB1, PA and NP) has not been clearly identified but appears to involve the abundance of free forms of one or more of the nucleocapsid proteins, in particular, the NP. The nucleus appears to be the site of virus RNA replication, just as it is the site for transcription.

The first products of replicative RNA synthesis are complementary copies (i.e., plus-polarity) of all influenza virus genome RNA segments (cRNA). These plus-stranded copies (anti-genomes) differ from the plus-strand mRNA transcripts in the structure of their termini. Unlike the mRNA transcripts, the anti-genomic cRNAs are not, capped and methylated at the 5' termini, and are not truncated and polyadenylated at the 3' termini. The cRNAs are coterminal with their negative strand templates and contain all the genetic information in each genomic RNA segment in the complementary form. The cRNAs serve as templates for the synthesis of genomic negative-strand vRNAs.

The influenza virus negative strand genomes (vRNAs) and antigenomes (cRNAs) are always encapsidated by nucleocapsid proteins; the only unencapsidated RNA species are virus mRNAs. In contrast to the other enveloped RNA viruses, nucleocapsid assembly appears to take place in the nucleus rather than in the cytoplasm. The virus matures by budding from the apical surface of the cell incorporating the M protein on the cytoplasmic side or inner surface of the budding envelope. The HA and NA become glycosylated and incorporated into the lipid envelope. In permissive cells, HA is eventually cleaved, but the two resulting chains remain united by disulfide bonds.

It is not known by what mechanism one copy of each of the eight genomic viral RNAs is selected for incorporation into each new virion. Defective interfering (DI) particles are often produced, especially following infection at high multiplicity.

2.2. RNA DIRECTED RNA POLYMERASE

The RNA-directed RNA polymerases of animal viruses have been extensively studied with regard to many aspects of protein structure and reaction conditions. However, the elements of the template RNA which promote optimal expression by the polymerase could only be studied by inference using existing viral RNA sequences. This promoter analysis is of interest since it is unknown how a viral polymerase recognizes specific viral RNAs from among the many host-encoded RNAs found in an infected cell.

Animal viruses containing plus-sense genome RNA can be replicated when plasmid-derived RNA is introduced into cells by transfection (for example, Racaniello et al., 1981, Science 214:916–919; Levis, et al., 1986, Cell 44: 137–145). In the case of poliovirus, the purified polymerase will replicate a genome RNA in in vitro reactions and when this preparation is transfected into cells it is infectious (Kaplan, et al., 1985, Proc. Natl. Acad. Sci. U.S.A. 82:8424–8428). However, the template elements which serve as transcription promoter for the poliovirus-encoded polymerase are unknown since even RNA homopolymers can be copied (Ward, et al., 1988, J. Virol. 62: 558–562). SP6 transcripts have also been used to produce model defective interfering (DI) RNAs for the Sindbis viral genome. When the RNA is introduced into infected cells, it is replicated and packaged. The RNA sequences which were responsible for both recognition by the Sindbis viral polymerase and packaging of the genome into virus particles were shown to be within 162 nucleotides (nt) of the 5' terminus and 19 nt of the 3' terminus of the genome (Levis, et al., 1986, Cell 44: 137–145). In the case of brome mosaic virus (BMV), a positive strand RNA plant virus, SP6 transcripts have been used to identify the promoter as a 134 nt tRNA-like 3' terminus (Dreher, and Hall, 1988, J. Mol. Biol. 201: 31–40). Polymerase recognition and synthesis were shown to be dependent on both sequence and secondary structural features (Dreher, et al., 1984, Nature 311: 171–175).

The negative-sense RNA viruses have been refractory to study of the sequence requirements of the replicase. The purified polymerase of vesicular stomatitis virus is only active in transcription when virus-derived ribonucleoprotein complexes (RNPs) are included as template (De and Banerjee, 1985, Biochem. Biophys. Res. Commun. 126: 40–49; Emerson and Yu, 1975, J. Virol. 15: 1348–1356; Naito, and Ishihama, 1976, J. Biol. Chem. 251: 4307–4314). RNPs have been reconstituted from naked RNA of VSV DI particles using infected cell extracts as protein source. These RNPs were then replicated when added back to infected cells (Mirakhur, and Peluso, 1988, Proc. Natl. Acad. Sci. U.S.A. 85: 7511–7515). With regard to influenza viruses, it was recently reported that naked RNA purified from virus was used to reconstitute RNPs. The viral nucleocapsid and polymerase proteins were gel-purified and renatured on the viral RNA using thioredoxin (Szewczyk, et al., 1988, Proc. Natl. Acad. Sci. U.S.A., 85: 7907–7911). However, these authors did not show that the activity of the preparation was specific for influenza viral RNA, nor did they analyze the signals which promote transcription.

During the course of influenza virus infection the polymerase catalyzes three distinct transcription activities. These include the synthesis of (a) subgenomic mRNA, which contains a 5' cap and a 3' poly-A tail; (b) a full length plus-strand or anti-genome (cRNA) copied from the genome RNA; and (c) genomic vRNA synthesized from the full length cRNA (reviewed in Ishihama and Nagata, 1988, CRC Crit. Rev. Biochem. 23: 27–76; and Krug, Transcription and replication of influenza viruses. In: Genetics of influenza viruses, Ed., Palese, P. and Kingsbury, D. W. New York, Springer-Verlag, 1983, p. 70–98). Viral proteins PB2, PB1 and PA are thought to catalyze all influenza virus-specific RNA synthesis when in the presence of excess nucleocapsid protein (NP; see above reviews). These polymerase functions have been studied using RNP cores derived from detergent-disrupted virus, and RNPs from the nuclear extracts of infected cells. Transcription from the RNPs derived from disrupted virus occurs when primed with either dinucleotide adenylyl-(3'-5')-guanosine (ApG) or capped mRNAs. The plus sense mRNA products have terminated synthesis 17–20 nucleotides upstream of the 5' terminus of the RNA template and have been processed by the addition of poly A tails. These products cannot serve as template for the viral-sense genome since they lack terminal sequences (Hay, et al., 1977, Virology 83: 37–355). RNPs derived from nuclear extracts of infected cells also synthesize polyadenylated mRNA in the presence of capped RNA primers. However, if ApG is used under these conditions, both RNAs, polyadenylated and full length cRNA, can be obtained (Beaton and Krug, 1986, Proc. Natl. Acad. Sci. U.S.A. 83: 6282–6286; Takeuchi, et al., 1987, J. Biochem. 101: 837–845). Recently it was shown that replicative synthesis of cRNA could occur in the absence of exogenous primer if the nuclear extract was harvested at certain times post infection. In these same preparations the synthesis of negative-sense vRNA from a cRNA template was also observed (Shapiro and Krug, 1988, J. Virol. 62: 2285–2290). The synthesis of full length cRNA was shown to be dependent upon the presence of nucleocapsid protein (NP) which was free in solution (Beaton and Krug, 1986, Proc. Natl. Acad. Sci. U.S.A. 83: 6282–6286; Shapiro and Krug, 1988, J. Virol. 62: 2285–2290). These findings led to the suggestion that the regulatory control between mRNA and cRNA synthesis by the RNP complex is based on the requirement for there being an excess of soluble NP (Beaton and Krug, 1986, Proc. Natl. Acad. Sci. U.S.A. 83: 6282–6286).

Another line of investigation has focused on the preparation of polymerase-RNA complexes derived from RNPs from detergent-disrupted virus. When the RNP complex is centrifuged through a CsCl-glycerol gradient, the RNA can be found associated with the three polymerase (P) proteins at the bottom of the gradient. Near the top of the gradient, free NP protein can be found (Honda, et al., 1988, J. Biochem. 104: 1021–1026; Kato, et al., 1985, Virus Research 3, 115–127). The purified polymerase-RNA complex (bottom of gradient), is active in initiating ApG-primed synthesis of RNA, but fails to elongate to more than 12–19 nucleotides. When fractions from the top of the gradient containing the NP protein are added back to the polymerase-RNA complex, elongation can ensue (Honda, et al., 1987, J. Biochem. 102: 41–49). These data suggest that the NP protein is needed for elongation, but that initiation can occur in the absence of NP.

It has been shown that the genomic RNA of influenza viruses is in a circular conformation via base-pairing of the termini to form a panhandle of 15 to 16 nt (Honda, et al., 1988, J. Biochem. 104: 1021–1026; Hsu, et al., 1987, Proc. Natl. Acad. Sci. U.S.A. 84: 8140–8144). Since the viral polymerase was found bound to the panhandle, this led to the suggestion that a panhandle structure was required for recognition by the viral polymerase (Honda, et al., 1988, J. Biochem. 104: 1021–1026.) Therefore, it was hypothesized in these two reports that the promoter for the viral RNA polymerase was the double stranded RNA in panhandle conformation.

3. SUMMARY OF THE INVENTION

Recombinant negative-strand viral RNA templates are described which may be used with purified RNA-directed RNA polymerase complex to express heterologous gene products in appropriate host cells and/or to rescue the heterologous gene in virus particles. The RNA templates are prepared by transcription of appropriate DNA sequences with a DNA-directed RNA polymerase. The resulting RNA templates are of the negative-polarity and contain appropriate terminal sequences which enable the viral RNA-synthesizing apparatus to recognize the template.

As demonstrated by the examples described herein, recombinant negative-sense influenza RNA templates may be mixed with purified viral polymerase proteins and nucleoprotein (i.e., the purified viral polymerase complex) to form infectious recombinant RNPs. These can be used to express heterologous gene products in host cells or to rescue the heterologous gene in virus particles by cotransfection of host cells with recombinant RNPs and virus. Alternatively, the recombinant RNA templates or recombinant RNPs may be used to transfect transformed cell lines that express the RNA dependent RNA-polymerase and allow for complementation. Additionally, a non-virus dependent replication system for influenza virus is also described. Vaccinia vectors expressing influenza virus polypeptides were used as the source of proteins which were able to replicate and transcribe synthetically derived RNPs. The minimum subset of influenza virus protein needed for specific replication and expression of the viral RNP was found to be the three polymerase proteins (PB2, PB1 and PA) and the nucleoprotein (NP). This suggests that the nonstructural proteins, NS1 and NS2, are not absolutely required for the replication and expression of viral RNP.

The expression products and/or chimeric virions obtained may advantageously be utilized in vaccine formulations. The use of recombinant influenza for this purpose is especially attractive since influenza demonstrates tremendous strain variability allowing for the construction of a vast repertoire of vaccine formulations. The ability to select from thousands of influenza variants for constructing chimeric viruses obviates the problem of host resistance encountered when using other viruses such as vaccinia. In addition, since influenza stimulates a vigorous secretory and cytotoxic T cell response, the presentation of foreign epitopes in the influenza virus background may also provide for the induction of secretory immunity and cell-mediated immunity.

3.1. DEFINITIONS

As used herein, the following terms will have the meanings indicated:
cRNA =anti-genomic RNA
HA=hemagglutinin (envelope glycoprotein)
M=matrix protein (lines inside of envelope)
MDCK=Madin Darby canine kidney cells
MDBK=Madin Darby bovine kidney cells
moi=multiplicity of infection
NA=neuraminidase (envelope glycoprotein)
NP=nucleoprotein (associated with RNA and required for polymerase activity)
NS=nonstructural protein (function unknown)
nt=nucleotide
PA, PB1, PB2=RNA-directed RNA polymerase components
RNP=ribonucleoprotein (RNA, PB2, PB1, PA and NP)
rRNP=recombinant RNP
VRNA=genomic virus RNA
viral polymerase complex=PA, PB1, PB2 and NP
WSN=influenza A/WSN/33 virus
WSN-HK virus: reassortment virus containing seven genes from WSN virus and the NA gene from influenza A/HK/8/68 virus

4. DESCRIPTION OF THE FIGURES

FIG. 1. Purification of the polymerase preparation. RNP cores were purified from whole virus and then subjected to CsCl-glycerol gradient centrifugation. The polymerase was purified from fractions with 1.5 to 2.0M CsCl. Samples were then analyzed by polyacrylamide gel electrophoresis on a 7–14% linear gradient gel in the presence of 0.1% sodium dodecylsulfate followed by staining with silver. Protein samples contained 1.4 μg whole virus (lane 1), 0.3 μg whole virus (lane 5), 5 μl of RNP cores (lane 3) and 25 μl RNA polymerase (lane 4). Known assignments of the proteins are indicated at the left.

Figure 2:
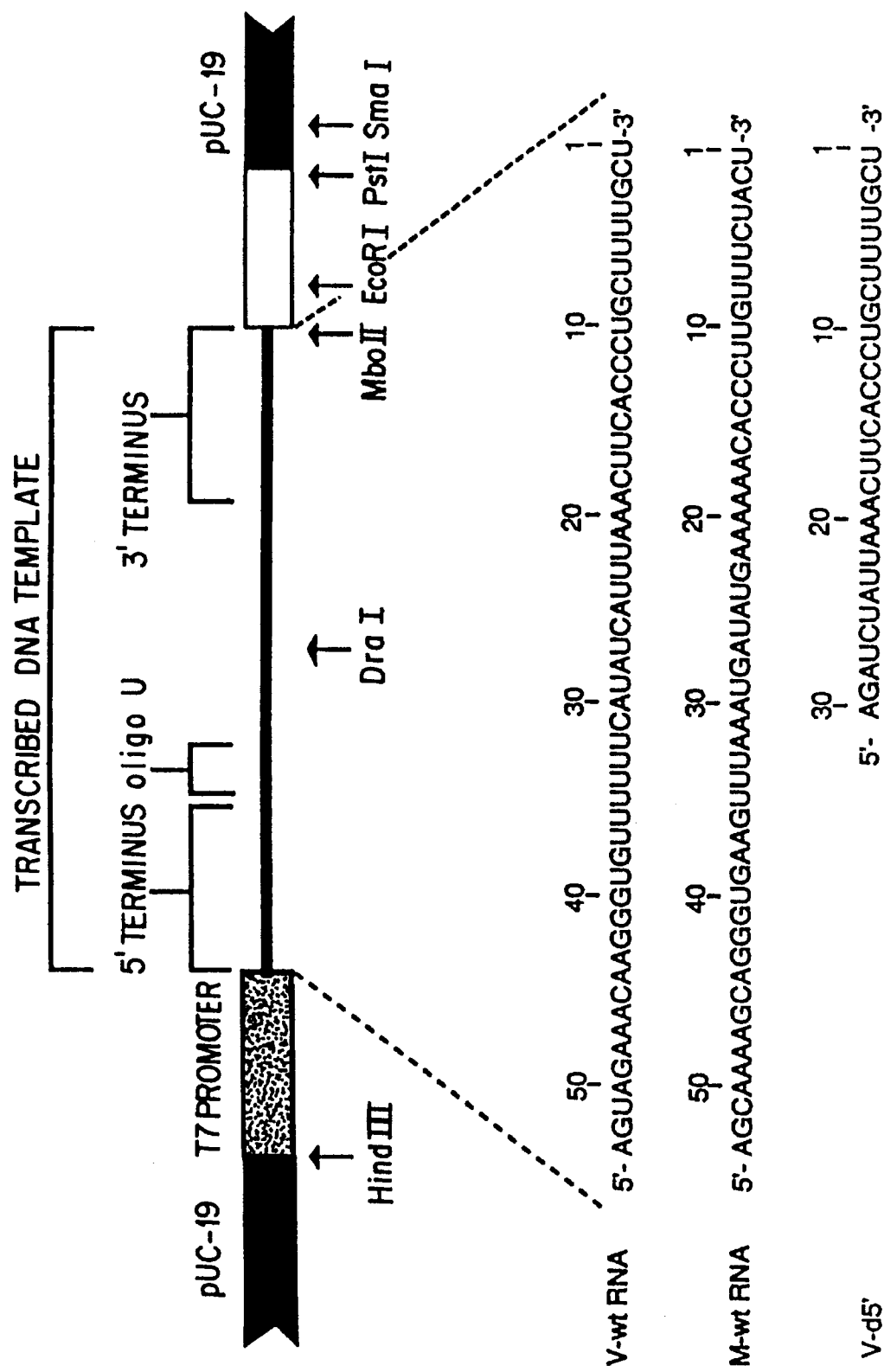

FIG. 2. Plasmid constructs used to prepare RNA templates. The plasmid design is depicted with the solid box representing pUC-19 sequences, the hatched box represents the truncated promoter specifically recognized by bacteriophage T7 RNA polymerase, the solid line represents the DNA which is transcribed from plasmids which have been digested with MboII. The white box represents sequences encoding the recognition sites for MboII, EcoRI and PstI, in that order. Sites of cleavage by restriction endonucleases are indicated. Beneath the diagram, the entire sequences of RNAs which result from synthesis by T7 RNA polymerase from MboII-digested plasmid are given. The V-wt RNA has the identical 5' and 3' termini as found in RNA segment 8 of influenza A viruses, separated by 16 "spacer" nucleotides. The RNA, M-wt, represents the exact opposite stand, or "message-sense", of V-wt. Restriction endonuclease sites for DraI, EcoRI, PstI and SmaI are indicated. T7 transcripts of plasmids cleaved by these enzymes result in, respectively, 32, 58, 66 and 91 nucleotide long RNAs. The sequences of V-d5' RNA are indicated. The plasmid design is essentially the same as that used for the V-wt RNA except for the minor changes in the "spacer" sequence. The point mutants of V-d5' RNAs which were studied are indicated in Table I.

Figures 3A, 3B, 3C:
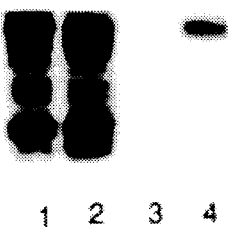

FIG. 3A–C. Analysis of products of influenza viral polymerase. FIG. 3A: Polymerase reaction mixtures containing 0.4 mM ApG (lane 2) or no primer (lane 3) were electrophoresed on 8% polyacrylamide gels containing 7.7M urea. FIG. 3B: The nascent RNA is resistant to single-stranded specific nuclease S1. Following the standard polymerase reaction, the solutions were diluted in nuclease S1 buffer (lane 1) and enzyme was added (lane 2). As control for S1 digestion conditions, radioactively labeled single-stranded V-wt RNA was treated with nuclease S1 (lane 3) or with buffer alone (lane 4). FIG. 3C: Ribonuclease T1 analysis of gel-purified reaction products. The reaction products of the viral polymerase using the V-wt RNA template was subjected to electrophoresis on an 8% polyacrylamide gel. The 53 nt band and the smaller transcript were excised and eluted from the gel matrix. These RNAs were digested with RNAse T1 and analyzed by electrophoresis on a 20% polyacrylamide gel containing 7.7M urea. For comparison, T7 transcripts of M-wt and V-wt RNAs which had been synthesized in the presence of a α-$^{32}$P-UTP were also analyzed with RNAse T1. The predicted radiolabeled oliognucleotides of the control RNAs are indicated. Lane 1, 53 nucleotide full length (FL) product; lane 2, 40–45 nucleotide smaller (Sm) RNA product; lane 3, M-wt RNA labeled by incorporation of $^{32}$P-UMP; and lane 4, V-wt RNA labeled as in lane 3.

FIG. 4A–C. Optimal reaction conditions for the viral polymerase. FIG. 4A: Reactions with V-wt template were assembled on ice and then incubated at the indicated temperatures for 90 minutes. FIG. 4B: Reactions with the V-wt template were prepared in parallel with the indicated NaCl or KCl concentrations and were incubated at 30° C. for 90 minutes. FIG. 4C: A single reaction with the V-wt template was incubated at 30° C., and at the indicated times, samples were removed and immediately processed by phenol-chloroform extraction. All gels contained 8% polyacrylamide with 7.7M urea.

Figures 5A, 5B:
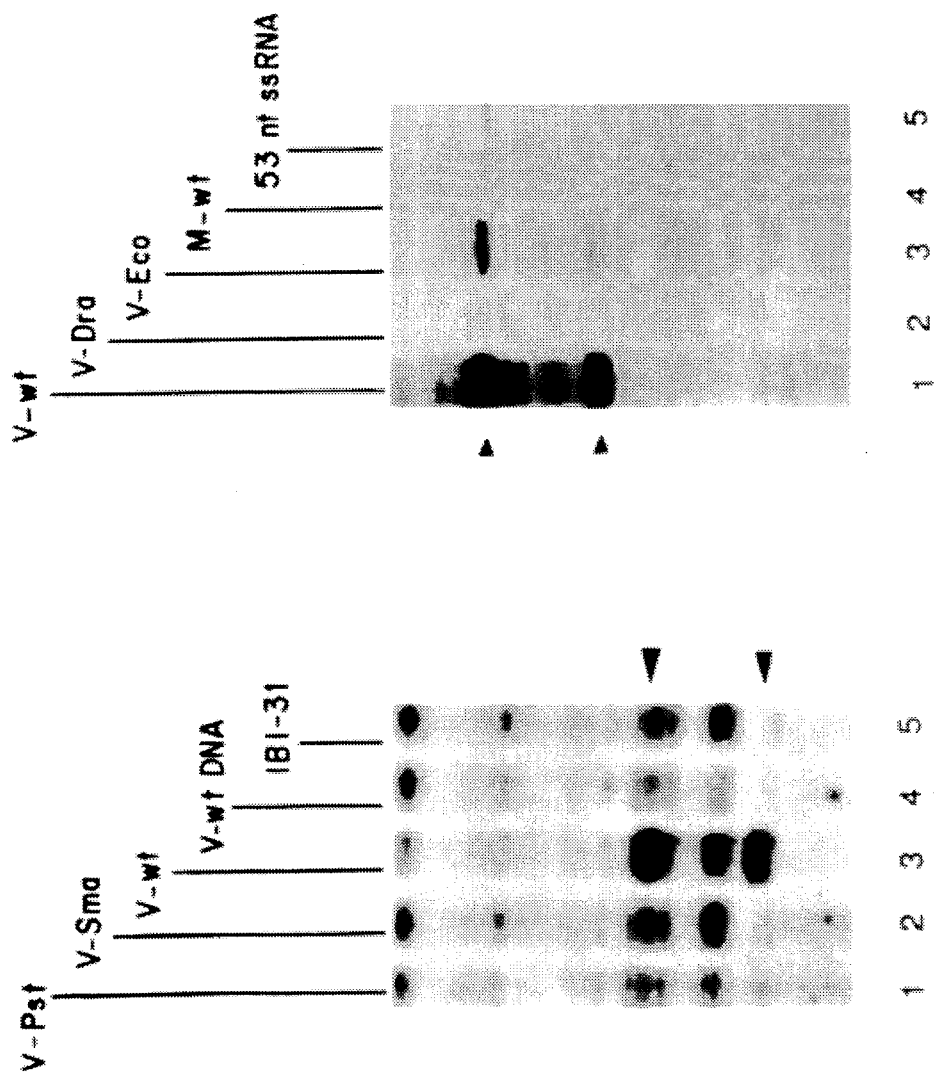

FIG. 5A–B. Template specificity of the viral polymerase. FIG. 5A: The viral polymerase reaction requires 3' terminal promoter sequences. Different template RNAs were used in reactions under standard conditions. Lane 1, the V-Pst RNA, which is identical to V-wt except it has a 13 nt extension at the 3' end; lane 2, V-Sma RNA, which has a 38 nt extension at the 3' end; lane 3, V-wt RNA; lane 4, a DNA polynucleotide with identical sequence as the V-wt RNA; lane 5, an 80 nt RNA generated by bacteriophage T3 RNA polymerase transcription of a pIBI-31 plasmid digested with HindIII. The autoradiograph was overexposed in order to emphasize the absence of specific reaction products when these other templates were used. FIG. 5B: 10 ng of each template RNA were incubated with the viral polymerase and the products were then subjected to electrophoresis on 8% polyacrylamide gels containing 7.7M urea. Lane 1, V-wt RNA; lane 2, V-Dra RNA; lane 3, V-Eco RNA; lane 4, M-wt RNA are shown; and lane 5, a 53nt marker oligonucleotide. For the exact sequence differences refer to FIG. 2 and Section 6.1 et seq.

Figure 6:
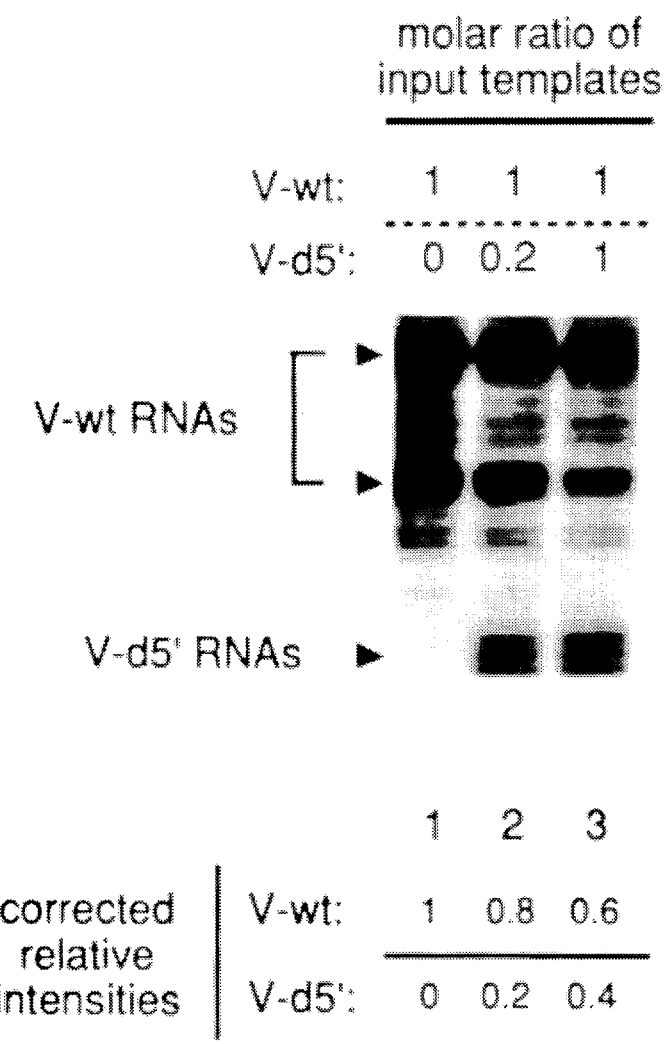

FIG. 6. The RNA promoter does not require a terminal panhandle. Polymerase reaction using two template RNAs. Each reaction contained 5 ng of V-wt RNA. As a second template the reactions contained 0 ng (lane 1), 0.6 ng (lane 2), and 3.0 ng (lane 3) of V-d5' RNA. The resulting molar ratios are as indicated in the figure. The reaction products were analyzed on an 8% polyacrylamide gel in the presence of 7.7M urea. Following densitometry analysis of autoradiographs, the relative intensity of each peak was corrected for the amount of radioactive UMP which is incorporated in each product.

Figure 7:
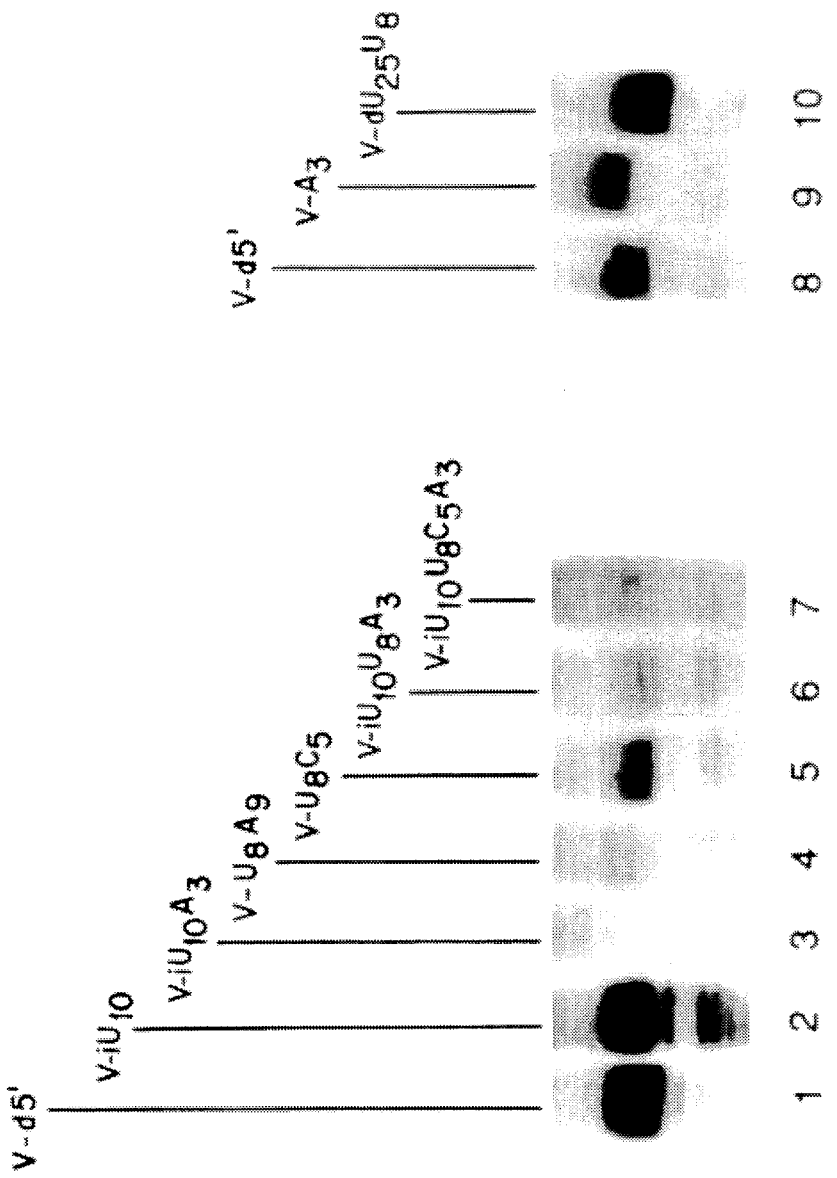

FIG. 7. Specificity of promoter sequences. RNAs which lacked the 5' terminus and contained point mutations (Table II) were compared with V-d5' RNA in standard polymerase reactions. The right panel is from a separate reaction set. Quantitative comparisons is outlined in Table II.

Figure 8:
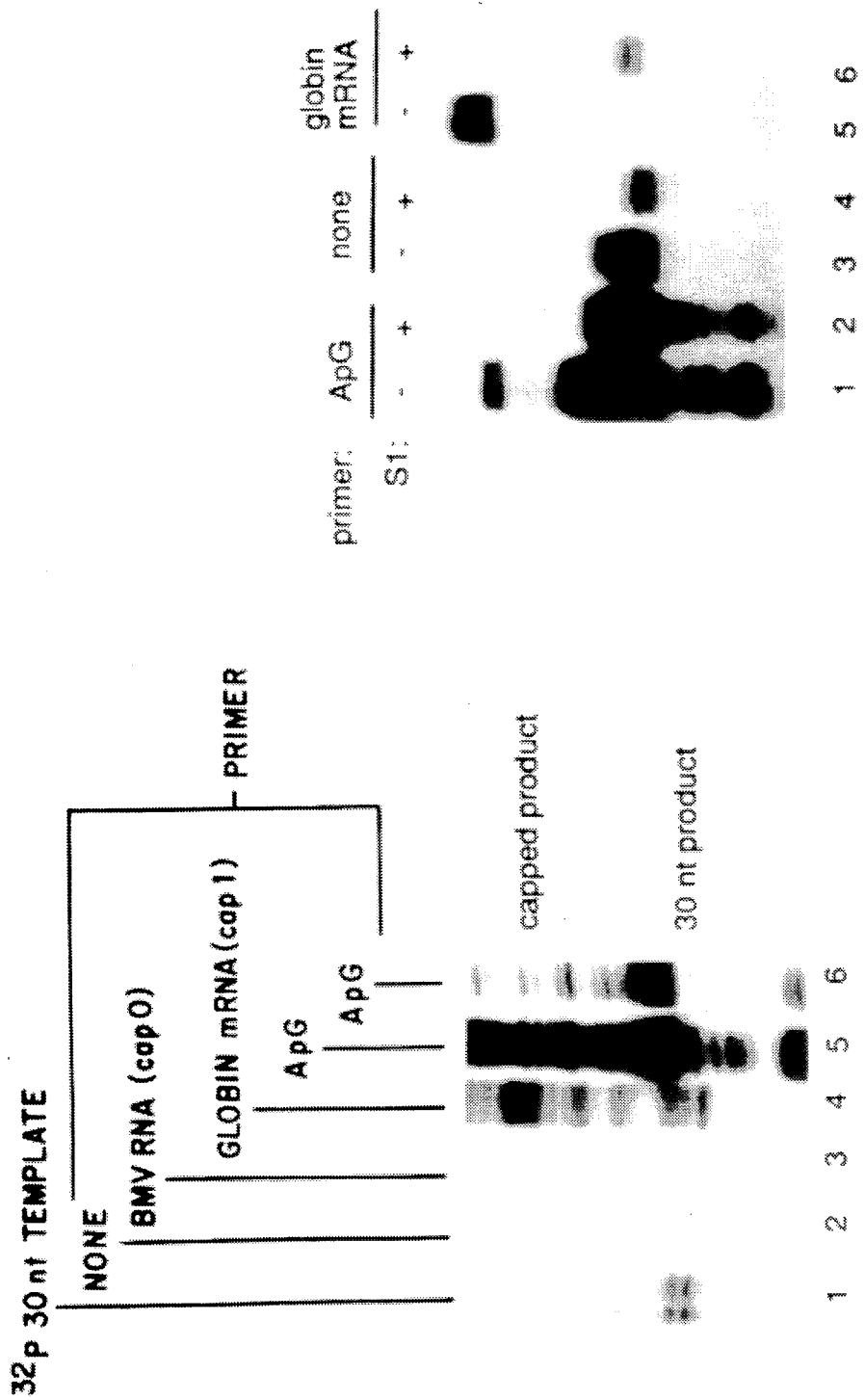

FIG. 8A–B. High concentration polymerase preparations are active in cap-endonuclease primed and in primerless RNA synthesis reactions. FIG. 8A: Primer specificty of the high concentration enzyme. Radioactively synthesized 30 nt template is in lane 1. Reactions using 20 ng of V-d5' RNA and 5 μl of vital polymerase contained as primer: no primer (lane 2); 100 ng BMV RNA (De and Banerjee, 1985, Biochem. Biophys. Res. Commun. 6:40–49) containing a cap 0 structure (lane 3); 100 ng rabbit globin mRNA, containing a cap 1 structure, (lane 4); and 0.4 mM ApG (lane 5). A lighter exposure of lane 5 is shown as lane 6. FIG. 8B: Nuclease S1 analysis of gel-purified RNAs. Products from reactions using as primer ApG (lanes 1 and 2); no primer (lanes 3 and 4); or globin mRNA (lanes 5 and 6) were electrophoresed in the absence of urea and the appropriate gel piece was excised and the RMA was eluded. This RNA was then digested with nuclease S1 (lanes 2, 4, and 6) and the products were denatured and analyzed on an 8% polyacrylamide gel containing 7.7M urea.

Figure 9:
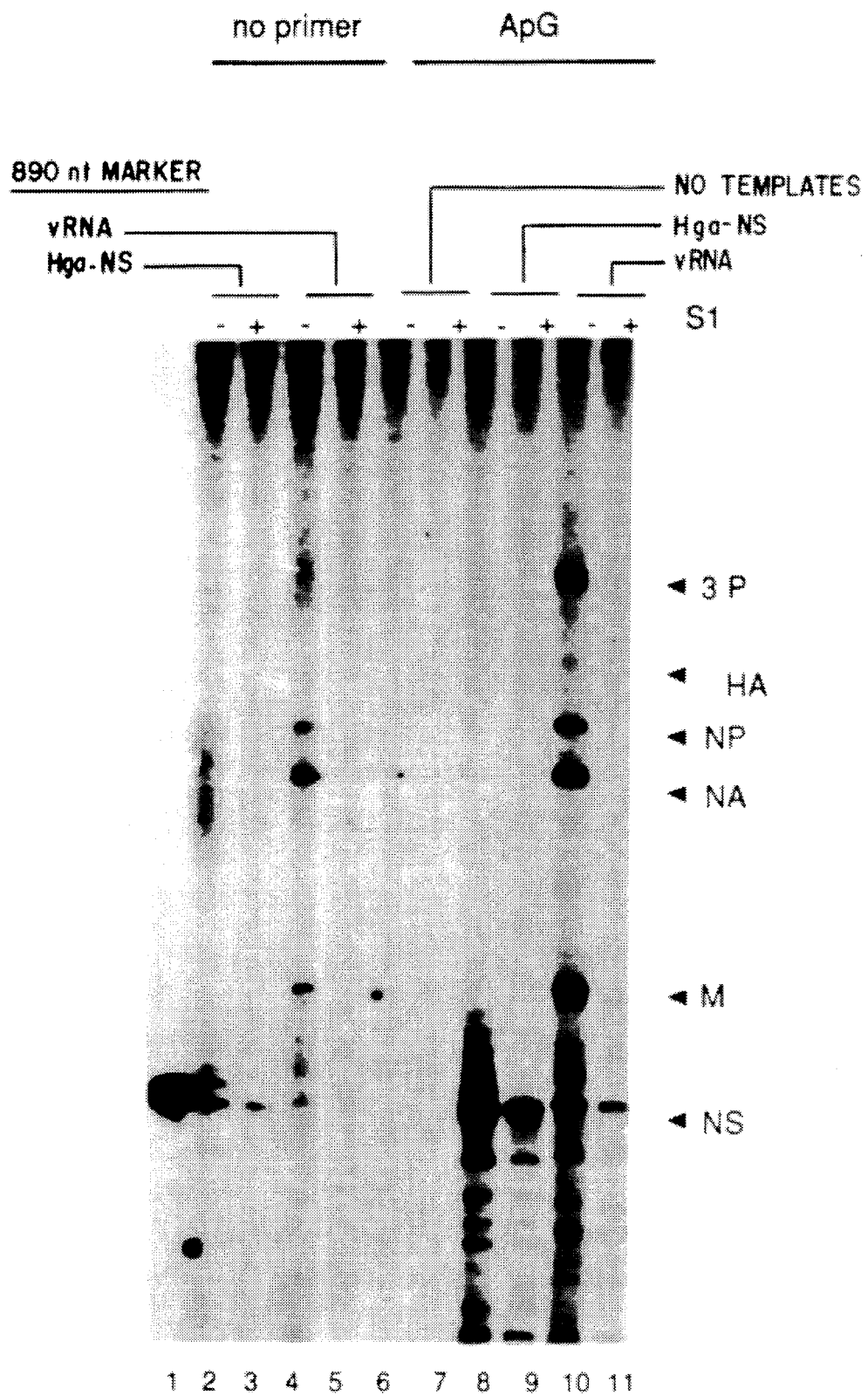

FIG. 9. Genomic length RNA synthesis from reconstituted RNPs. Reaction products using 10 μl of polymerase and as template 890 nt RNA identical to the sequence of segment 8 of virus A/WSN/33 and RNA extracted from A/PR/8/34 virus were analyzed on a 4% polyacrylamide gel containing 7.7M urea. In lane 1, the 890 nt template synthesized radioactively by T7 RNA polymerase is shown. The 890 nt plasmid-derived RNA was used as template in lanes 2, 3, 8 and 9. RNA extracted from virus was used as template in lanes 4, 5, 10 and 11. No template was used in lanes 6 and 7. No primer was used in lanes 2 to 5, and ApG was used as primer in lanes 6 to 11. Reaction products were treated with nuclease S1 in lanes 3, 5, 7, 9 and 11.

Figure 10:
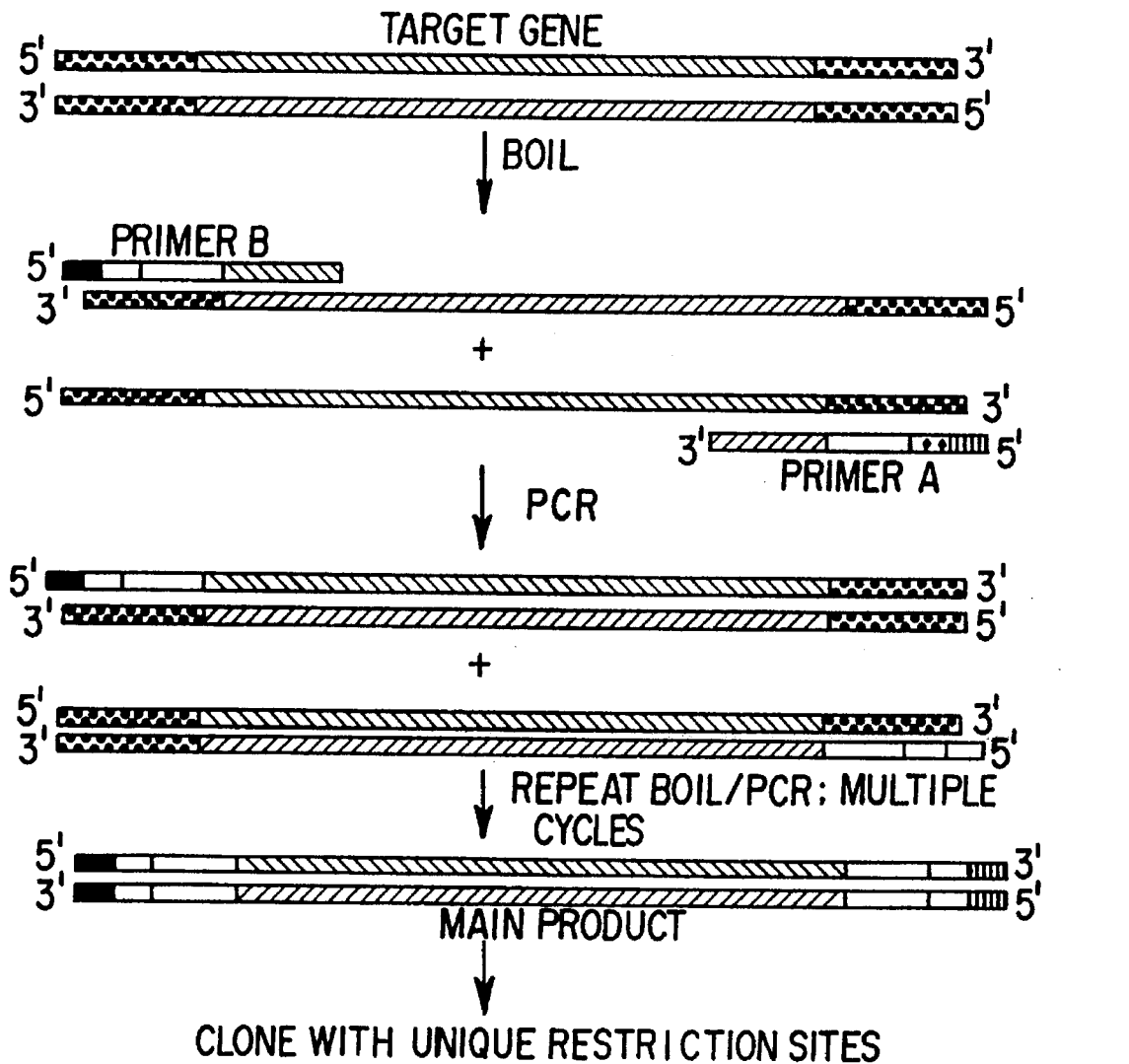

FIG. 10. Diagrammatic representation of a PCR-directed mutagenesis method which can be used to replace viral coding sequences within viral gene segments.

Figures 11A, 11B:
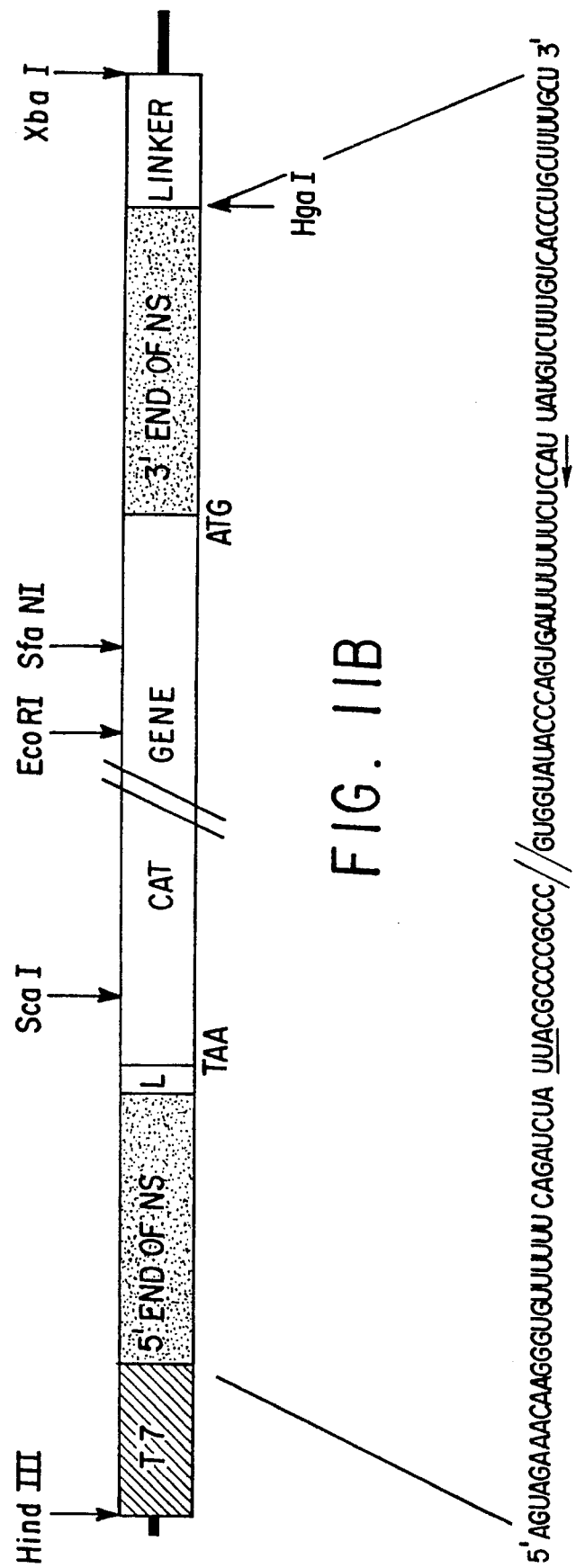

FIG. 11A–B (A). Diagrammatic representation of relevant portions of pIVCAT1. The various domains are labeled and are, from left to right; a truncated T7 promoter; the 5' nontranslated end of influenza A/PR/8/34 virus segment 8 (22 nucleotides); 8 nucleotides of linker sequence; the entire CAT gene coding region (660 nucleotides) the entire 3' nontranslated end of influenza A/PR/8/34 virus segment 8 (26 nucleotides); and linker sequence containing the HgaI restriction enzyme site. Relevant restriction enzyme sites and start and stop sites for the CAT gene are indicated. (B) The 716 base RNA product obtained following HgaI digestion and transcription of pIVACAT1 by T7 RNA polymerase. Influenza viral sequences are indicated by bold letters, CAT gene sequences by plain letters, and linker sequences by italics. The triplets—in antisense orientation—representing the initiation and termination codons of the CAT gene are indicated by arrow and underline, respectively.

Figure 12:
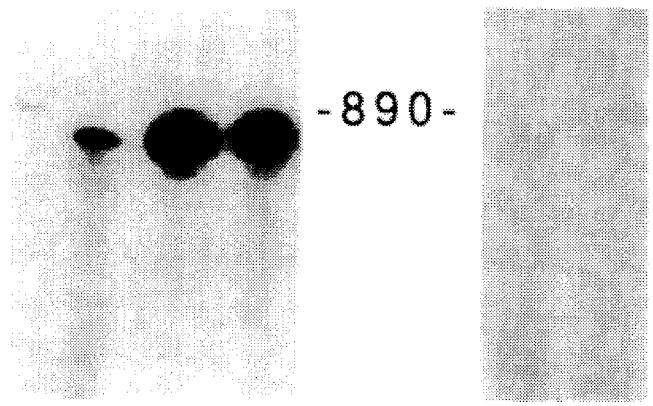

FIG. 12. RNA products of T7 polymerase transcription and in vitro influenza virus polymerase transcription. Lanes 1–4: polyacrylamide gel analysis of radiolabeled T7 polymerase transcripts from pIVACAT1, and pHgaNS. Lanes 5 and 6: Polyacrylamide gel analysis of the radiolabeled products of in vitro transcription by purified influenza A polymerase protein using unlabeled 1VACAT1RNA and HgaNS RNA templates. Lane 1: HgaNS RNA of 80 nt. Lanes 2–4: different preparations of IVACAT1 RNA. Lane 5: viral polymerase transcript of IVACAT1 RNA. Lane 6: viral polymerase transcript of HgaNS RNA.

Figure 13:
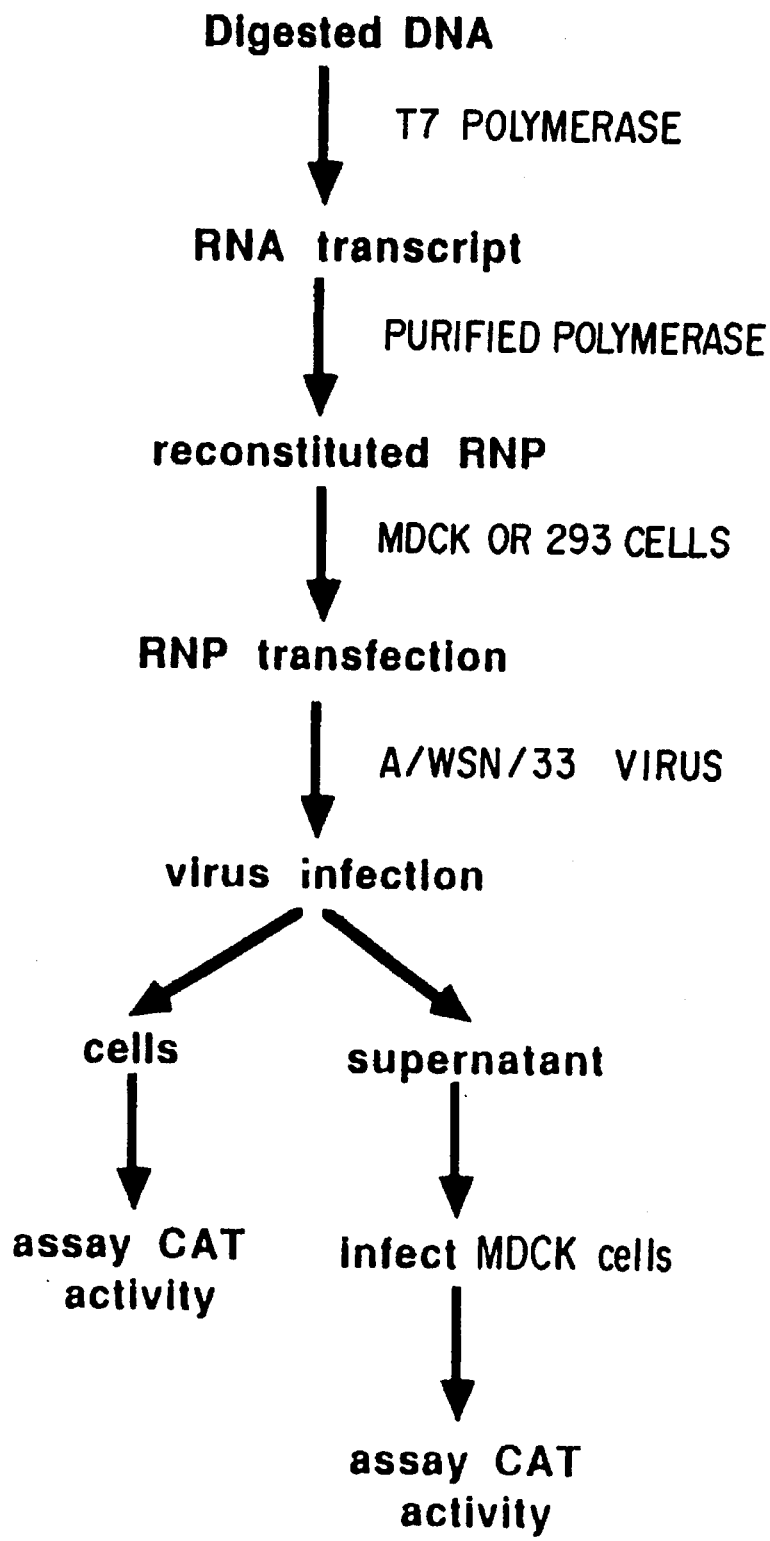

FIG. 13. Schematic of the RNP-transfection and passaging experiments.

Figure 14A:
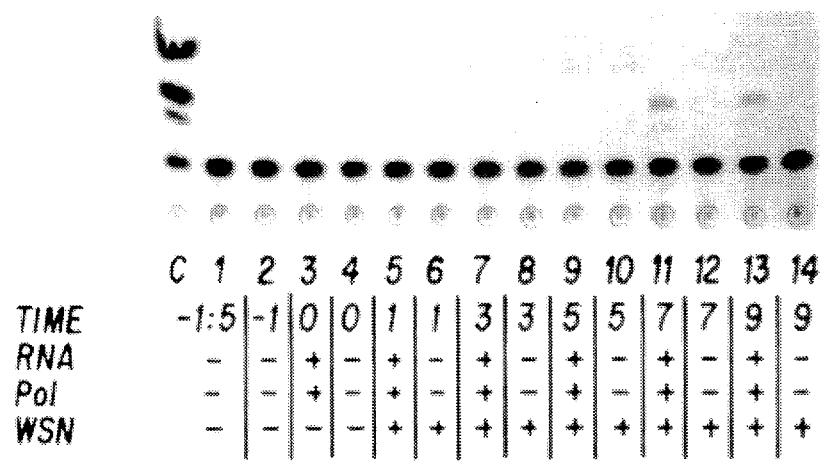
Figure 14B:
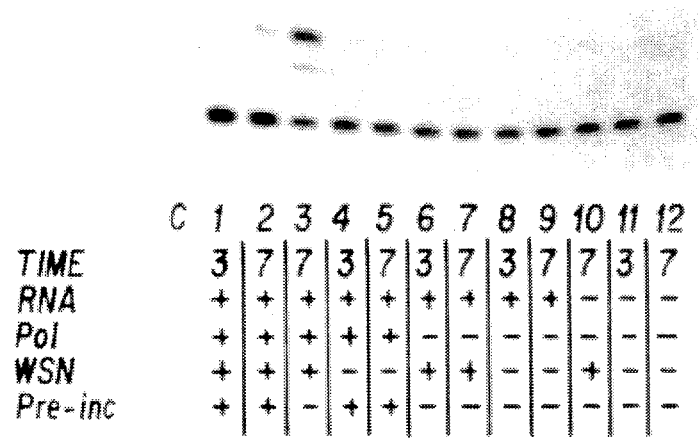
Figure 14C:
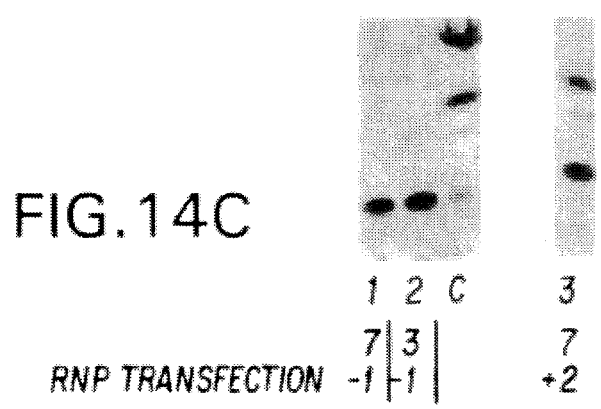

FIG. 14A–C. CAT assays of cells RNP-transfected with IVACAT1 RNA. (A) Time course of RNP-transfection in 293 cells. Cells were transfected at −1 hour with the recombinant RNP and infected with virus at 0 hour. Cells were harvested at the indicated time points and assayed for CAT activity. (B) Requirements for RNP-transfection of 293 cells Paramaeters of the reaction mixtures were as indicated. (C) RNP-transfection of MDCK cells. MDCK cells were transfected with IVACAT1 RNA-polymerase at either −1 hour or +2 hours relative to virus infection. Cells were harvested and CAT activity assayed at the indicated times. Components/conditions of the reaction were as indicated. "Time" indicates the time point of harvesting the cells. T=0 marks the time of addition of helper virus. "RNA" represents the IVACAT1 RNA. "Pol" is the purified influenza A/PR/8/34 polymerase protein complex. "WSN" indicates the influenza A/WSN/33 helper virus. "Pre-Inc." indicates preincubation of RNA and polymerase in transcription buffer at 30° C. for 30 min. "RNP transfection" indicates the time of RNP transfection relative to virus infection. "±" indicate presence or absence of the particular component/feature. "C" indicates control assays using commercially available CAT enzyme (Boehringer-Mannheim).

Figure 15:
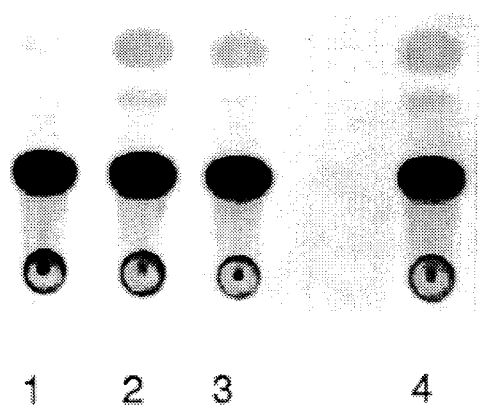

FIG. 15. CAT activity in MDCK cells infected with recombinant virus. Supernatant from RNP-transfected and helper virus-infected MDCK cells was used to infect fresh MDCK cells. The inoculum was removed 1 hour after infection, cells were harvested 11 hours later and CAT activity was assayed. Lane 1: extract of cells infected with helper virus only. Lane 2: extract of cells infected with 100 μl of supernatant from RNP-transfected and helper virus-infected MDCK cells. Lane 3: Supernatant (80 μl) of cells from lane 2. Lane 4: Same as lane 2 except that helper virus (MOI 4) was added to inoculum. In contrast to experiments shown in FIG. 4, the assays contained 20 μl of $^{14}C$ chloramphenicol.

Figure 16:
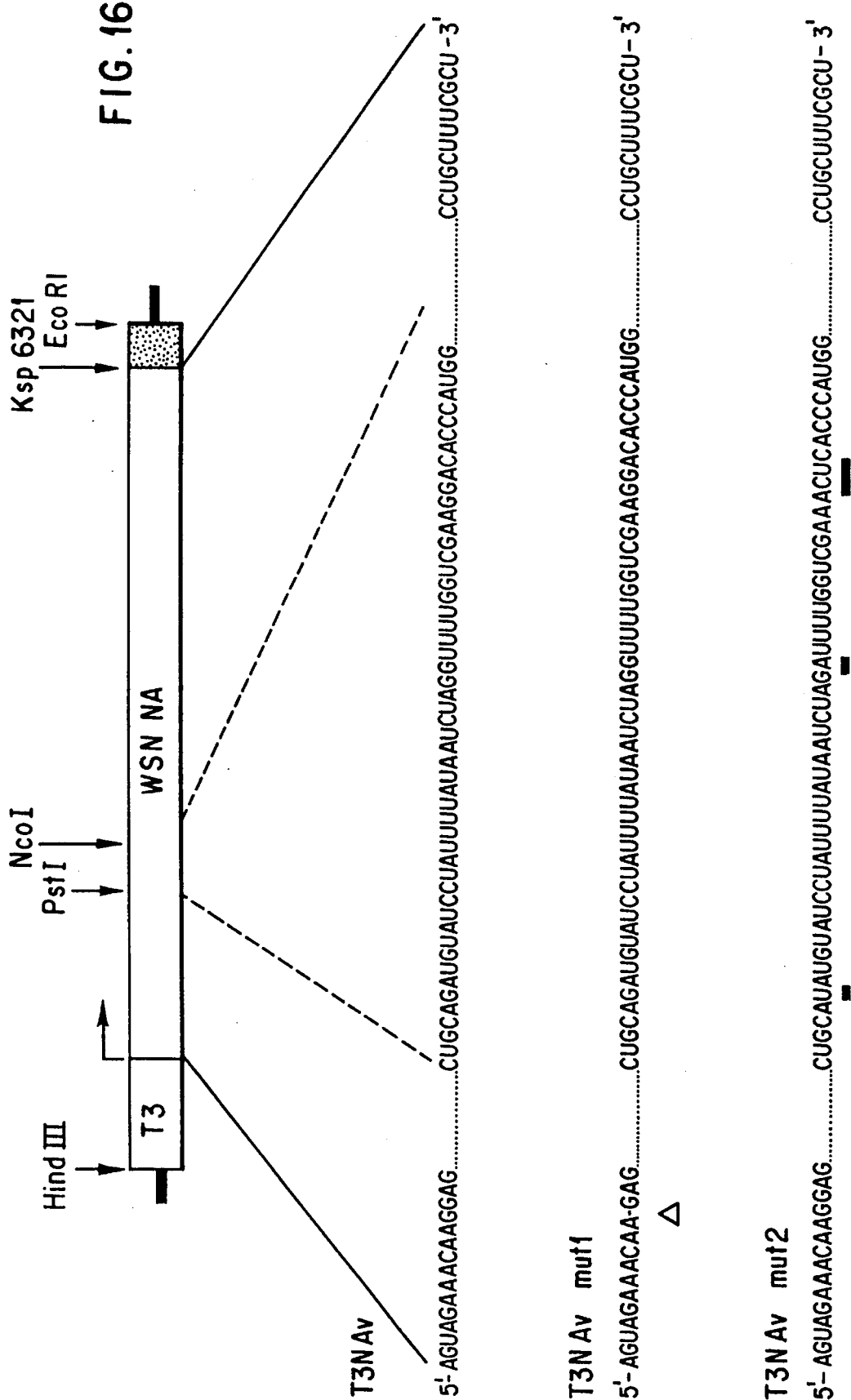

FIG. 16 Diagram of relevant portions of the Deuraminidase (NA) gene contained in plasmids used for transfection experiments. The pUC19 derived plasmid pT3NAv contains the influenza A/WSN/33 virus NA gene and a truncated promoter specifically recognized by bacteriophage T3 RNA polymerase. The T3 promoter used is truncated such that the initial transcribed nucleotide (an adenine) corresponds to the 5' adenine of the WSN NA gene. At the 3' end of the cDNA copy of the NA gene, a Ksp632I restriction enzyme site was inserted such that the cleavage site occurs directly after the 3' end of the NA gene sequence. A 1409 nucleotide long transcript was obtained following Ksp632I digestion and transcription by T3 RNA polymerase of PT3NAv (as described in Section 8.1, infra). The 15 5' terminal nucleotides, the 52 nucleotides corresponding to the region between the restriction endonuclease sites NcoI and PstI and the 12 3' terminal nucleotides are shown. The transcript of pT3NAv mut 1 is identical to that of pT3NAv except for a single deletion, eleven nucleotides downstream from the 5' end of the wild type RNA. The transcript of the pT3NAv mut 2 is identical to that of pT3NAv except for 5 mutations located in the central region (indicated by underline). These five mutations do not change the amino acid sequence in the open reading frame of the gene. The serine codon UCC at position 887–889 (plus sense RNA) was replaced with the serine codon AGU in the same frame. The numbering of nucleotides follows Hiti et al., 1982, J. Virol. 41:730–734.

Figure 17:
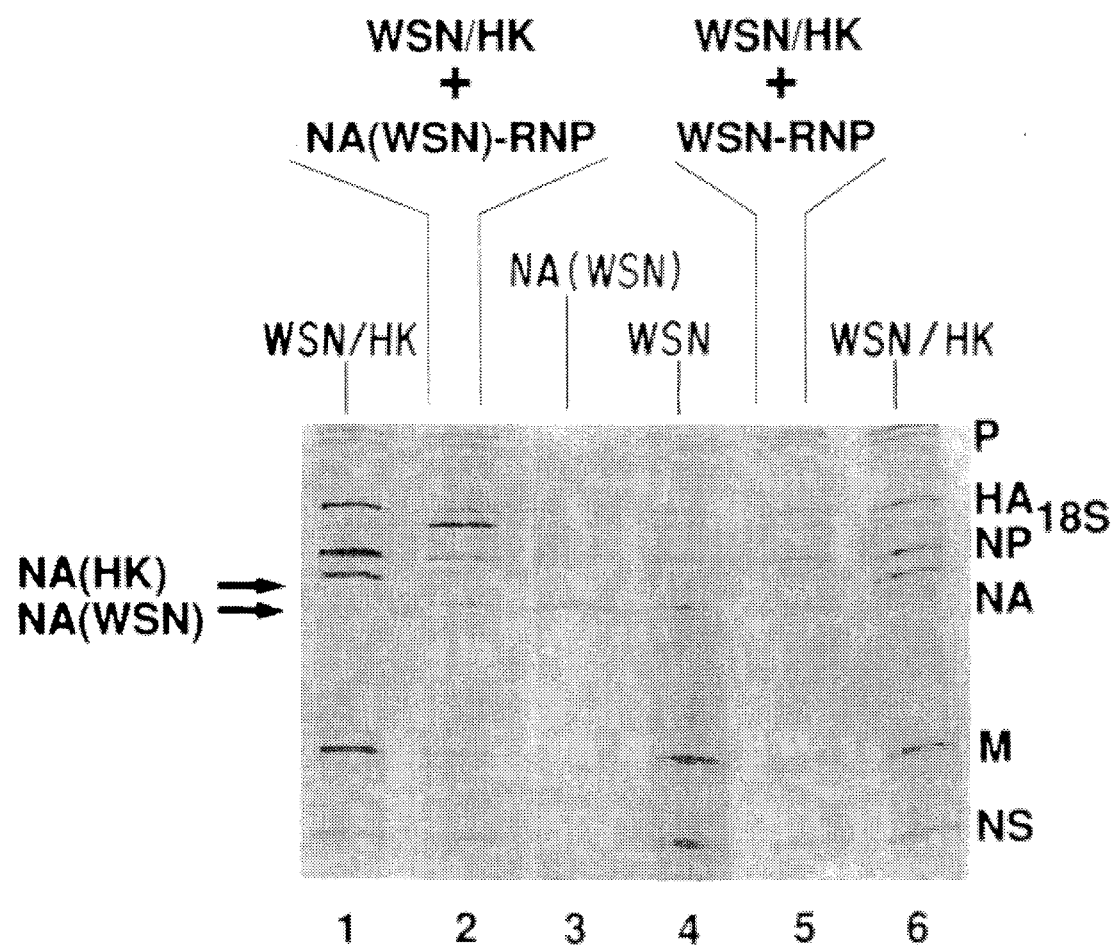

FIG. 17. Polyacrylamide gel electrophoresis of RNAs purified from rescued influenza viruses. RNA transcripts of pT3NAs (FIG. 16) of phenol-extracted RNA derived from influenza A/WSN/33 virus was mixed with purified polymerase preparations following the protocol described in Section 6.1.1, infra. These reconstituted RNPs were then transfected into MDBK cells which had been infected one hour earlier with WSN-HK helper virus. The medium, containing 28 μg/ml plasminogen, was harvested after 16 hours and virus was amplified and plaqued on MDBK cells in the absence of protease. Virus obtained from plaques was then further amplified in MDBK cells and RNA was phenol-extracted from purified virus preparations as described in Sections 6.1 et seq. and 7.1 et seq. RNAs were separated on 2.8% polyacrylamide-0.075% bisacrylamide gels containing 7.7M urea in TBE buffer and visualized by silverstaining as described in Section 6.1 et seq. Lanes 1 and 6: WSN-HK virus RNA. Lane 2: RNA of virus which was rescued from MDBK cells following RNP-transfection with pT3NAv derived NA RNA and infection with helper virus WSN-HK. Lane 3: NA RNA transcribed in vitro from pT3NAv. Lane 4: RNA of control WSN virus. Lane 5: RNA of virus which was rescued from MDBK cells following RNP-transfection with phenol-extracted WSN virus RNA and infection with helper virus WSN-HK.

Figure 18:
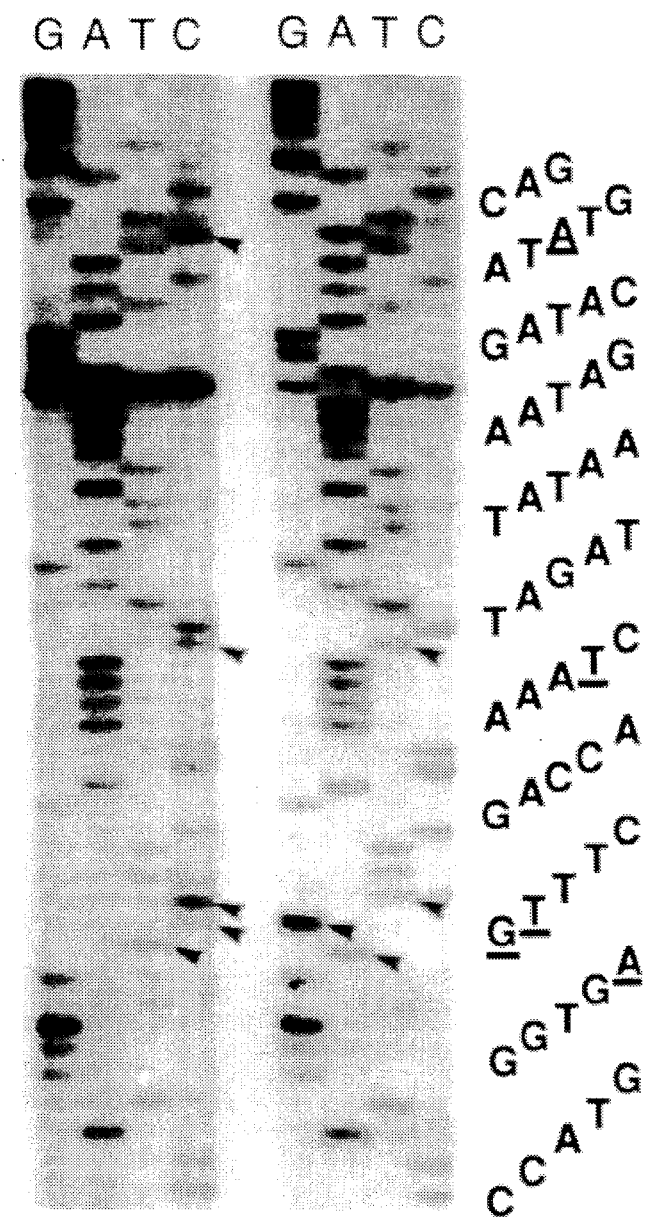

FIG. 18. Sequence analysis of RNA obtained from rescued influenza virus containing five site-specific mutations. Following infection with the WSN-HK helper virus, MDBK cells were RNP-transfected with T3NAv mut 2 RNA which was obtained by transcription from pT3NAv mut 2. Following overnight incubation in the presence of 28 μg/ml plasminogen, medium was used for propagation and plaquing on MDBK cells in the absence of protease. Virus from plaques was then amplified and RNA was obtained following phenol-extraction of purified virus. Rescue of the mutant NA gene into virus particles was verified through direct RNA sequencing using 5'-TACGAGGAAATGTTCCTGTTA-3' as primer (corresponding to position 800–819; Hiti et al., J. Virol. 41:730–734) and reverse transcriptase (Yamashita et al., 1988, Virol. 163:112–122). Sequences shown correspond to position 878–930 in the NA gene (Hiti et al., J. Virol. 41:730–734). The arrows and the underlined nucleotides indicate the changes in the mutant RNA compared to the wild type RNA. Left: Control RNA obtained from influenza A/WSN/33 virus. Right: RNA of mutant virus rescued from MDBK cells which were RNP-transfected with T3NAv mut 2 RNA and infected with helper virus WSN-HK.

Figure 19:
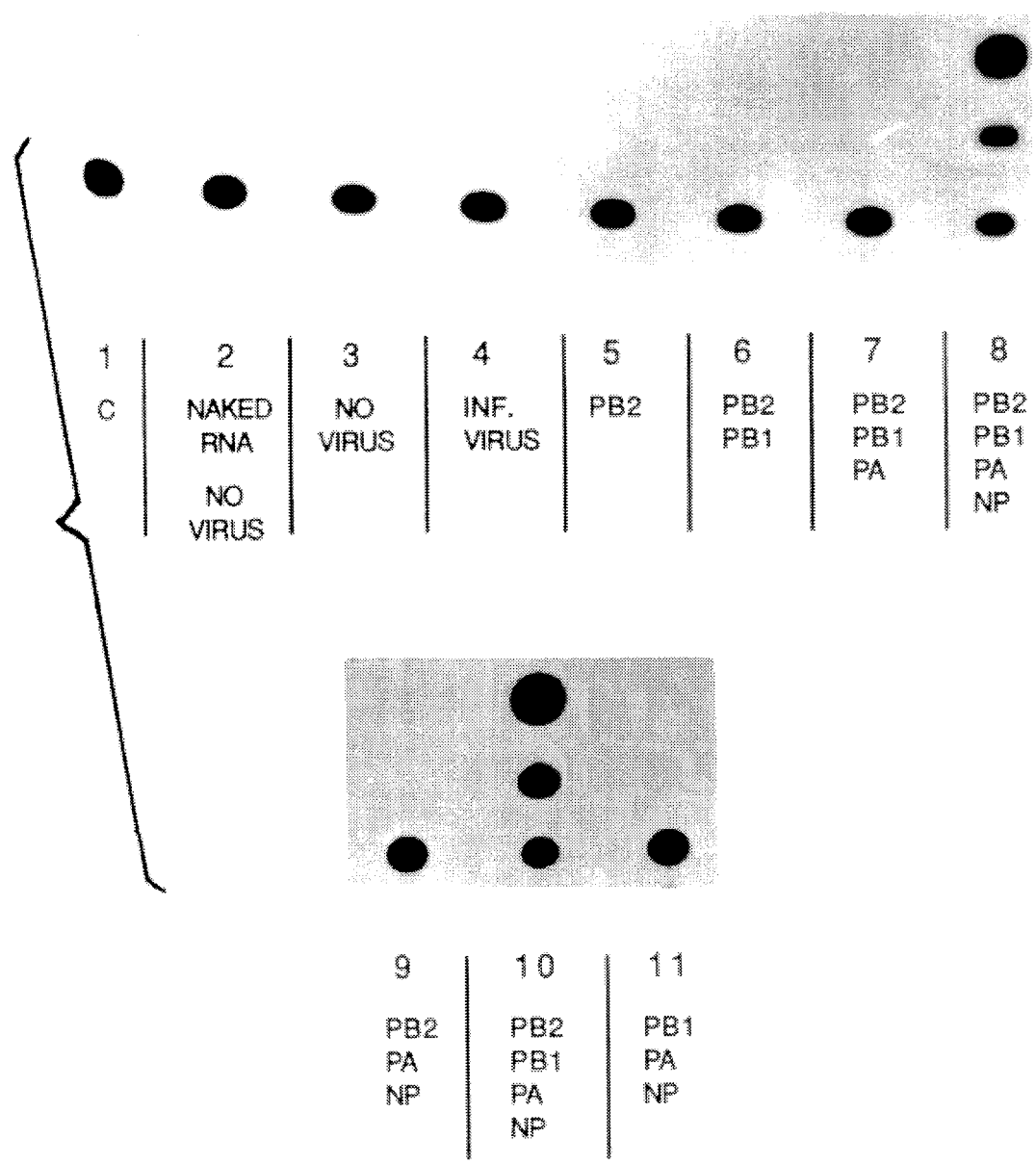

FIG. 19. CAT expression in vaccinia virus-infected/IVA-CAT-1 RNP transfected cells. Approximately 106 mouse C127 cells in 35 mm dishes were infected with mixtures of recombinant vaccinia viruses (Smith et al., 1986) at an M.O.I. of approximately 10 for each vector. After 1.5 hours, synthetic IVACAT-1 RNP was transfected into the virus-infected cells as described (Lutjyes et al., 1989). Cells were incubated overnight, harvested and assayed for CAT activity according to standard procedures (Gorman et al., 1982). The assays contained 0.05 uCl [$^{14}$C] chloramphenicol, 20 ul of 40 mM acetyl-CoA (Boehringer and 50 ul of cell extracts in 0.25M Tris buffer (pH 7.5). Incubation times were approximately 4 hours. The labels under the lane numbers indicate the treatment of cells. Lanes 1-control; 2-naked RNA transfection (no polymerase added), no helper virus infection; 3-RNP transfection, no helper virus; 4-RNP transfection, influenza virus as helper; Lanes 5–11-RNP transfection, vaccinia virus vectors as helper viruses express the indicated influenza virus proteins.

FIG. 20A–C. Test of various cell lines. A) Cells were infected with vaccinia vectors expressing the PB2, PB1 and PA proteins (Lanes 1,3,5,7) or the PB2, PB1, PA and NP proteins (Lanes 2,4,6,8), transfected with IVACAT-1 RNP and examined for CAT activity as described. Lanes 1,2: Maden-Darby Canine Kidney (MDCK) cell; 3,4: Hela cells, 5,6: 293 cells (Graham et al., 1977 J. gen. Virol 36: 59–72); 7,8 L cells. B) Cell line 3 PNP-4 was used as host cell. Shown under each lane is the influenza viral proteins expressed in each sample. C) 293 cells were infected with the four required vaccinia and transfected with synthetic RNP made using IVA-CAT-1 (lane 1) or IVA-CAT-2 (lane 2) RNA. After overnight incubation, cells were harvested and CAT assayss were performed.

5. DESCRIPTION OF THE INVENTION

This invention relates to the construction and use of recombinant negative strand viral RNA templates which may be used with viral RNA-directed RNA polymerase to express heterotogous gene products in appropriate host cells and/or to rescue the heterologous gene in virus particles. The RNA templates may be prepared by transcription of appropriate DNA sequences using a DNA-directed RNA polymerase such as bacteriophage T7, T3 or the Sp6 polymerase. Using influenza, for example, the DNA is constructed to encode the message-sense of the heterologous gene sequence flanked upstream of the ATG by the complement of the viral polymerase binding site/promoter of influenza, i.e., the complement of the 3'-terminus of a genome segment of influenza. For rescue in virus particles, it may be preferred to flank the heterologous coding sequence with the complement of both the 3'-terminus and the 5'-terminus of a genome segment of influenza. After transcription with a DNA-directed RNA polymerase, the resulting RNA template will encode the negative polarity of the heterologous gene sequence and will contain the vRNA terminal sequences that enable the viral RNA-directed RNA polymerase to recognize the template.

The recombinant negative sense RNA templates may be mixed with purified viral polymerase complex comprising viral RNA-directed RNA polymerase proteins (the P proteins) and nucleoprotein (NP) which may be isolated from RNP cores prepared from whole virus to form "recombinant RNPs" (rRNPs). These rRNPs are infectious and may be used to express the heterologous gene product in appropriate host cells or to rescue the heterologous gene in virus particles by cotransfection of host cells with the rRNPs and virus. Alternatively, the recombinant RNA templates may be used to transfect transformed cell lines that express the RNA-directed RNA polymerase proteins allowing for complementation.

The invention is demonstrated by way of working examples in which RNA transcripts of cloned DNA containing the coding region—in negative sense orientation—of the chloramphenicol acetyltransferase (CAT) gene, flanked by the the 22 5' terminal and the 26 3' terminal nucleotides of the influenza A/PR/8/34 virus NS RNA were mixed with isolated influenza A virus polymerase proteins. This reconstituted ribonucleoprotein (RNP) complex was transfected into MDCK (or 293) cells, which were infected with influenza virus. CAT activity was negligible before and soon after virus infection, but was demonstrable by seven hours post virus infection. When cell supernatant containing budded virus from this "rescue" experiment was used to infect a new monolayer of MDCK cells, CAT activity was also detected, suggesting that the RNA containing the recombinant CAT gene had been packaged into virus particles. These results demonstrate the successful use of recombinant negative strand viral RNA templates and purified RNA-dependent RNA polymerase to reconstitute recombinant influenza virus RNP. Furthermore, the data suggest that the 22 5' terminal and the 26 3' terminal sequences of the influenza A virus RNA are sufficient to provide the signals for RNA tanscription, RNA replication and for packaging of RNA into influenza virus particles.

Using this methodology we also demonstrated the rescue of synthetic RNAs, derived from appropriate recombinant plasmid DNAs, into stable and infectious influenza viruses. In particular, RNA corresponding to the neuraminidase (NA) gene of influenza A/WSN/33 virus (WSN) was transcribed in vitro from plasmid DNA and, following the addition of purified influenza virus polymerase complex, was transfected into MDBK cells. Superinfection with helper virus lacking the WSN NA gene resulted in the release of virus containing the WSN NA gene. We then introduced five point mutations into the WSN NA gene by cassette mutagenesis of the plasmid DNA. Sequence analysis of the rescued virus revealed that the genome contained all five mutations present in the mutated plasmid. This technology can be used to create viruses with site-specific mutations so that influenza viruses with defined biological properties may be engineered.

The ability to reconstitute RNP's in vitro allows the design of novel chimeric influenza viruses which express foreign genes. One way to achieve this goal involves modifying existing influenza virus genes. For example, the HA gene may be modified to contain foreign sequences in its external domains. Where the heterologous sequence are epitopes or antigens of pathogens, these chimeric viruses may be used to induce a protective immune response against the disease agent from which these determinants are derived. In addition to modifying genes coding for surface proteins, genes coding for nonsurface proteins may be altered. The latter genes have been shown to be associated with most of the important cellular immune responses in the influenza virus system (Townsend et al., 1985, Cell 42:475–482). Thus, the inclusion of a foreign determinant in the NP or the NS gene of an influenza virus may—following infection—induce an effective cellular immune response against this determinant. Such an approach may be particularly helpful in situations in which protective immunity heavily depends on the induction of cellular immune responses (e.g., malaria, etc.).

Another approach which would permit the expression of foreign proteins (or domains of such proteins) via chimeric influenza viruses concerns the introduction of complete heterologous genes into the virus. Influenza virus preparations with more than eight RNA segments have previously been described (Nayak, D. et al. in Genetics of Influenza Virus, P. Palese and D. W. Kingsbury, eds., Springer-Verlag, Vienna, pp. 255–279). Thus, chimeric influenza viruses with nine or more RNA segments may be viable, and correct packaging of such chimeric viruses may readily occur.

The invention may be divided into the following stages solely for the purpose of description and not by way of limitation: (a) construction of recombinant RNA templates; (b) expression of heterologous gene products using the recombinant RNA templates; and (c) rescue of the heterologous gene in recombinant virus particles. For clarity of discussion, the invention is described in the subsections below using influenza. Any strain of influenza (e.g., A, B, C) may be utilized. However, the principles may be analagously applied to construct other negative strand RNA virus templates and chimeric viruses including, but not limited to paramyxoviruses, such as parainfluenza viruses, measles viruses, respiratory syncytial virus; bunyaviruses; arena viruses; etc. A particularly interesting virus system that can be used in accordance with the invention are the orthomyxo-like insect virus called Dhori (Fuller, 1987, Virology 160:81–87).

5.1. CONSTRUCTION OF THE RECOMBINANT RNA TEMPLATES

Heterologous gene coding sequences flanked by the complement of the viral polymerase binding site/promoter, e.g., the complement of 3'-influenza virus terminus, or the complements of both the 3'- and 5'-influenza virus termini may be constructed using techniques known in the art. Recombinant DNA molecules containing these hybrid sequences can be cloned and transcribed by a DNA-directed RNA polymerase, such as bacteriophage T7, T3 or the Sp6 polymerase and the like, to produce the recombinant RNA templates which possess the appropriate viral sequences that allow for viral polymerase recognition and activity.

One approach for constructing these hybrid molecules is to insert the heterologous coding sequence into a DNA complement of an influenza virus genomic segment so that the heterologous sequence is flanked by the viral sequences required for viral polymerase activity; i.e., the viral polymerase binding site/promoter, hereinafter referred to as the viral polymerase binding site. In an alternative approach, oligonucleotides encoding the vital polymerase binding site, e.g., the complement of the 3'-terminus or both termini of the virus genomic segments can be ligated to the heterologous coding sequence to construct the hybrid molecule. The placement of a foreign gene or segment of a foreign gene within a target sequence was formerly dictated by the presence of appropriate restriction enzyme sites within the target sequence. However, recent advances in molecular biology have lessened this problem greatly. Restriction enzyme sites can readily be placed anywhere within a target sequence through the use of site-directed mutagenesis (e.g., see, for example, the techniques described by Kunkel, 1985, Proc. Natl. Acad. Sci. U.S.A. 82;488). Variations in polymerase chain reaction (PCR) technology, described infra, also allow for the specific insertion of sequences (i.e., restriction enzyme sites) and allow for the facile construction of hybrid molecules. Alternatively, PCR reactions could be used to prepare recombinant templates without the need of cloning. For example, PCR reactions could be used to prepare double-stranded DNA molecules containing a DNA-directed RNA polymerase promoter (e.g., bacteriophase T3, T7 or Sp6) and the hybrid sequence containing the heterologous gene and the influenza viral polymerase binding site. RNA templates could then be transcribed directly from this recombinant DNA. In yet another embodiment, the recombinant RNA templates may be prepared by ligating RNAs specifying the negative polarity of the heterologous gene and the viral polymerase binding site using an RNA ligase. Sequence requirements for viral polymerase activity and constructs which may be used in accordance with the invention are described in the subsections below.

5.1.1. THE VIRAL 3'-TERMINUS IS REQUIRED FOR POLYMERASE ACTIVITY

The experiments described in Section 6 et seq., infra, are the first to define promoter sequences for a polymerase of a negative-sense RNA virus, and it was found that the specificity lies in the 3' terminal 15 nucleotides. These viral polymerase binding site sequences, as well as functionally equivalent sequences may be used in accordance with the invention. For example, functionally equivalent sequences containing substitions, insertions, deletions, additions or inversions which exhibit similar activity may be utilized. The RNA synthesis by the viral polymerase described infra is a model for specific recognition and elongation by the influenza viral polymerase for the following reasons: (a) the polymerase has high activity when primed with ApG, a feature unique to influenza viral polymerase; (b) it has optimal activity at temperature and ionic conditions previously shown to be effective for the viral RNPs; (c) the polymerase is specific for influenza viral sequences on the model RNA templates; (d) the polymerase is active in the cap-endonuclease primed RNA synthesis which is the hallmark of the influenza viral polymerase; (e) recognition of cap donor RNA is specific to cap 1 structures; and (f) genomic RNA segments are specifically copied.

5.1.2. A TERMINAL PANHANDLE IS NOT REQUIRED FOR OPTIMAL RECOGNITION AND SYNTHESIS BY THE VIRAL POLYMERASE

We had previously shown that the influenza viral segment RNAs base-pair at their termini to form panhandle structures. This was achieved by two methods. A cross-linking reagent derivative of psoralen covalently bound the termini of each segment in intact virus or in RNPs from infected cells (Hsu et al., 1987, Proc. Natl. Acad. Sci. U.S.A. 84: 8140–8144). The treated RNA was seen by electron microscopy to be circular, by virtue of the crosslinked termini. Similarly, the RNA termini in RNPs were found to be sensitive to ribonuclease V1, which recognizes and cleaves double-stranded RNA, and the viral polymerase was found to be bound to both termini in the panhandle conformation (Honda, et al., 1988, J. Biochem. 104: 1021–1026). In these studies the panhandle structure of the genomic RNA was shown to exist, and it was inferred to play a role in polymerase recognition. Although the template RNAs used in the examples described, were originally prepared to reveal panhandle-specific protein binding, it was found that the terminal panhandle had no obvious role in the polymerase reactions studied herein.

5.1.3. THE RNA POLYMERASE PREPARATION SPECIFICALLY COPIES NEGATIVE SENSE TEMPLATES

The viral polymerase was shown to synthesize RNA with optimal efficiency if the template had the "wild-type" negative sense 3' terminus. It was shown that RNAs of unrelated sequence were not copied, and that those with extra polylinker sequences on the 3' end were much less efficiently copied. A DNA of the correct sequence was similarly unsuitable as a template. The reaction was highly specific since the M-wt template was replicated only at very low levels. Even though our source of polymerase was intact virus, this finding was very surprising since it had never been suggested that the polymerase which recognizes the viral sense RNA would not efficiently copy the plus sense strand. Studies are underway to examine the specificity of the polymerase purified from infected cells at times post infection when the complementary RNA is copied into genomic templates. The present data support a model whereby the viral polymerase which copies vRNA is functionally different from that which synthesizes vRNA from cRNA by virtue of their promoter recognition. It is possible that by regulated modification of the polymerase in infected cells it then becomes capable of recognizing the 3' terminus of plus sense RNA. By analyzing promoter mutants we investigated the fine specificity of the reaction and found that the only single mutation which generated a significantly lower level of synthesis was that of V-A$_3$ RNA. Furthermore, combinations of two or more point changes in positions 3, 5, 8 and 10 greatly lowered synthesis levels.

5.1.4. INSERTION OF THE HETEROLOGOUS GENE SEQUENCE INTO THE PB2, PB1, PA OR NP GENE SEGMENTS

The gene segments coding for the PB2, PB1, PA and NP proteins contain a single open reading frame with 24–45 untranslated nucleotides at their 5'-end, and 22–57 untranslated nucleotides at their 3'-end. Insertion of a foreign gene sequence into any of these segments could be accomplished by either a complete replacement of the viral coding region with the foreign gene or by a partial replacement. Complete replacement would probably best be accomplished through the use of PCR-directed mutagenesis. The principle of this mutagenesis method is illustrated in FIG. 10. Briefly, PCR-primer A would contain, from 5' to 3', a unique restriction enzyme site, such as a class IIS restriction enzyme site (i.e., a "shifter" enzyme; that recognizes a specific sequence but cleaves the DNA either upstream or downstream of that sequence); the entire 3' untranslated region of the influenza gene segment; and a stretch of nucleotides complementary to the carboxy-terminus coding portion of the foreign gene product. PCR-primer B would contain from the 5' to 3' end: a unique restriction enzyme site; a truncated but active phage polymerase sequence; the complement of the entire 5' untranslated region of the influenza gene segment (with respect to the negative sense vRNA); and a stretch of nucleotides corresponding to the 5' coding portion of the foreign gene. After a PCR reaction using these primers with a cloned copy of the foreign gene, the product may be excised and cloned using the unique restriction sites. Digestion with the class IIS enzyme and transcription with the purified phage polymerase would generate an RNA molecule containing the exact untranslated ends of the influenza viral gene segment with a foreign gene insertion. Such a construction is described for the chloramphenicol acetyltransferase (CAT) gene used in the examples described in Section 7 infra. In an alernate embodiment, PCR-primed reactions could be used to prepare double-stranded DNA containing the bacteriophage promoter sequence, and the hybrid gene sequence so that RNA templates can be transcribed directly without cloning.

Depending on the integrity of the foreign gene product and the purpose of the construction, it may be desirable to construct hybrid sequences that will direct the expression of fusion proteins. For example, the four influenza virus proteins, PB2, PB1, PA or NP are polymerase proteins which are directed to the nucleus of the infected cell through specific sequences present in the protein. For the NP this amino acid sequence has been found to be (single letter code) QLVW-MACNSAAFEDLRVLS (Davey et al., 1985, Cell 40:667–675). Therefore, if it is desired to direct the foreign gene product to the nucleus (if by itself it would not ordinarily do so) the hybrid protein should be engineered to contain a domain which directs it there. This domain could be of influenza viral origin, but not necessarily so. Hybrid proteins can also be made from non-viral sources, as long as they contain the necessary sequences for replication by influenza virus (3' untranslated region, etc.).

As another example, certain antigenic regions of the viral gene products may be substituted with foreign sequences. Townsend et al., (1985, Cell 42:475–482), identified an epitope within the NP molecule which is able to elicit a vigorous CTL (cytotoxic T cell) response. This epitope spans residues 147–161 of the NP protein and consists of the amino acids TYQRTRQLVRLTGMDP. Substituting a short foreign epitope in place of this NP squence may elicit a strong cellular immune response against the intact foreign antigen. Conversely, expression of a foreign gene product containing this 15 amino acid region may also help induce a strong cellular immune response against the foreign protein.

5.1.5. INSERTION OF THE HETEROLOGOUS GENE SEQUENCE INTO THE HA OR NA GENE SEGMENTS

The HA and NA proteins, coded for by separate gene segments, are the major surface glycoproteins of the virus. Consequently, these proteins are the major targets for the humoral immune response after infection. They have been the most widely-studied of all the influenza viral proteins as the three-dimensional structures of both these proteins have been solved.

The three-dimensional structure of the H3 hemagglutinin along with sequence information on large numbers of variants has allowed for the elucidation of the antigenic sites on the HA molecule (Webster et al., 1983, In Genetics Of Influenza Virus, P. Palese and D. W. Kingsbury, eds., Springer-Verlag, Vienna, pp. 127–160). These sites fall into four discrete non-overlapping regions on the surface of the HA. These regions are highly variable and have also been shown to be able to accept insertions and deletions. Therefore, substitution of these sites within HA (e.g., site A; amino acids 122–147 of the A/HK/68 HA) with a portion of a foreign protein may provide for a vigorous humoral response against this foreign peptide. In a different approach, the foreign peptide sequence may be inserted within the antigenic site without deleting any viral sequences. Expression products of such constructs may be useful in vaccines against the foreign antigen, and may indeed circumvent a problem discussed earlier, that of propagation of the recombinant virus in the vaccinated host. An intact HA molecule with a substitution only in antigenic sites may allow for HA function and thus allow for the construction of a viable virus. Therefore, this virus can be grown without the need for additional helper functions. Of course, the virus should be attenuated in other ways to avoid any danger of accidental escape.

Other hybrid constructions may be made to express proteins on the cell surface or enable them to be released from the cell. As a surface glycoprotein, the HA has an amino-terminal cleavable signal sequence necessary for transport to the cell surface, and a carboxy-terminal sequence necessary for membrane anchoring. In order to express an intact foreign protein on the cell surface it may be necessary to use these HA signals to create a hybrid protein. Alternatively, if only the transport signals are present and the membrane anchoring domain is absent, the protein may be excreted out of the cell.

In the case of the NA protein, the three-dimensional structure is known but the antigenic sites are spread out over the surface of the molecule and are overlapping. This indicates that if a sequence is inserted within the NA molecule and it is expressed on the outside surface of the NA it will be immunogenic. Additionally, as a surface glycoprotein, the NA exhibits two striking differences from the HA protein. Firstly, the NA does not contain a cleavable signal sequence; in fact, the amino-terminal signal sequence acts as a membrane anchoring domain. The consequence of this, and the second difference between the NA and HA, is that the NA is orientated with the amino-terminus in the membrane while the HA is orientated with the carboxy-terminus in the membrane. Therefore it may be advantageous in some cases to construct a hybrid NA protein, since the fusion protein will be orientated opposite of a HA-fusion hybrid.

5.1.6. INSERTION OF THE HETEROLOGOUS GENE INTO THE NS AND M GENE SEGMENTS

The unique property of the NS and M segments as compared to the other six gene segments of influenza virus is that these segments code for at least two protein products. In each case, one protein is coded for by an mRNA which is co-linear with genomic RNA while the other protein is coded for by a spliced message. However, since the splice donor site occurs within the coding region for the co-linear transcript, the NS1 and NS2 proteins have an identical 10 amino acid amino terminus while M1 and M2 have an idential 14 amino acid amino terminus.

As a result of this unique structure, recombinant viruses may be constructed so as to replace one gene product within the segment while leaving the second product intact. For instance, replacement of the bulk of the NS2 or M2 coding region with a foreign gene product (keeping the splice acceptor site) could result in the expression of an intact NS1 or M1 protein and a fusion protein instead of NS2 or M2. Alternatively, a foreign gene may be inserted within the NS gene segment without affecting either NS1 or NS2 expression. Although most NS genes contain a substantial overlap of NS1 and NS2 reading frames, certain natural NS genes do not. We have analyzed the NS gene segment from A/Ty/Or/71 virus (Norton et al., 1987, Virology 156:204–213) and found that in this particular gene, the NS1 protein terminates at nucleotide position 409 of the NS gene segment while the splice acceptor site for the NS2 is at nucleotide position 528. Therefore, a foreign gene could be placed between the termination codon of the NS1 coding region and the splice acceptor site of the NS2 coding region without affecting either protein. It may be necessary to include a splice acceptor site at the 5' end of the foreign gene sequence to ensure protein production (this would encode a hybrid protein containing the amino-terminus of NS1). In this way, the recombinant virus should not be defective and should be able to be propagated without need of helper functions.

Although the influenza virus genome consists of eight functional gene segments it is unknown how many actual segments a virus packages. It has been suggested that influenza can package more than eight segments, and possibly up to 12 (Lamb and Choppin, 1983, Ann. Rev. Biochem. 52:467–506). This would allow for easier propagation of recombinant virus in that "ninth" gene segment could be designed to express the foreign gene product. Although this "ninth" segment may be incorporated into some viruses, it would soon be lost during virus growth unless some selection is supplied. This can be accomplished by "uncoupling" the NS or M gene segment. The NS2 coding portion could be removed from the NS gene segment and placed on the gene segment coding for the foreign protein (along with appropriate splicing signals). Alternatively, a bicistronic mRNA could be constructed to permit internal initiation to "unsplice" these viral sequences; for example, using the sequences described by Pelletier et al., 1988, Nature 334:320–325. The resulting recombinant virus with the "uncoupled" NS or M gene would be able to propagate on its own and also would necessarily have to package the "ninth" gene segment, thus ensuring expression of the foreign gene.

5.2. EXPRESSION OF HETEROLOGOUS GENE PRODUCTS USING RECOMBINANT RNA TEMPLATE

The recombinant templates prepared as described above can be used in a variety of ways to express the heterologous gene products in appropriate host cells or to create chimeric viruses that express the heterologous gene products. In one embodiment, the recombinant template can be combined with viral polymerase complex purified as described in Section 6, infra, to produce rRNPs which are infectious. Alternatively, the recombinant template may be mixed with viral polymerase complex prepared using recombinant DNA methods (e.g. see Kingsbury et al., 1987, Virology 156:396–403). Such rRNPs, when used to transfect appropriate host cells, may direct the expression of the heterologous gene product at high levels. Host cell systems which provide for high levels of expression include continuous cell lines that supply viral functions such as cell lines superinfected with influenza, cell lines engineered to complement influenza viral functions, etc.

In an alternate embodiment of the invention, the recombinant templates or the rRNPs may be used to transfect cell lines that express the viral polymerase proteins in order to achieve expression of the heterologous gene product. To this end, transformed cell lines that express all three polymerase proteins such as 3P-38 and 3P-133 (Krystal et al., 1986, Proc. Natl. Acad. Sci. U.S.A. 83:2709–2713) may be utilized as appropriate host cells. Host cells may be similarly engineered to provide other viral functions or additional functions such as NP.

5.2.1. PURIFICATION OF THE VIRAL POLYMERASE

The viral polymerase proteins used to produce the rRNPs may be purified from dissociated RNP cores isolated from whole virus. In general, RNP cores may be prepared using standard methods (Plotch et al., 1981, Cell 23:847–858; Rochavansky, 1976, Virology 73: 327–338). The pooled RNP cores may then be centrifuged on a second gradient of CsCl (1.5–3.0M) and glycerol (30%–45%) as described by Honda et al., 1988, J. Biochem. 104: 1021–1026. The active viral polymerase fractions may be isolated from top of the gradient, i.e. in the region of the gradient correlating with 1.5 to 2.0M CsC1 and corresponding to the fraction Honda et al. identified as "NP". Surprisingly, this fraction contains all the viral polymerase proteins required for the active complex. Moreover, the P proteins which may be recovered from the bottom of the gradient are not required, and indeed do not provide for the transcription of full length viral RNA. Thus, it appears that the so-called "NP" fraction contains, in addition to NP, the active forms of the PB2, PB1, and PA proteins.

5.2.2. HIGH CONCENTRATIONS OF POLYMERASE ARE REQUIRED FOR CAP-PRIMED RNA SYNTHESIS

High concentrations of viral polymerase complex are able to catalyze this virus-specific cap-endonuclease primed transcription. Under the conditions specified in Section 6 infra, about 50 ng NP with 200 pg of the three P proteins were found to react optimally with 5 to 10 ng RNA reaction. The observation has been that although the NP selectively encapsidates influenza vRNA or cRNA in vivo, the NP will bind to RNA nonspecifically in vitro (Kingsbury, et al., 1987, Virology 156: 396–403; Scholtissek and Becht, 1971, J. Gen. Virol. 10: 11–16). Presumably, in order for the viral polymerase to recognize the viral template RNAs in our in vitro reaction, they have to be encapsidated by the NP. Therefore, the addition of a capped mRNA primer would essentially compete with the template RNA for binding of NP. Since the dinucleotide ApG would not be expected to bind NP, the low concentration polymerase was able to use only the short templates with ApG. Supporting this hypothesis is the observation that the higher concentration polymerase preparation is inhibited through the addition of progressively higher amounts of either template RNA or any non-specific RNA. It should also be noted that the unusual specificity for the m7GpppXm cap 1 structure previously shown with viral RNPs was also found with the reconstituted RNPs.

5.2.3. GENOMIC LENGTH RNA TEMPLATES ARE EFFICIENTLY COPIED

Plasmid-derived RNA identical to segment 8 of the A/WSN/33 virus was specifically copied by the polymerase (using the PCR method described in FIG. 10). In reactions using RNA extracted from virus, all eight segments were copied, although the HA gene was copied at a lower level. The background in these reactions was decreased in comparison to the 30 to 53 nt templates, probably since the contaminating RNAs in the polymerase preparation were predominantly defective RNAs of small size. Recombinant templates encoding foreign genes transcribed in this system may be used to rescue the engineered gene in a virus particle.

5.3. PREPARATION OF CHIMERIC NEGATIVE STRAND RNA VIRUS

In order to prepare chimeric virus, reconstituted RNPs containing modified influenza virus. RNAs or RNA coding for foreign proteins may be used to transfect cells which are also infected with a "parent" influenza virus. Alternatively, the reconstituted RNP preparations may be mixed with the RNPs of wild type parent virus and used for transfection directly. Following reassortment, the novel viruses may be isolated and their genomes be identified through hybridization analysis. In additional approaches described herein for the production of infectious chimeric virus, rRNPs may be replicated in host cell systems that express the influenza viral polymerase proteins (e.g., in virus/host cell expression systems; transformed cell lines engineered to express the polymerase proteins, etc.), so that infectious chimeric virus are rescued; in this instance, helper virus need not be utilized since this function is provided by the viral polymerase proteins expressed. In a particularly desirable approach, cells infected with rRNPs engineered for all eight influenza virus segments may result in the production of infectious chimeric virus which contain the desired genotype; thus eliminating the need for a selection system.

Theoretically, one can replace any one of the eight gene segments, or part of any one of the eight segments with the foreign sequence. However, a necessary part of this equation is the ability to propagate the defective virus (defective because a normal viral gene product is missing or altered). A number of possible approaches exist to circumvent this problem. We have shown that mutants of influenza virus defective in the PB2 and NP proteins can be grown to substantially higher titers in cell lines which were constructed to constitutively express the polymerase and NP proteins (Krystal et al., 1986 Proc. Natl. Acad. Sci. U.S.A. 83:2709–2813). Similar techniques may be used to construct transformed cell lines that constitutively express any of the influenza genes. These cell lines which are made to express the viral protein may be used to complement the defect in the recombinant virus and thereby propagate it. Alternatively, certain natural host range systems may be available to propagate recombinant virus. An example of this approach concerns the natural influenza isolate CR43-3. This virus will grow normally when passaged in primary chick kidney cells (PCK) but will not grow in Madin-Darby canine kidney cells (MDCK), a natural host for influenza (Maassab & DeBorde, 1983, Virology 130:342–350). When we analyzed this virus we found that it codes for a defective NS1 protein caused by a deletion of 12 amino acids. The PCK cells contain some activity which either complements the defective NS1 protein or can completely substitute for the defective protein.

A third approach to propagating the recombinant virus may involve co-cultivation with wild-type virus. This could be done by simply taking recombinant virus and co-infecting cells with this and another wild-type virus (preferably a vaccine strain). The wild-type virus should complement for the defective virus gene product and allow growth of both the wild-type and recombinant virus. This would be an analagous situation to the propagation of defective-interfering particles of influenza virus (Nayak et al., 1983, In: Genetics of Influenza Viruses, P. Palese and D. W. Kingsbury, eds., Springer-Verlag, Vienna, pp. 255–279). In the case of defective-interfering viruses, conditions can be modified such that the majority of the propagated virus is the defective particle rather than the wild-type virus. Therefore this approach may be useful in generating high titer stocks of recombinant virus. However, these stocks would necessarily contain some wild-type virus.

Alternatively, synthetic RNPs may be replicated in cells co-infected with recombinant viruses that express the influenza virus polymerase proteins. In fact, this method may be used to rescue recombinant infectious virus in accordance with the invention. To this end, the influenza virus polymerase proteins may be expressed in any expression vector/host cell system, including but not limited to viral expression vectors (e.g., vaccinia virus, adenovirus, baculovirus, etc.) or cell lines that express the polymerase proteins (e.g., see Krystal et al., 1986, Proc. Natl. Acad. Sci. U.S.A. 83: 2709–2713). Moreover, infection of host cells with rRNPs encoding all eight influenza virus proteins may result in the production of infectious chimeric virus particles. This system would eliminate the need for a selection system, as all recombinant virus produced would be of the desired genotype. In the examples herein, we describe a completely synthetic replication system where, rather than infecting cells with influenza virus, synthetic RNP's are replicated in cells through the action of influenza virus proteins expressed by recombinant vaccinia vectors. In this way we show that the only influenza virus proteins essential for transcription and replication of RNP are the three polymerase proteins and the nucleoprotein.

It should be noted that it may be possible to construct a recombinant virus without altering virus viability. These altered viruses would then be growth competent and would not need helper functions to replicate. For example, alterations in the hemagglutinin gene segment and the NS gene segment discussed, supra, may be used to construct such viable chimeric viruses.

In the examples infra, the construction of a recombinant plasmid is described that, following transcription by T7 polymerase, yielded an RNA template which was recognized and transcribed by the influenza virus polymerase in vitro. This RNA template corresponds to the NS RNA of an influenza virus except that the viral coding sequences are replaced by those of a CAT gene. This recombinant negative strand viral RNA template was then mixed with purified influenza virus polymerase to reconstitute an RNP complex. The recombinant RNP complex was transfected into cells which were then infected with influenza virus, leading to expression of CAT activity.

A number of factors indicate that this system represents a biologically active recombinant RNP complex which is under tight control of the signals for transcription, replication and packaging of influenza virus RNAs. First, the CAT gene is of negative polarity in the recombinant viral RNA used for RNP transfection. Thus, the incoming RNA cannot be translated directly in the cell and must first be transcribed by the influenza virus polymerase to permit translation and expression of the CAT gene. Secondly, neither transfected naked recombinant RNA alone in the presence of infecting helper virus, nor recombinant RNP complex in the absence of infecting helper virus is successful in inducing CAT activity. This suggests that influenza viral proteins provided by the incoming RNP, as well as by the infecting helper virus, are necessary for the amplification of the recombinant RNA template. Finally, after RNP-transfection and infection by helper virus, virus particles emerge which apparently contain the recombinant RNA, since these particles again induce CAT activity in freshly infected cells. These results suggest that the 26 3' terminal and the 22 5' terminal nucleotides corresponding to the terminal nucleotides in the influenza A virus NS RNA are sufficient to provide the signals for polymerase transcription and replication, as well as for packaging of the RNA into particles.

The foregoing results, which defined the cis acting sequences required for transcription, replication and packaging of influenza virus RNAs, were extended by additional working examples, described infra, which demonstrate that recombinant DNA techniques can be used to introduce site-specific mutations into the genomes of infectious influenza viruses.

Synthetic RNAs, derived by transcription of plasmid RNA in vitro were used in RNP-transfection experiments to rescue infectious influenza virus. To enable selection of this virus, we chose a system that required the presence of a WSN-like neuraminidase gene in the rescued virus. Viruses containing this gene can grow in MDBK cells in the absence of protease in the medium (Schulman et al., 1977, J. Virol. 4:170–176). The helper virus WSN-HK does not grow under these circumstances. Clearly, alternative selection systems exist. For example, antibody screens or conditionally lethal mutants could be used to isolate rescued viruses containing RNAs derived from plasmid DNAs. In the experiments viruses described infra, viruses which were WSN virus-like were recovered. The WSN NA gene was derived from plasmid DNAs or from purified WSN virion RNA (FIG. 17, lanes 2 and 5). In the latter case, using whole virion RNA for the RNP-transfection, we do not know whether other genes were also transfered to the rescued virus, since the helper virus shares the remaining seven genes with WSN virus. The rescued viruses had the expected RNA patterns (FIG. 17) and grew to titers in MDBK or MDCK cells which were indistinguishable from those of the wild type WSN virus. It should be noted that rescue of an NA RNA containing a single nucleotide deletion in the 5' nontranslated region was not possible. This again illustrates the importance of regulatory sequences present in the non-translated regions of influenza virus RNAs. We also rescued virus using RNA that was engineered to contain 5 nucleotide changes in a 39 nucleotide long region (FIG. 16). We verified the presence of these mutations in the rescued mutant virus by direct sequencing of the RNA (FIG. 18). These mutations did not result in any amino acid change in the neuraminidase protein and thus were not expected to change the biological property of the virus. Although this virus was not extensively studied, its plaquing behavior and its growth characteristics were indistinguishable from that of wild type WSN virus. Using such technology, mutations may be introduced that will change the biological characteristics of influenza viruses. These studies will help in distinguishing the precise functions of all the viral proteins, including those of the non-structural proteins. In addition, the nontranslated regions of the genome can be studied by mutagenesis, which should lead to a better understanding of the regulatory signals present in viral RNAs. An additional area of great interest concerns the development of the influenza virus system as a vaccine vector.

5.4. VACCINE FORMULATIONS USING THE CHIMERIC VIRUSES

Virtually any heterologous gene sequence may be constructed into the chimeric viruses of the invention for use in vaccines. Preferably, epitopes that induce a protective immune response to any of a variety of pathogens, or antigens that bind neutralizing antibodies may be expressed by or as part of the chimeric viruses. For example, heterologous gene sequences that can be constructed into the chimeric viruses of the invention for use in vaccines include but are not limited to epitopes of human immunodeficiency virus (HIV) such as gp120; hepatitis B virus surface antigen (HBsAg); the glycoproteins of herpes virus (e.g. gD, gE); VP1 of poliovirus; antigenic determinants of non-viral pathogens such as bacteria and parasites, to name but a few. In another embodiment, all or portions of immunoglobulin genes may be expressed. For example, variable regions of anti-idiotypic immunoglobulins that mimic such epitopes may be constructed into the chimeric viruses of the invention.

Either a live recombinant viral vaccine or an inactivated recombinant vital vaccine can be formulated. A live vaccine may be preferred because multiplication in the host leads to a prolonged stimulus of similar kind and magnitude to that occurring in natural infections, and therefore, confers substantial, long-lasting immunity. Production of such live recombinant virus vaccine formulations may be accomplished using conventional methods involving propagation of the virus in cell culture or in the allantois of the chick embryo followed by purification.

In this regard, the use of genetically engineered influenza virus (vectors) for vaccine purposes may require the presence of attenuation characteristics in these strains. Current live virus vaccine candidates for use in humans are either cold adapted, temperature sensitive, or passaged so that they derive several (six) genes from avian viruses, which results in attenuation. The introduction of appropriate mutations (e.g., deletions) into the templates used for transfection may provide the novel viruses with attenuation characteristics. For example, specific missense mutations which are associated with temperature sensitivity or cold adaption can be made into deletion mutations. These mutations should be more stable than the point mutations associated with cold or temperature sensitive mutants and reversion frequencies should be extremely low.

Alternatively, chimeric viruses with "suicide" characteristics may be constructed. Such viruses would go through only one or a few rounds of replication in the host. For example, cleavage of the HA is necessary to allow for reinitiation of replication. Therefore, changes in the HA cleavage site may produce a virus that replicates in an appropriate cell system but not in the human host. When used as a vaccine, the recombinant virus would go through a single replication cycle and induce a sufficient level of immune response but it would not go further in the human host and cause disease. Recombinant viruses lacking one or more of the essential influenza virus genes would not be able to undergo successive rounds of replication. Such defective viruses can be produced by co-transfecting reconstituted RNPs lacking a specific gene(s) into cell lines which permanently express this gene(s). Viruses lacking an essential gene(s) will be replicated in these cell lines but when administered to the human host will not be able to complete a round of replication. Such preparations may transcribe and translate—in this abortive cycle—a sufficient number of genes to induce an immune response. Alternatively, larger quantities of the strains could be administered, so that these preparations serve as inactivated (killed) virus vaccines. For inactivated vaccines, it is preferred that the heterologous gene product be expressed as a viral component, so that the gene product is associated with the virion. The advantage of such preparations is that they contain native proteins and do not undergo inactivation by treatment with formalin or other agents used in the manufacturing of killed virus vaccines.

In another embodiment of this aspect of the invention, inactivated vaccine formulations may be prepared using conventional techniques to "kill" the chimeric viruses. Inactivated vaccines are "dead" in the sense that their infectivity has been destroyed. Ideally, the infectivity of the virus is destroyed without affecting its immunogenicity. In order to prepare inactivated vaccines, the chimeric virus may be grown in cell culture or in the allantois of the chick embryo, purified by zonal ultracentrifugation, inactivated by formaldehyde or β-propiolactone, and pooled. The resulting vaccine is usually inoculated intramuscularly.

Inactivated viruses may be formulated with a suitable adjuvant in order to enhance the immunological response. Such adjuvants may include but are not limited to mineral gels, e.g., aluminum hydroxide; surface active substances such as lysolecithin, pluronic polyols, polyanions; peptides; oil emulsions; and potentially useful human adjuvants such as BCG and Corynebacterium parvum.

Many methods may be used to introduce the vaccine formulations described above, these include but are not limited to oral, intradermal, intramuscular, intraperitoneal, intravenous, subcutaneous, and intranasal routes. It may be preferable to introduce the chimeric virus vaccine formulation via the natural route of infection of the pathogen for which the vaccine is designed. Where a live chimeric virus vaccine preparation is used, it may be preferable to introduce the formulation via the natural route of infection for influenza virus. The ability of influenza virus to induce a vigorous secretory and cellular immune response can be used advantageously. For example, infection of the respiratory tract by chimeric influenza viruses may induce a strong secretory immune response, for example in the urogenital system, with concomitant protection against a particular disease causing agent.

6. EXAMPLE: PROMOTER ANALYSIS OF THE INFLUENZA VIRAL RNA POLYMERASE

In the examples described below, polymerase which is depleted of genomic RNA was prepared from the upper fractions of the CsCl-glycerol gradient centrifugation. This polymerase is able to copy short model templates which are derived from transcription of appropriate plasmid DNA with bacteriophage T7 RNA polymerase in a sequence-specific manner. The termini of this model RNA are identical to the 3'15 and 5'22 nucleotides conserved in segment 8 from all influenza A viral RNAs. By manipulating the plasmid in order to prepare different RNAs to serve as template, we demonstrated that recognition of and synthesis from this model RNA was specific for the promoter at the 3' terminal sequence and did not require the panhandle. In addition, site specific mutagenesis identified nucleotide positions responsible for the viral polymerase favoring synthesis from genomic sense templates over complementary sense RNA. Conditions were also found in which cap-endonuclease primed RNA synthesis could be observed using model RNAs. In addition, the reconstituted system permitted virus-specific synthesis from genomic length RNAs, derived either from plasmids or from RNA purified from virus through phenol extraction.

6.1. MATERIALS AND METHODS

6.1.1. PURIFICATION OF THE VIRAL RNA POLYMERASE

RNP cores were prepared from whole virus using standard methods (Plotch, et al., 1981, Cell 23: 847–858; Rochavansky, 1976, Virology 73: 327–338). Two to three milligrams of virus were disrupted by incubating in 1.5% Triton N-101, 10 mg/ml lysolecithin, 100 mM tris-HCl, pH 8.0, 100 mM KCl, 5 mM $MgCl_2$, 5% glycerol and 1.5 mM dithiothreitol. The sample was fractionated by centrifugation on a 30–70% glycerol (w/v) step gradient in the presence of 50 mM tris-HCl, pH 7.8 and 150 mM NaCl. The core preparation was centrifuged at 45,000 rpm in an SW50.1 rotor for 4 hours at 4° C. Fractions enriched in RNP were identified by SDS-polyacrylamide gel electrophoresis of protein samples from each fraction and staining with silver. The core fractions were then subjected to a second gradient centrifugation as was described in Honda et al. 1988, J. Biochem. 104: 1021–1026. This second gradient had steps of 0.5 ml 3.0M CsCl and 45% (w/v) glycerol, 1.75 ml 2.5 M CsCl and 40% glycerol, 1.25 ml 2.0M CsCl and 35% glycerol, and 1.0 ml of 1.5M CsCl and 30% glycerol. All steps were buffered with 50 mM tris-HCl, pH 7.6 and 100 mM NaCl. 0.5 ml of RNP cores were layered on top and the sample was centrifuged at 45,000 rpm in an SW50.1 rotor for 25 hours at 4° C. Polymerase fractions were again identified by SDS-polyacrylamide electrophoresis of the protein samples and silver staining. Active polymerase fractions were generally found in the region of the gradient correlating with 1.5 to 2.0M CsCl. These fractions were pooled and then dialyzed against 50 mM tri-HCl, pH 7.6, 100 mM NaCl and 10 mM $MgCl_2$ and concentrated in centricon-10 tubes (Amicon) or fractions were dialyzed in bags against 50 mM tris-HCl, pH 7.6, 100 mM NaCl, 10 mM $MgCl_2$, 2 mM dithiothreitol, and 50% glycerol.

6.1.2. PREPARATION OF PLASMID

The plasmid design is indicated in FIG. 2. Insert DNA for the pV-wt plasmid was prepared using an Applied Biosystems DNA synthesizer. The "top" strand was 5'-GAAGCT-TAATACGACTCACTATAAGTAGAAA-CAAGGGTGTTTTTTCATATCATTTAAACTTC ACCCTGCTTTTGCTGAATTCATTCTTCTGCAGG-3'. The "bottom" strand was synthesized by primer-extension with 5'-CCTGCAGAAGAATGA-3' as primer. The 95 bp DNA was digested with HindIII and PstI and purified by extraction with phenol/chloroform, ethanol precipitation, and passage over a NACS-prepack ion exchange column (Bethesda Research Laboratories). This DNA was ligated into pUC-19 which had been digested with HindIII and PstI and then used to transform E. coli strain DH5-α which had been made competent using standard protocols. Bacteria were spread on agar plates containing X-gal and IPTG, and blue colonies were found to have the plasmid containing the predicted insert since the small insert conserved the lacZ reading frame and did not contain a termination codon. The pM-wt plasmid was prepared by a similar strategy except that both strands were chemically synthesized with the upper strand having the sequence 5'-GAAGCTTAATACGACT-CACTATAAGCAAAAGCAGGGTGAAGTT-TAAATGATATGAAAAAACACCCT-TGTTTCTACTGAATTCATTCTTCTGCAGG-3'.

The pV-d5' plasmid (FIG. 2) was prepared using the oligonucleotides 5'-AGCTTAATACGACTCACTATAA-GATCTATTAAACTTCACCCT-GCTTTTGCTGAATTCATTCTTCTGCA-3' and 5'-GAA-GAATGAATTCAGCAAAAGCAGGGTGAAGTTTAATA GATCTTATAGTGAGTCGTATTA- 3'. The DNAs were annealed and ligated into the HindIII/PstI digested pUC-19 and white colonies were found to contain the correct plasmid because this insert resulted in a frameshift in the lacZ gene.

The point mutants were isolated following digestion of pV-d5' with BglII and PStI and ligation of the linearized plasmid with a single stranded oligonucleotide of mixed composition. Since BglII laves a 5' extension and PstI a 3' extension, a single oligonucleotide was all that was necessary for ligation of insert. The host cell was then able to repair gaps caused by the lack of a complementary oligonucleotide. Oligonucleotides were designed to repair the frameshift in the lacZ gene so that bacteria which contained mutant plasmids were selected by their blue color.

Plasmid pHgaNS, which was used to prepare an RNA identical to segment 8 of A/WSN/33, was prepared using the primers 5'-CCGAATTCTTAATACGACTCACTATAAG-TAGAAACAAGGGTG-3' and 5'-CCTCTAGACGCTC-GAGAGCAAAAGCAGGTG-3' in a polymerase chain reaction off a cDNA clone. The product was then cloned into the XbaI/EcoRI window of pUC19.

6.1.3. PREPARATION OF RNA TEMPLATES

Plasmid DNAs were digested with MboII or other appropriate endonucleases (see FIG. 2), and the linearized DNA was transcribed using the bacteriophage T7 RNA polymerase. Run-off RNA transcripts were treated with RNAse-free DNAse 1 and then the RNA was purified from the proteins and free nucleotides using Qiagen tip-5 ion exchange columns (Qiagen, Inc.). Following precipitation in ethanol, purified RNAs were resuspended in water and a sample was analyzed by electrophoresis and followed by silver staining of the polyacrylamide gel in order to quantitate the yield of RNA.

6.1.4. INFLUENZA VIRAL POLYMERASE REACTIONS

In a 25 µl total volume, about 30 µg of nucleoprotein and 200 pg total of the three polymerase proteins were mixed with 10 ng of template RNA and the solution was made up to a final concentration of: 50 mM Hepes pH 7.9, 50 mM NaCl, 5 mM $MgCl_2$, 1 mM dithiothreitol, 0.05% NP-40, 0.4 mM adenylyl-(3'–5')-guanosyl (ApG) dinucleotide (Pharmacia), 0.5 mM ATP, 0.5 mM GTP, 0.5 mM CTP and approximately 0.6 µM $\alpha$-$^{32}$P-UTP (40 µCi at 3000 Ci/mmole, New England Nuclear). Reactions were assembled on ice and then transferred to a 30° C. water bath for 90 minutes. Reactions were terminated by the addition of 0.18 ml ice-cold 0.3M sodium acetate/10 mM EDTA and were then extracted with phenol/chloroform (1:1 volume ratio). Following the first extraction, 15 µg polyI-polyC RNA was added as carrier, and the sample was extracted again with phenol/chloroform. The samples were then extracted with ether and precipitated in ethanol. Following centrifugation, the RNA pellet was washed twice with 70% ethanol and then dried under vacuum.

In reactions using the high concentration polymerase, conditions were identical as above except that 20 ng of template RNA were added. In reactions using genomic length RNAs, the amount of polymerase used was doubled, 50 ng of template RNA was used, and the UTP concentration was raised to 2.6 µM.

The RNA was resuspended in a dye mix containing 78% formamide, 10 mM EDTA, 0.1% xylene cyanol and 0.05% bromophenol blue. Typically, a sample from this RNA was electrophoresed on an 8% polyacrylamide gel in the absence of urea, and the remainder was denatured by heating to 100° C. for 1.5 minutes and an aliquot was loaded on an 8% polyacrylamide gel containing 7.7M urea. Gels were fixed by a two step procedure, first in 10% acetic acid, and then in 25% methanol/8% acetic acid. Gels were dried onto filter paper and then exposed to x-ray film.

When different RNAs were being tested for use as template, the different RNA preparations were always analyzed on polyacrylamide gels and stained with silver in order that equal amounts of each template were used. To quantitate the amount of product, gels were exposed to x-ray film in the absence of an intensifying screen in order to improve the linearity of the densitometer readings. Autoradiographs were analyzed using a FB910 scanning densitometer (Fisher Biotech) and peaks were evaluated using computer software from Fisher Biotech.

6.1.5. NUCLEASE ANALYSIS OF REACTION PRODUCTS

For ribonuclease T1 analysis of the two principle RNA products, reaction products were analyzed by 8% polyacrylamide gel electrophoresis (without urea) and the gel was not treated with fixative. The wet gel was exposed to an x-ray film and the appropriate gel pieces were located and excised. The gel piece was crushed in 0.3 ml containing 10 mM tris pH 7.5, 1 mM EDTA, 0.1% sodium dodecyl sulfate, and 1 µl tRNA as carrier. The RNA diffused into this solution for 3 hours and then the gel was pelleted and the supernatant was made 0.3M in sodium acetate. The supernatant was then extracted twice in phenol/chloroform and once in ether and then precipitated in ethanol. The RNA pellet was resuspended in 5 µl formamide, denatured in boiling water for 1.5 minutes and then diluted by the addition of 0.1 ml 10 mM tris-HCl, pH 7.5, and 1 mM EDTA. Ribonuclease T1 (50 units, Boehringer Mannheim Biochemicals) was added and the samples were incubated for 60 minutes at 37° C. V-wt and M-wt RNAs synthesized with T7 RNA polymerase in the presence of $\alpha$-$^{32}$P-UTP were similarly digested with RNAse T1. Reaction products were extracted in phenol/chloroform and precipitated in ethanol and then were analyzed on 20% polyacrylamide gels containing 7.7M urea.

Nuclease S1 analysis of reaction products was done on transcribed RNA by first terminating the standard polymerase reaction through the addition of S1 buffer to a volume of 0.2 ml with 0.26M NaCl, 0.05M sodium acetate, pH 4.6, and 4.5 mM zinc sulfate. The sample was divided into two 0.1 ml volumes and 100 units of S1 nuclease (Sigma Chemical Company) were added to one tube. The samples were incubated for 60 minutes at 37° C. Following the incubation, EDTA (10 mM final concentration) and 15 µg polyI-polyC RNA was added and the sample was extracted with phenol/chloroform and precipitated in ethanol. The samples were then subjected to polyacrylamide gel electrophoresis.

6.2. RESULTS

6.2.1. PREPARATION OF INFLUENZA VIRAL RNA POLYMERASE AND OF TEMPLATE RNA

RNP cores of influenza virus A/Puerto Rico/8/34 were prepared by disruption of virus in lysolecithin and Triton N-101 followed by glycerol gradient centrifugation (Rochavansky, 1976, Virology 73: 327–338). Fractions containing cores were then subjected to a second centrifugation in a CsCl-glycerol step gradient (Honda, et al., 1988, J. Biochem. 104: 1021–1026). Fractions containing the polymerase were identified by gel electrophoresis of samples followed by silver-staining. FIG. 1 shows the polymerase preparation after CsCl centrifugation. Bovine serum albumin (BSA) was added during dialysis to protect against protein loss. Densitometric scanning of lane 4 compared to known quantities of whole virus in lanes 1 and 2 allowed us to estimate that the proteins in lane 4 consist of 150 ng of NP and about 1 ng total of the three polymerase proteins. One fifth of the preparation used for this gel was used per reaction.

The overall design of the plasmids used to prepare template RNAs in this study is depicted in FIG. 2. The entire insert was prepared using oligonucleotides from a DNA synthesizer which were then cloned into the polylinker of pUC19. The insert contained a truncated promoter sequence recognized by the bacteriophage T7 RNA polymerase (Studier and Dunn, 1983, Cold Spring Harbor Symposia on Quantitative Biology, XLVII, 999–1007) so that the first nucleotides synthesized were the terminal 22 nucleotides (nt) of the conserved sequence from the 5' end of the genome RNA. When the plasmid was cut with restriction endonuclease MboII (which cuts 7 bases upstream of its recognition site), the RNA which resulted from T7 RNA polymerase transcription ended with the terminal 3' nucleotides of the influenza viral sequence. Included in the sequence was the poly-U stretch adjacent to the 5' end of the conserved terminus which is thought to comprise at least part of the termination-polyadenylation signal (Robertson, et al., 1981, J. Virol. 38, 157–163). The total length of this model genomic RNA was 53 nt since a 16 nt spacer separated the terminal conserved sequences. The model RNA which contained both termini identical to those of vRNA was named V-wt. The RNA M-wt encoded the exact complementary strand of V-wt so that the termini match those of complementary RNA (cRNA). V-wt and M-wt were constructed to serve as models for influenza virus-specific vRNA and cRNA, respectively.

6.2.2. VIRAL POLYMERASE CATALYZES SYNTHESIS OF A FULL LENGTH COPY OF THE TEMPLATE

In the reaction using the influenza viral polymerase, V-wt template and hpG primer, a product was obtained which comigrated with a 53 nt RNA on denaturing gels. RNA migrating as a doublet at a position of about 40 to 45 nucleotides (FIG. 3A, lane 2) was also seen. This shorter product is shown below to be RNA which had terminated at a stretch of adenosines present between nucleotides 43–48 in the virion sense template. In addition to the template specific transcripts, a general background of light bands could be seen which correspond to truncated RNA products transcribed from viral genomic RNA not removed during the CsCl-glycerol centrifugation step. When no primer is used, there was no specific transcription product seen (FIG. 3A, lane 3). Additional experiments showed globin mRNA, containing a terminal cap 1 structure, was inactive as primer using initial preparations of polymerase.

When the polymerase reaction was terminated by the addition of excess buffer favorable for nuclease S1 digestion and nuclease was added, the radioactively-labeled product was resistant to digestion (FIG. 3B, lane 2). By contrast these conditions very efficiently digested the V-wt single-stranded RNA radioactively synthesized with T7 RNA polymerase (FIG. 3B, lanes 3 and 4). These nuclease S1 data confirmed that the opposite strand was indeed being synthesized in these reactions. The product of the reaction might be a double stranded RNA, but it could not be ruled out that the product was in fact single stranded and later annealed to the template RNA in the presence of high salt used in the nuclease reaction.

The RNA products were purified by electrophoresis on an 8% gel, excised, eluted from the gel, and then digested by ribonuclease T1. Products were analyzed by electrophoresis and compared to the patterns generated by RNase T1 digestion of internally labeled M-wt and V-wt control probes. As can be seen in FIG. 3C, the full length RNA (lane 1) has the identical pattern as does the plus sense RNA, M-wt (lane 3), and it does not have the pattern of the V-wt RNA (lane 4). The observed patterns were essentially identical to that which is predicted from the sequence of the RNA and thus showed that the polymerase faithfully copied the V-wt template. The smaller RNA product, a doublet with most templates, was also digested with RNase T1. Its pattern was similar to that of the full length RNA product (FIG. 3C, lane 2) except the 14 base oligonucleotide was not present. Instead, a faint 13 base oligonucleotide was seen, thus mapping the termination of the short RNA to position 44, a site where two uridines would be incorporated. Since the amount of smaller RNA product decreased at higher UTP concentrations and disappeared when CTP was used as label, these bands appeared to be an artifact of low UTP concentrations in the polymerase reaction.

6.2.3. CONDITIONS FOR THE POLYMERASE REACTIONS USING MODEL RNA TEMPLATES

It was found that protein samples containing about 30 ng of NP protein and about 200 pg total of the three P proteins would react optimally with 5 to 10 ng of RNA. By using cold competitor RNA, polyI-polyC, it was found that excess RNA nonspecifically inhibited transcription, possibly via non-specific binding of the NP protein (Kingsbury, et al., 1987, Virology 156: 396–403; Scholtissek and Becht, 1971, J. Gen. Virol. 10: 11–16). In the absence of nonspecific competitor, variations in the amount of template between 1 and 10 ng produced little change in the efficiency of RNA synthesis. The NP protein and RNA were present at about equal molar concentrations and these were each about a thousand-fold in excess of the moles of the complex (assuming it to be 1:1:1) formed by the three P proteins in the typical reaction.

Since these reconstituted RNPs were able to use ApG but not globin mRNA as primer, we tested these model RNPs for other variables of the transcription reaction. In all other ways tested, the reconstituted RNPs behaved in solution similarly to those RNPs purified from detergent disrupted virus. The optimum temperature for RNA synthesis was 30° C. (FIG. 4A, lane 2) as has been repeatedly found for the viral polymerase (Bishop, et al., 1971, J. Virol. 8: 66–73; Takeuchi, et al., 1987, J. Biochem. 101: 837–845; Ulmanen, et al., 1983, J. Virol. 45: 27–35). Also, the most active salt conditions were 60 mM NaCl (FIG. 4B, lane 2), again consistent with conditions used by several groups (Bishop, et al., 1971, J. Virol. 8: 66–73; Honda, et al., 1988, J. Biochem. 104: 1021–1026; Shapiro, and Krug, 1988, J. Virol. 62: 2285–2290). FIG. 4C shows a time-course experiment. The amount of RNA synthesis appeared to increase roughly linearly for the first 90 minutes, as was found for viral RNPs (Takeguchi, et al., 1987, J. Biochem. 101: 837–845).

6.2.4. SPECIFICITY OF THE ELONGATION REACTION

Various RNAs were tested for suitability as templates for the RNA polymerase of influenza virus. The pV-wt plasmid clone was digested with either EcoRI, PstI or SmaI, and T7 polymerase was used to transcribe RNA. This resulted in RNAs identical to V-wt except for the addition of 5, 13 and 38 nt at the 3' end. In FIG. 5A an overexposure of an autoradiograph is shown in order to demonstrate that no transcripts over background were observed in reactions which contained as template: two of the RNAs identical to V-wt except they contained 13 and 38 nt of extra sequence on the 3' terminus (lanes 1 and 2); a single stranded DNA of identical sequence to that of V-wt (lane 4); and an unrelated 80 nt RNA generated by transcribing the polylinker of pIBI-31 with T3 RNA polymerase (lane 5). However, the V-Eco template, containing five extra nucleotides on the 3' end, could be recognized and faithfully transcribed, although at approximately one-third the efficiency of the wild type V-wt RNA (FIG. 5B, lane 3). It is interesting to note that initiation on the V-Eco RNA by the influenza viral polymerase appeared to occur at the correct base since the transcribed RNA was the same size as the product form the V-wt template.

6.2.5. ANALYSIS OF THE PROMOTER REGION FOR THE VIRAL RNA POLYMERASE

The original construct used for these studies contained the sequences of both RNA termini of genomic RNAs which could base pair and thus form a panhandle. This was done since it was shown that the vRNA in virions and in RNPs in infected cells was in circular conformation via the 15 to 16 nt long panhandle (Honda, et al., 1988, J. Biochem. 104: 1021–1026; Hsu, et al., 1987, Proc. Natl. Acad. Sci. U.S.A. 84: 8140–8144). It was further shown that the viral polymerase was bound to the double stranded structure (Honda, et al., 1988, J. Biochem. 104: 1021–1026), thus leading to the suggestion that the promoter for RNA synthesis was the panhandle. In order to test whether the panhandle was an absolute requirement for recognition, the following templates were used: the plasmid pV-wt was digested with DraI prior to transcription by the T7 polymerase (FIG. 2). This should result in an RNA molecule of 32 nt containing only virus-specific sequences from the 5' end of the RNA. When this RNA was used as template, no apparent product was produced (FIG. 5B, lane 2). Therefore the 3' terminus of virion RNA was required for this reaction. This finding was consistent with the fact that the initiation site at the 3' end of V-wt was not present in V-Dra. A second plasmid clone was produced which deleted the 5' terminal sequences but kept intact the 3' terminus This clone pV-d5' when digested with MboII and used for transcription by T7 polymerase produced a major transcript of 30 nt and minor species of 29 and 31 nt. Surprisingly, this template was recognized and copied by the influenza viral polymerase. FIG. 7, lane 1, shows that the product of the viral RNA polymerase reaction with V-d5' contains multiple bands reflecting the input RNA. When the products shown in FIG. 7, lane 1, were eluted from gels and subjected to RNase T1 analysis, the pattern expected of the transcription product of V-d5' was observed. Since the V-d5' RNA template was copied, the panhandle was not required for viral polymerase binding and synthesis.

Although the 5' terminus was not required for synthesis by the polymerase, a distinct possibility was that V-wt RNA might be a preferred template as compared to V-d5'. In order to examine this, reactions were done in which the templates were mixed. The V-wt RNA was present at 5 ng in each reaction. The V-d5' was absent (FIG. 6, lane 1) or was present at a 1/5 molar ratio (FIG. 6, lane 2) or a 1/1 molar ratio (FIG. 6, lane 3). The relative intensities of the bands from each RNA were determined by densitometry of the autoradiograph. The values were corrected for the amount of the radioactive nucleotide, UTP, which could be incorporated into each product, and the value was normalized so that the level of synthesis in each lane was set equal to one. The level of copying of V-wt decreased as V-d5' was increased. When V-d5' was present in one fifth molar ratio, its corrected level of synthesis was about one fourth of that from V-wt (FIG. 6, lane 2). When the two templates were present in equimolar amounts, the level of synthesis from V-wt was about 60% of the total (FIG. 6, lane 3) which might be within the expected range of experimental error for equivalent levels of synthesis. Similar results were obtained when V-d5' RNA was kept constant and the V-wt RNA was varied. It was thus concluded that the panhandle-containing V-wt RNA was not greatly favored over the template RNA which only contained the proper 3' terminus.

6.2.6. THE VIRAL POLYMERASE DOES NOT COPY RNA TEMPLATES CONTAINING PLUS-SENSE TERMINI

As described earlier, the influenza RNA polymerase performs three distinct activities during the course of an infection. Two activities involve the transcription of genome sense RNA and the third involves copying of the complementary sense RNA into vRNA. We therefore constructed an RNA template which contained the 5' and 3' termini of the complementary sense RNA of segment 8 (M-wt; FIG. 2).

When the M-wt RNA was used as template, little synthesis was observed (FIG. 5B, lane 4). In two experiments used for quantitation, the average level of synthesis from M-wt RNA was 4% that of V-wt. In comparing the V-wt and M-wt RNA promoters, the M-wt has only three transition changes and one point insertion within the 3'15 nucleotides. These include a G to A change at position 3, a U to C change at position 5, a C to U change at position 8 and an inserted U between the ninth and tenth nucleotides (see Table II, below). In order to determine which of the four point differences in the 3' termini were responsible for the specificity, many combinations of these were prepared and assayed for efficiency as a template (FIG. 7). These templates were derivatives of V-d5' since they did not contain the 5' terminus. The results of densitometry scans of several experiments are outlined in Table II.

TABLE II

QUANTITATIVE COMPARISON OF THE EFFECT OF POINT MUTATIONS IN THE PROMOTER SEQUENCE*

| Template | 3' sequence | Level of RNA Synthesis |
|---|---|---|
| V-d5' | CACCCUGCUUUUGCU-OH | 1 |
| V-A3 | CACCCUGCUUUUACU-OH | 0.4 |
| V-C5 | CACCCUGCUUCUGCU-OH | 1.0 |
| V-dU$_{25}$U$_8$ | CACCCUGUUUUGCU-OH | 1.0 |
| V-U$_8$A$_3$ | CACCCUGUUUUACU-OH | 0.08 |
| V-U$_8$C$_5$ | CACCCUGUUUCUGCU-OH | 0.3 |
| V-iU$_{10}$ | CACCCUUGCUUUUGCU-OH | 0.7 |
| V-iU$_{10}$A$_3$ | CACCCUUGCUUUUACU-OH | 0.06 |
| V-iU$_{10}$U$_8$A$_3$ | CACCCUUGUUUUACU-OH | 0.2 |
| V-iU$_{10}$U$_8$C$_5$A$_3$ | CACCCUUGUUUCUACU-OH | 0.2 |

*Sequences of V-wt, M-wt and V-d5' are shown in FIG. 2. All other RNAs are identical to V-d5' except for the indicated positions. The subscripted number indicates the distance from the 3' end of a change, and d and i refer to deleted or inserted nucleotides.

As shown in Table II, single point changes in V-d5' were equally well copied as compared to V-d5' itself, except for the V-A$_3$ RNA which was copied at 40% efficiency (FIG. 7, lane 10; Table II). When RNAs with two changes were tested, the activity generally dropped to very low levels (FIG. 7, lanes 3, 4, and 5). Therefore, these experiments confirmed that the specificity of the reactions for V-wt over M-wt was the result of the combination of the nucleotide changes present at the 3' terminus of M-wt.

6.2.7. CAP-ENDONUCLEASE PRIMED RNA SYNTHESIS

The method of purifying the viral polymerase was modified in order to decrease loss of protein during dialysis. Rather than using the Amicon centricon-10 dialysis system, the enzyme was dialyzed in standard membranes resulting in higher concentrations of all four viral core proteins. The pattern of the protein gel of this preparation was identical to that shown in FIG. 1, lane 4, except that there is no BSA-derived band. It was found that 5 μl of this preparation, containing 150 ng of NP and 5 ng total of the three polymerase proteins, reacted optimally with 10 to 40 ng of model RNA template. However, the use of higher levels of protein increased the background, possibly due to higher levels of contaminating RNAs (virion RNAs not removed by CsCl centrifugation) yielding products of the size class around 50–75 nt, complicating analysis of RNA templates containing a length of 50 nt.

This high concentration polymerase preparation was now active in cap-endonuclease primed RNA synthesis (FIG. 8A, lane 4) and also in primer-independent replication of the template RNA (FIG. 8A, lane 2). When globin mRNA was used as primer for transcription from the 30 nt V-d5' template, a triplet of bands of size about 42 to 44 nt was apparent as product (FIG. 8A, lane 4), consistent with cleavage of the cap structure at about 12 nt from the 5' end of the mRNA and use of this oligonucleotide to initiate synthesis from the 30 nt model template. Since excess RNA inhibits RNA synthesis, probably via nonspecific binding of NP in vitro as discussed above, the optimal amount of cap donor RNA added to each reaction was found to be 100 ng, which is much lower than is usually used with preformed RNP structures (e.g. Bouloy, et al., 1980, Proc. Natl. Acad. Sci. U.S.A. 77:3952–3956). The most effective primer was ApG (FIG. 8A, lane 5 and lighter exposure in lane 6). The product migrates slower than that of the input template (FIG. 8A, lane 1) or the product in the absence of primer (FIG. 8A, lane 2) probably since the 5' terminus of the ApG product is unphosphorylated. The intensity of the ApG-primed product was about ten-fold higher than that of the cap-primed product, but at 0.4 mM, ApG was at a 60,000-fold molar excess of the concentration of the cap donors. Thus, although the intensity of the product band from cap-priming was about ten-fold lower than that from ApG priming, the cap-primed reaction was about 6000-fold more efficient on a molar basis. This value is similar to the approximately 4000-fold excess efficiency observed previously for the viral polymerase (Bouloy, et al., 1980, Proc. Natl. Acad. Sci. U.S.A. 77: 3952–3956). It has been previously shown that cap donor RNAs containing a cap 0 structure, as in BMV RNA, are about ten-fold less active in priming the influenza viral polymerase (Bouloy, et al., 1980, Proc. Natl. Acad. Sci. U.S.A. 77: 3952–3956). This unusual cap specificity was shared by the reconstituted RNPs studied here as the specific product from the model RNA was greatly decreased in reactions containing BMV RNA as cap donor. A 30 nt product was observed in lanes 2–4, probably due to primerless replication of the model template.

That the product RNAs were of the opposite sense of the input template V-d5' was shown by nuclease S1 analysis (FIG. 8B). The ApG-primed (FIG. 8B, lanes 1 and 2) and the primerless (FIG. 8B, lanes 3 and 4) RNA products were essentially nuclease resistant. The product of the cap-primed reaction (FIG. 8B, lanes 5 and 6) was partially sensitive to nuclease as about 12 nt were digested from the product. These results were Most consistent with the 5'12 nt being of mRNA origin as has been shown many times for influenza virus-specific nRNA synthesis.

The promoter specificity of this polymerase preparation in reactions prined with ApG was found to be essentially identical to those for the lower concentration enzyme as shown earlier. However, attempts thus far to perform similar analyses of promoter specificity with the primerless and cap-primed reactions have been frustrated by the comparatively high levels of background, thus making quantitation difficult.

6.2.8. REPLICATION OF GENOMIC LENGTH RNA TEMPLATES

A full length B90 nt RNA identical to the sequence of A/WSN/33 segment 8 was prepared by T7 RNA polymerase transcription of plasmid DNA, pHgaNS, which had been digested with restriction endonuclease HgaI. This RNA was copied in ApG-primed reactions containing 10 μl of the high concentration polymerase (FIG. 9, lane 8). That the RNA was in fact a copy of the template was demonstrated by its resistance to nuclease S1 (FIG. 9, lane 9). A similar product was observed in the absence of primer (FIG. 9, lanes 2 and 3). Confirmation that these product RNAs were full length copies of the template was done by RNase T1 analysis. Virion RNA purified from phenol-extracted A/PR/8/34 virus was similarly copied in ApG primed reaction (FIG. 9, lanes 10 and 1) and in the absence of primer (FIG. 9, lanes 4 and 5). Interestingly, the product from replication of the HA gene was at greatly reduced levels. The 3' end of this RNA differs from that of segment 8 only at nucleotides 14 and 15, suggesting importance for these nucleotides in the promoter for RNA synthesis. In addition, we found that when whole viral RNA was used in the reconstituted RNPs, the level of acid precipitable counts was about 70% of that observed with native RNPs. The vital polymerase was also able to copy these full length RNAs when globin mRNA was used in cap-primed reaction.

7. EXAMPLE: EXPRESSION AND PACKAGING OF A FOREIGN GENE BY RECOMBINANT INFLUENZA VIRUS

The expression of the chloramphenicol transferase gene (CAT) using rRNPs is described. The rRNPs were prepared using pIVACAT (originally referred to as pCATcNS), a recombinant plasmid containing the CAT gene. The pIVA-CAT plasmid is a pUC19 plasmid conaining in sequence: the T7-promoter; the 5'-(viral-sense) noncoding flanking sequence of the influenza A/PRS/34 RNA segment 8 (encodes the NS proteins); a BglII cloning site; the complete coding sequence of the chloramphenicol transferase (CAT) gene in the reversed and complemented order; the 3'-(viral-sense) noncoding NS RNA sequence: and several restriction sites allowing run-off transcription of the template. The pIVACAT can be transcribed using T7 polymerase to create an RNA with influenza A viral-sense flanking sequences around a CAT gene in reversed orientation.

The in vivo experiments described in the subsections below utilized the recombinant RNA molecule described containing sequences corresponding to the untranslated 3' and 5' terminal sequences of the NS RNA of influenza virus A/PR/8/34 flanking the antisense-oriented open reading frame of the CAT gene. This RNA was mixed with purified influenza virus polymerase complex and transfected into MDCK (or 293) cells. Following infection with influenza A/WSN/33 virus, CAT activity was measured in the RNP-transfected cells and amplification of the gene was indicated. In addition, the recombinant influenza virus gene was packaged into virus particles, since CAT activity was demonstrated in cells following infection with the recombinant virus preparation.

7.1. MATERIALS AND METHODS

In order to get the flanking sequences of the NS RNA fused to the coding sequence of the CAT gene, the following strategy was used. Two suitable internal restriction sites were selected, close to the start and stop codon of the CAT gene, that would allow the replacement of the sequences flanking the CAT gene in the pCM7 plasmid with the 3'- and 5'-NS RNA sequences. At the 5' and, a SfaNI site was chosen, (which generates a cut 57 nt from the ATG) and at the 3'-end a ScaI site which generates a cut 28 nt from the end of the gene (stop codon included). Next, four synthetic oligonucleotides were made using an Applied Biosystems DNA synthesizer, to generate two double-stranded DNA fragments with correct overhangs for cloning. Around the start codon these oligonucleotides formed a piece of DNA containing a XbaI overhang followed by a HgaI site and a PstI site, the 3'-(viral-sense) NS sequence immediately followed by the CAT sequence from start codon up to the SfaNI overhang (underscored). In addition a silent mutation was incorporated to generate an AccI site closer to the start codon to permit future modifications.

```
 Xba I
    Hga I  Pst I                                    Acc
5'-ctagacgccctgcagcaaaagcagggtgacaaagacataatggagaaaaaaatcac
   3'tgcgggacgtcgttttcgtcccactgtttctgtattacctcttttttagtg I          SfaN I
tgggtataccaccgttgatatatcccaatcgcatcgtaaa- 3'         oligo2
acccatatggtggcaactatatagggttagcgtagcatttcttg- 5'     oligo1
```

Around the stop codon the two other oligonucleotides generated a piece of DNA as follows: a blunt-ended ScaI site, the CAT sequence from this site up to and including the stop codon (underlined) followed by a BglII site and a Xba I overhang.

```
    Sca I                          Bgl II
5'-actgcgatgagtggcagggcggggcgtaatagat- 3'     oligo3
3'-tgacgctactcaccgtcccgccccgcattatctagatc- 5' oligo4
                                    XbaI
```

Using a single internal EcoRI site in the CAT sequence, the SfaNI/EcoRI and the EcoRI/ScaI fragment from pCM7 were independently cut out and purified from acrylamide gels. The SfaNI/EcoRI fragment was subsequently ligated with the synthetic DNA fragment obtained by annealing oligonucleotides 1 and 2 into a pUC19 plasmid that was cut with XbaI and EcoRI. The EcoRI/ScaI fragment was similarly cloned into an XbaI and EcoRI-digested pUC19 plasmid using oligonucleotides 3 and 4. The ligated DNA was transformed into competent DH5a bacteria, amplified, isolated and screened by means of restriction analysis using standard techniques.

The recombinants with the SfaNI containing insert were cut with XbaI and EcoRI and the plasmids with the ScaI insert were cut with EcoRI and BglII. The fragments were purified from acrylamide gel and cloned together into the pPHV vector which had been cut with XbaI and BglII. After transformation, white colonies were grown, analysed by endonuclease digestion and selected clones were sequenced. The final clone, pCATcNS2, was grown in large amounts and sequenced from the flanking pUC sequences up to 300 nt into the CAT gene, revealing no discrepancies with the intended sequence, with the exception of a G to A transition in the CAT gene, which appeared silent.

7.1.1. VIRUSES AND CELLS

Influenza A/PR/8/34 and A/WSN/33 viruses were grown in embryonated eggs and MDCK cells, respectively (Ritchey et al. 1976, J. Virol. 18: 736–744; Sugiura et al., 1972, J. Virol. 10: 639–647). RNP-transfections were performed on human 293 cells (Graham et al., 1977, J. Gen. Virol. 36:59–72) and on Madin-Darby canine kidney (MDCK) cells (Sugiura et al., 1972, supra).

7.1.2. CONSTRUCTION OF PLASMIDS

Plasmid pIVACAT1, derived from pUC19, contains the coding region of the chloramphenicol acetyltransferase (CAT) gene flanked by the noncoding sequences of the influenza A/PR/8/34 RNA segment 8. This construct is placed under the control of the T7 polymerase promoter in such a way that the RNA transcript IVACAT1 contains in 5' to 3' order: 22 nucleotides derived from the 5' terminus of the influenza virus NS RNA, an 8 nt linker sequence including a BglII restriction site, the CAT gene in negative polarity, and 26 nt derived from the 3' end of the influenza virus NS RNA (FIG. 11).

pIVACAT1 was constructed in the following way: In order to obtain the correct 5'-end in pIVACAT1, the EcoRI-ScaI fragment of the CAT gene derived from plasmid pCM7 (Pharmacia) was ligated to a DNA fragment formed by two synthetic oligonucleotides. The sequence of these oligonucleotides are: 5'-ACTGCGATGAGTG-GCAGGGCGGGGCGTAATAGAT-3' (top strand), and 5'-CTAGATCTATTACGCCCCGCCCTGC-CACTCATCGCAGT-3' (bottom strand). For the 3'-end of the insert in pIVACAT1 the SfaN 1-EcoRI fragment of the CAT gene was ligated to a DNA fragment made up of the synthetic oligonucleotides: 5'-CTAGACGCCCTGCAG-CAAAAGCAGGGTGACAAAGACATAATG-GAGAAAAAAAATCACTGGGTATACCAC-CGTTGATATATCCCAATCG CATCGTAAA-3' (top strand), and 5'-GTTCTTTACGATGCGATTGGGATATAT-CAACGGTGGTATACCCAGT- . GATTTTTTTCTCCATTATGTCTTTGTCACCCTGCT TTTGCTGCAGGGCGT-3' (bottom strand). Oligonucleotides were synthesized on an Applied Biosystems DNA synthesizer. These 5' and 3' constructs were ligated into pUC19 shuttle vectors digested with XbaI and EcoRI, grown up, cut out with EcoRI/BglII (5' region) and XbaI/EcoRI (3' region) and ligated into BglII/XbaI cut pPHV. The latter plasmid is similar to pV-WT described in Section 6, supra, except that it contains a BglII site which separates the noncoding terminal sequences of the influenza A virus NS RNA segment. The final clone pIVACAT1 (FIG. 1) was grown up and the DNA was partially sequenced starting from the flanking pUC sequences and reaching into the CAT gene. No changes were found as compared to the expected sequences with the exception of a silent G to A transition in the CAT gene at position 106 relative to the start of the IVACAT1 RNA.

7.1.3. T7 RNA TRANSCRIPTION

Plasmid pIVACAT1 was digested with MgaI (FIG. II), to allow run-off transcription. The 5 nt overhang generated by this enzyme was filled in with Klenow enzyme (BRL) and the DNA was purified over a spin column (Boehringer). The T7 polymerase reaction was performed using standard procedures in the presence of Rnasin (Promega). Template DNA was removed from Rnase free Dnase I (Promega). The RNA was purified over Qiagen tip-5 columns (Qiagen, Inc.) and quantitated using 4% polyacrylamide gels which were silver stained. NS RNA was prepared from plasmid pHgaNS in the same way.

7.1.4. PURIFICATION OF INFLUENZA A VIRUS POLYMERASE AND IN VITRO TRANSCRIPTION

The RNA polymerase complex was purified from influenza A/PR/8/34 as described in Section 6, supra. In vitro transcriptions of cold IVACAT1 or HgaNS RNA template were carried out using the conditions which have been described in Section 6, .supra. Radiolabeled transcripts were analysed on 4% acrylamide gels.

7.1.5. RNP-TRANSFECTION OF MDCK AND 293 CELLS 35 mm dishes containing approximately $10^6$ cells were treated with 1 ml of a solution of 300 µg/ml DEAE-dextrin, 0.5% DMSO in PBS/gelatine (0.1 mg/ml gelatine) for 30 minutes at room temperature. After removal of this solution, 200 µg of µl PBS/gelatine containing 1 µg IVACAT1 RNA (1–2 µl), 20 µl of the purified polymerase preparation and 4 µl of Rnasin was added to the cells and incubated for 1 hour at 37° C. This was followed by the addition of gradient purified influenza A/WSN/33 virus (moi 2–10). After incubation for one hour at 37° C., 2.5 ml of either DMEM+10% FCS media (293 cells) or MEM media (MDCK cells) was added. In some experiments MDCK cells were first infected and subsequently RNP-transfected. Harvesting of cells was done in NET buffer or in media, using a rubber policemen (MDCK cells), or by gentle suspension (293 cells). Cells were spun down and the pellets were resuspended in 100 µl of 0.25M Tris buffer, pH 7.5. The samples were subsequently freeze-thawed three-times and the cell debris was pelleted. The supernatant was used for CAT assays.

7.1.6. PASSAGING OF VIRUS FROM RNP-TRANSFECTED CELLS

MDCK cells were infected with helper virus and RNP-transfected 2 hours later as described above. After 1 hour cells and media were collected and cells were spun down. 100 µl of the supernatant media, containing virus, was added to 35 mm dishes with MDCK cells. After 12 hours these cells and media were collected and assayed for CAT activity. Virus contained in this supernatant media was used for subsequent rounds of infection of MDCK cells in 35 mm dishes.

7.1.7. CAT ASSAYS

CAT assays were done according to standard procedures, adapted from Gorman et al., 1982, Mol. Cell. Biol. 2: 1044–1051. The assays contained 10 μl of $^{14}C$ chloramphenicol (0.5 μCi; 8.3 nM; NEN), 20 μl of 40 mM acetyl CoA (Boehringer) and 50 μl of cell extracts in 0.25M Tris buffer (pH 7.5). Incubation times were 16–18 hours.

7.2. RESULTS rRNA templates were prepared from HgaI digested, end filled linearized pCATcNS using the bacteriophage T7 RNA polymerase as described in Section 6. The rRNA templates were combined with the viral RNA polymerase complex prepared as described in Section 6.1.1., and the resulting rRNPs were used to transfect MDCK and 293 cells lines which were superinfected with influenza A/WSN33. In each cell line transfected with the rRNPs, high levels of expression of CAT was obtained 6 hours post-infection. In addition, virus stocks obtained 24 hours post-infection synthesized high levels of CAT enzyme after subsequent passage in MDCK cells. The CAT-RNP was packaged into virus particles.

7.2.1. SYNTHESIS OF IVACAT1 TEMPLATE RNA

In order to study the transcription and replication signals of influenza A virus RNAs in vivo, we constructed plasmid pIVACAT1 (FIG. II) which directs the synthesis of an NS R/gA.-like transcript. This RNA shares the 22 5' terminal and the 26'3' terminal nucleotides with the NS RNA of influenza A/PR/8/34 virus and contain—instead of the coding sequences for the NS1 and NS2 proteins—those for a full-length CAT protein. For cloning purposes it also contains eight additional nucleotides including a BglII site between the stop codon of the CAT gene and the stretch of U's in the 5' noncoding region. The T7 promoter adjacent to the 5' noncoding sequences and the HgaI site downstream of the 3' end allow for the exact tailoring of the 5' and 3' ends. Run-off transcription using T7 polymerase generates a 716 nt long RNA: FIG. 12, lanes 2–4 show that this RNA is of discrete length and shorter than the 890 nt long marker NS RNA, which was synthesized by T7 transcription of pHgaNS (lane 1).

7.2.2. THE IVACAT1RNA IS TRANSCRIBED IN VITRO BY THE INFLUENZA A VIRUS RNA POLYMERASE

In the examples described in Section 6, it was demonstrated that synthetic RNAs containing at the 3' end the 15 3' terminal nucleotides of influenza virus RNA segment 8 can be transcribed in vitro using purified influenza A virus RNA polymerase. We tested whether unlabeled IVACAT1 RNA could be transcribed in a similar way. FIG. 12 lane 5 shows that the in vitro transcription reaction generated an RNA of discrete length and similar size to the product of the T7 transcription reaction suggesting synthesis of a full length product.

7.2.3. RNP-TRANSFECTION AND CAT ACTIVITY

Since the recombinant CAT RNA could be transcribed in vitro, a system was designed to test whether this RNA can be recognized and replicated in vivo (FIG. 13). Recombinant RNA was mixed with the purified polymerase to allow formation of viral RNP-like particles. To facilitate the association, the RNA/polymerase mixture was incubated in transcription buffer without nucleotides for 30 minutes at 30° C. prior to RNP-transfection. In some experiments, this preincubation step was omitted. RNP-transfections were either preceeded or followed by infection with influenza A/WSN/33 virus, since the production of viral polymerase protein was expected to be necessary for efficient amplification of the gene. The cells used were either MDCK cells, which are readily susceptible to influenza A/WSN/33 virus infection, or human 293 cells, which support infection at a slower rate.

In order to determine whether the minus sense IVACAT1 RNA could be amplified and transcribed in vivo, an experiment was performed in 293 cells. Cells were transfected with RNP, virus infected one hour later and harvested at various times post-infection. FIG. 14A shows that at early times post infection only background levels of CAT activity were detected (lanes 5,7 and 9). However, significant levels of CAT activity appeared seven hours after virus infection (lane 11). A similar level of CAT activity was detected two hours later (lane 13). There were background levels of CAT activity in the mock transfected cells at any time point (lanes 6, 8, 10, 12 and 14), and in control cells not infected with A/WSN/33 virus (lanes 1–4).

Preincubation of RNA and polymerase complex was not necessary for successful RNP-transfection. As can be seen in FIG. 14B, lanes 2 and 3, preincubation might actually cause a decrease in CAT activity, presumably due to RNA degradation during preincubation. In another control experiment, infection by helper virus of RNP-transfected cells was omitted (FIG. 14B, lanes 4 and 5). Since these lanes show no CAT activity we conclude that the IVACAT1 RNA is amplified specifically by the protein machinery supplied by the helper virus. In an additional control experiment, naked RNA was transfected into cells which were subsequently helper-infected or mock-infected. Again, no CAT activity was detected in these samples (FIG. 14B, lanes 6–9). Finally, virus-infected cells which were not transfected with recombinant CAT-RNP also did not exhibit endogenous acetylation activity (FIG. 14B, lane 10). It thus appears that addition of the purified polymerase to the recombinant RNA as well as infection of cells by helper virus is important for successful expression of the CAT enzyme.

Experiments were also performed using MDCK cells, the usual tissue culture host cell for influenza virus (FIG. 14C). When the reconstituted recombinant CAT-RNP complex was transfected 1 hour before virus infection, little CAT activity was observed at 7 hours post virus infection (FIG. 14C, lane 1). When RNP-transfection was accomplished 2 hours after virus infection, expression of CAT was greatly enhanced at 7 hours post-virus infection (FIG. 14C,/Lane 3). Therefore, MDCK cells are also viable host cells for these experiments.

7.2.4. THE CAT-RNF IS PACAKAGED INTO VIRUS PARTICLES

Since the recombinant CAT RNA can be replicated in vivo via helper virus functions, we examined whether virus produced in RNP-transfected and helper virus infected cells contained the CAT gene. MDCK cells were used in the experiment because they yield higher titers of infectious virus than 293 cells. MDCK cells were infected with A/WSN/33 virus, RNP-transfected 2 hours later and allowed to incubate overnight. At 14 hours post infection, media was harvested and cells were pelleted virus supernatant was then used to infect new MDCK cell monolayers. The inoculum was removed after 1 hour and cells were harvested at 12 hours post infection and assayed for CAT activity. FIG. 15 reveals that the virus preparation induces a level of CAT activity (lanes 2 and 3) which is significantly above control (lane 1). In this case, the addition of helper virus to the inoculum did not increase CAT activity (lane 4). Further passaging of supernatant virus on fresh MDCK cells did not result in measurable induction of CAT activity. This is not surprising as there is no selective pressure for retaining the CAT gene in these viral preparations. We excluded the possibility that we were transferring the original RNA/polymerase complex by pretreating the inocula with RNase. This treatment destroys viral RNPs of influenza virus (Pons et al. 1969 Virology 39: 250–259; Scholtissek and Becht, 1971 J. Gen. Virol. 10: 11–16).

8. RESCUE OF INFECTIOUS INFLUENZA VIRUSES USING RNA DERIVED FROM SPECIFIC RECOMBINANT DNAs

The experiments described in the subsections below demonstrate the rescue of infectious influenza viruses using RNA which is derived from specific recombinant DNAs. RNAs corresponding to the neuraminidase (NA) gene of influenza A/WSN/33 virus (WSN virus) were transcribed in vitro from appropriate plasmid DNAs and—following the addition of purified influenza virus polymerase complex (as described in Section 6.1.1. supra)—were transfected into MDBK cells as described in Section 7, Supra. Superinfection with helper virus, lacking the WSN NA gene, resulted in the release of viruses containing the WSN NA gene. Thus, this technology allows the engineering of infectious influenza viruses using cDNA clones and site-specific mutagenesis of their genomes. Furthermore, this technology may allow for the construction of infectious chimeric influenza viruses which can be used as efficient vectors for gene expression in tissue culture, animals or man.

The experiments described in Sections 6 and 7 supra, demonstrate that the 15 3' terminal nucleotides of negative strand influenza virus RNAs are sufficient to allow transcription in vitro using purified influenza virus polymerase proteins. In addition, the studies using the reporter gene chloramphenicol acetyltransferase (CAT) show that the 22 5' terminal and the 26 3' terminal nucleotides of the viral RNAs contain all the signals necessary for transcription, replication and packaging of influenza virus RNAs. As an extension of these results, a plasmid, pT3NAv, was constructed which contained the complete NA gene of influenza A/WSN/33 virus downstream of a truncated T3 promoter (FIG. 16). Therefore, runoff transcription of this plasmid, cut at the KsP632I site, yields an RNA which is identical to the true genomic NA gene of the WSN virus (FIG. 17, lane 3). This RNA was then incubated with purified polymerase (purified as described in Section 6.1.1) and used in a ribonucleoprotein (RNP) transfection experiment to allow the rescue of infectious virus using helper virus which did not contain the WSN virus NA. The choice of WSN-HK helper virus was based on the need for a strong selection system by which to isolate a rescued virus. Previously, it was shown that the WSN-HK virus can only form plaques in MDBK cells when protease is added to the medium. This is in marked contrast to WSN virus (isogenic to WSN-HK virus except for the neuraminidase gene), which in the absence of protease readily replicates in MDBK cells and forms large, easily visible plaques (Schulman et al., 1977, J. Virol. 24:170–176).

8.1. MATERIALS AND METHODS

8.1.1. VIRUSES AND CELLS

Influenza A/WSN/33 virus and A/WSN-HK virus were grown in Madin-Darby canine kidney (MDCK) cells and embryonated eggs, respectively (Sugiura et al., 1972, J. Virol. 10:639–647; Schulman et al., 1977, J. Virol. 24:170–176. Influenza A/PR/8/34 virus was also grown in embryonated eggs. Madin-Darby bovine kidney (MDBK) cells were used for the transfection experiments and for selection of rescued virus (Sugiura et al., 1972, J. Virol. 10:639–647).

8.1.2. CONSTRUCTION OF PLASMIDS

The pT3NAv, pT3NAv mut 1 and pT3NAv mut 2 plasmids were constructed by PCR-directed mutagenesis using a cloned copy of the WSN NA gene, which was obtained following standard procedures (Buonagurio et al., 1986, Science 232:980–982). To construct pT3NAv, the following primers were used: 5'-CGGAATTCTCTTCGAGCGAAAG-CAGGAGTT-3' and 5'-CCAAGCTTATTAACCCTCAC-TAAAAGTAGAAACAAGGAGTTT-3'. After 35 cycles in a thermal cycler (Coy Lab products, MI), the PCR product was digested with EcoRI and HindIII and cloned into pUC19. Plasmid pT3NAv mut 1 was constructed in a similar fashion except that the sequence of the primer was altered (FIG. 16). Plasmid pT3NAv mut 2 was constructed by cassette mutagenesis through the digestion of pT3NAv with PstI and NcoI and religation in the presence of the synthetic oligonucleotides-5'-CATGGGTGAGTTTCGAC-CAAAATCTAGATTATAAAATAGGATACATATGCA-3, and 5'-AATGTATCCTATTTTATAATCTA-GATTTTGGTCGAAACTCACC-3'. Oligonucleotides were synthesized on an applied Biosystems DNA synthesizer. The final clones pT3NAv, pT3NAv mut 1 and pT3NAv mut 2 were grown up and the DNAs were partially sequenced starting from the flanking pUC19 sequences and reaching into the coding sequences of the NA gene. The mutations in pT3NAv mut 2 were also confirmed by sequencing.

8.1.3. PURIFICATION OF INFLUENZA A VIRUS POLYMERASE AND RNP

TRANSFECTION IN MDBK CELLS

The RNA polymerase complex was purified from influenza A/PR/8/34 virus as described in Section 6.1.1, supra, and was then used for RNP transfection in MDBK cells using the protocol described in Section 7, supra, except that WSN-HK virus was used as helper virus at an moi of 1. RNAs used for RNP transfection were obtained by phenol extraction of purified virus or by transcription (using T3 polymerase) of pT3NAv, pT3NAv mut 1 and pT3NAv mut 2. All plasmids were digested with Ksp632I, end-filled by Klenow enzyme (BRL) and then transcribed in a runoff reaction as described in Section 7, supra.

8.2. RESULTS

8.2.1. RESCUE OF INFECTIOUS INFLUENZA VIRUS IN MDBK CELLS USING RNA

DERIVED FROM RECOMBINANT PLASMID DNA

A plasmid, pT3NAv, was constructed to contain the complete NA gene of influenza WSN virus downstream of a truncated T3 promoter (FIG. 16). Runoff transcription of the plasmid, cut at the Ksp632I site, yields an RNA which is identical in length to the true genomic NA gene of the WSN virus (FIG. 17, lane 3). This RNA was then incubated with purified polymerase and used in a ribonucleoprotein (RNP) transfection experiment to allow the rescue of infectious virus using helper virus. The choice of WSN-HK virus as helper virus was based on the need for a strong selection system by which to isolate a rescued virus. Previously, it was shown that the WSN-HN virus can only form plaques in MDBK cells when protease is added to the medium (Schulman et al., 1977, J. Virol. 24:170–176). This is in marked contrast to WSN virus (isogenic to WSN-HK helper virus except for the neuraminidase gene), which is the absence of protease readily replicates in MDBK cells and forms large, easily visible plaques (Sugiura et al., 1972, J. Virol. 10:639–647). MDBK cells were first infected with the WSN-HK helper virus and RNP-transfected one hour after virus infection. Following overnight incubation in the presence of 20 μg/ml plasminogen, supernatant from these cells was then amplified and plaqued in MDBK cells in the absence of protease in the medium. The appearance of plaques in MDBK cells (Schulman et al., 197, J. Virol. 10:639–647) indicated the presence of virus which contained the WSN virus NA gene, since supernatant from control experiments of cells infected only with the WSN-HK virus did not produce plaques. In a typical experiment involving the use of a 35 mm dish for the RNP-transfection, $2.5 \times 10^2$ plaques were observed.

In another control experiment, synthetic NA RNA was used which was derived from plasmid pT3NAv mut 1 (FIG. 16). This RNA differs from the wild type NA RNA derived from pT3NAv by a single nucleotide deletion in the non-translated region of the 5' end (FIG. 16). RNP-transfection of MDBK cells with this RNA and superinfection with WSN-HK virus did not result in the formation of rescued virus. This negative result is readily explained since we have shown in Sections 6 and 7, supra, that the essential sequences for the recognition of viral RNA by viral polymerases as well as the packaging signals are located within the 3' and 5' terminal sequences of the viral RNAs. However, we cannot exclude the possibility that rescue of virus using this mutated RNA does occur, albeit at an undetected frequency.

8.2.2. RNA ANALYSIS OF RESCUED VIRUS

Virus obtained in the rescue experiment was plaque purified, amplified in MDBK cells and RNA was extracted from this preparation. The RNA was then analyzed by electrophoresis on a polyacrylamide gel. FIG. 17 shows the RNA of the helper virus WSN-HK (lane 1) and the synthetic NA RNA (lane 3), which was transcribed by T3 polymerase from plasmid pT3NAv. The migration pattern of the RNAs of the rescued virus (lane 2) is identical to that of control WSN virus (lane 4). Also, the NA RNAs in lanes 2 and 4 migrate at the same position as the NA RNA derived from cDNA (lane 3) and faster than the HK virus NA band in the helper WSN-HK virus (lane 1). These experiments support the conclusion that as a result of the RNP-transfection, infectious virus was formed containing WSN virus NA RNA derived from cDNA.

8.2.3. RESCUE OF INFECTIOUS INFLUENZA VIRUS USING VIRION RNA

In another transfection experiment, RNA extracted from purified WSN virus was employed. When this naked RNA is transfected together with the polymerase proteins into helper virus infected cells, rescue of WSN virus capable of replicating in MDBK cells is observed. RNA isolated from an amplified plaque in this experiment is analyzed in lane 5 of FIG. 17 and shows a pattern indistinguishable from that of the control of WSN virus in lane 4.

8.2.4. INTRODUCTION OF SITE-SPECIFIC MUTATIONS INTO THE VIRAL GENOME

The experiments described so far involved the rescue of influenza WSN virus. Since the synthetic RNA used in these experiments is identical to the authentic WSN NA gene, the unlikely possibility of contamination by wild type WSN virus could not be rigorously ruled out. Therefore, we introduced five silent point mutations into the coding region of the NA gene in plasmid pT3NAv. These mutations were introduced by cassette mutagenesis through replacement of the short NcoI/PstI fragment present in the NA gene. The five mutations in the cDNA included a C to T change at position 901 and a C to A change at position 925, creating a new XbaI site and destroying the original pstI site, respectively. In addition, the entire serine codon at position 887–889 of the CDNA clone was replaced with an alternate serine triplet (FIG. 17). RMP-transfection of this mutagenized RNA (pT3NAv mut 2) and helper virus infection of MDBK cells again resulted in the rescue of a WSN-like virus which grew in MDBK cells in the absence of added protease. When the RNA of this virus was examined by sequence analysis, all five point mutations present in the plasmid DNA (FIG. 16) were observed in the viral RNA (FIG. 18). Since it is extremely unlikely that these mutations evolved in the wild type influenza WSN virus, we conclude that successful rescue of infectious influenza virus containing five site-specific mutations was achieved via RNP-transfection of engineered RNA.

9. EXAMPLE: SYNETHETIC REPLICATION SYSTEM

In the experiments described below, a cDNA clone which can produce an influenza virus-like vRNA molecule coding for a reporter gene was used. This resultant RNA is an NS-like vRNA which contains the antisense of the coding region of the chloramphenicol acetyltransferase gene (CAT) in place of the antisense coding regions for the nonstructural proteins, NS1 and NS2(section 7, supra). This recombinant RNA (IVACAT-1) was incubated with purified influenza virus RNP proteins and used in an attempt to develop a non-influenza virus dependent replication system. Mouse fibroblast C127 cells were infected with mixtures of recombinant vaccinia viruses (Smith et al., 1987, Virology, 160: 336–345) and transfected one hour later with the IVACAT-1 RNP. Mixtures of vectors expressing the three polymerases (PB2, PB1 and PA) and the nucleoprotein were used. Replication and transcription of the synthetic RNP was assayed by analyzing cells for CAT activity after overnight incubation. FIG. 19 examines the CAT activity present in cells initially infected with many of the possible mixtures of the 4 recombinant vaccinia viruses. FIG. 19, lane 4 is a positive control in which the influenza A/WSN/33 virus was used in lieu of the recombinant vaccinia viruses. CAT activity is present in this sample as well as in cells infected with all four vaccinia vectors (FIG. 19, lanes 8 and 10). Cells expressing any of the subsets of these four proteins did not produce detectable CAT protein (FIG. 19, lanes 5–7, 9, 11, unpublished). In addition, transfected RNA not incubated with the purified polymerase was also negative for CAT expression (section 7, supra). Thus, the presence of the PB2, PB1, PA and NP proteins are all that is necessary and sufficient for RNP expression and replication in this system. The levels of CAT activity obtained in vaccinia vector-infected cells are reproducibly higher than in cells infected with influenza as helper virus. The most probable explanation for this is that in influenza virus-infected cells, the CAT-RNP competes with the endogenous viral RNP's for active polymerase whereas in the vaccinia driven system that CAT-RNP is the only viral-like molecule present.

A number of other cell lines were then tested as hosts for this vaccinia virus driven system. FIG. 20A shows the results using MDBK, Hela, 293 and L cells. In each case, no CAT activity was observed when cells were infected with vectors that express only the 3 polymerase proteins but significant CAT activity was obtained if the additional vaccinia-vector inducing NP expression was also added.

Previously, a cell line (designated 3PNP-4) was constructed which constitutively expresses low levels of the PB2, PB1 and PA proteins and high levels of the NP protein. These cells can complement the growth of ts mutants mapping either to the PB2 or NP gene segments (Krystal et al., 1986, Proc Natl. Acad. Sci. U.S.A. 83: 2709–2713; Li et al., 1989, Virus Research 12: 97–112). Since replication through recombinant vaccinia virus vectors is dependent only on these proteins, it was conceivable that this cell line may be able to amplify and express the synthetic CAT-RNP in the absence of any virus infection. However, when this experiment was attempted, no detectable CAT activity was obtained. In order to investigate the reasons why this cell line did not support replication, mixtures of recombinant vaccinia viruses were used to infect 3PNP-4 cells. As we expected from the results described in Section 7, supra, the addition of the four polymerase proteins supported the expression of CAT (FIG. 20B, lane 2). FIG. 20B, lane 3 shows that the minimum mixture of vectors needed to induce CAT activity in 3PNP-4 cells are those expressing only the PB1 and PA proteins. Therefore, the steady state levels of PB2 and NP proteins in 3PNP-4 cells are sufficient but the levels of PB1 and PA are below threshold for CAT expression in the absence of helper virus. This correlates with the complementation phenotype exhibited by these cells, since only the growth of PB2 and NP mutants and not PB1 and PA mutants can be recovered at non-permissive temperature (Desselberger et al., 1980).

Since the synthetic IVACAT-1 RNA is of negative polarity, CAT can only be synthesized via transcription off the RNP molecule. Theoretically, detectable levels of CAT can be produced either through transcription off the transfected input RNP (equivalent to primary transcription) or first through amplification of RNP and subsequent transcription (necessitating RNP replication) or a combination of both. However, previous experiments described in Section 7, supra using influenza virus infection to drive the expression of the CAT protein showed that detectable expression occurred only if the input CAT-RNP was replicated (section 7, supra). This was shown by the use of a second CAT-RNA, IVACAT-2, which contains 3 mutations within the 12 bases at the 5' end of the viral RNA section 7, supra. This 12 base region is conserved among all eight gene segments in all influenza A viruses (Desselberger, at al., 1980, Gene 8: 315–328). This synthetic IVACAT-2 RNP is competent for transcription by the influenza virus polymerase but it is not replicated and when transfected into influenza virus-infected cells CAT activity remained undetected (section 7, supra). Therefore, primary transcription off the input RNA does not produce detectable levels of protein in influenza virus infected cells. Accordingly, we used this mutant RNA to examine whether the vaccinia vector-expressed influenza proteins induces CAT activity solely through primary transcription of input RNP or can allow for amplification through replication and subsequent transcription. C127 cells were infected with the recombinant vaccinia viruses and then transfected with either IVACAT-1 and IVACAT-2 generated RNPs. FIG. 20C shows that low levels of CAT activity can be detected in cells transfected with IVACAT-2 RNP (lane 2). When quantitated, 0.5–1% of the chloramphenical is converted to an acetylated form, compared to 0.2–0.4% in mock transfected lanes. However, much greater levels of activity are present in cells transfected with CAT-1 RNP (lane 1; routinely 15–50% conversion of chloramphenical), indicating that amplification is occurring in these cells. Therefore, this recombinant vaccinia virus-driven system is sequence-specific and the RNP's are undergoing replication.

In the experiments described, neither the NS1 nor NS2 proteins were required for RNP replication. Although their function is not known it has been speculated that these proteins may play a major role in replication because both proteins are synthesized in large amounts and are present in the nucleus section (Krug et al., 1989, The Influenza Viruses, Krug, R., Ed., Plenum Press, New York, 1989, pp. 89–152; Young et al., 1983, Proc. Natl. Acad. Sci. U.S.A. 80: 6105–6109; Greenspan et al., 1985, J. Virol. 54: 833–843; Lamb et al., 1984, Virology 135: 139–147). Based on the data presented, these proteins are not absolutely required for genome replication. It may be speculated that these proteins may actually have ancillary roles with regard to the replication of RNP, such as interaction with host factors, regulation of the expression of viral genes or some function involved with packaging of the RNP into infectious virions. However, it can not be ruled out that a function of these NS Proteins may be complemented by a vaccinia virus protein, although upon inspection, no obvious similarities were found between either the NS1 or NS2 proteins and known vaccinia virus proteins. The contrasting properties of these two viruses also argues against a complimenting vaccinia virus protein, as vaccinia is a large double-stranded DNA virus replicating exclusively in the cytoplasm while influenza virus is a negative sense RNA virus replicating exclusively in the nucleus. In addition, the replication of the synthetic PaPs occurred even in the presence of cytosine arabinoside (ara-C), an inhibitor of late gene expression in vaccinia virus (Oda et al., 1967, J. Mol. Biol. 27: 395–419; Kaverin et al., 1975, Virology, 65: 112–119; Cooper et al., 1979, Virology 96: 368–380).

This recombinant vaccinia vector dependent scheme possesses a number of advantages over the use of influenza virus infection to drive the replication of synthetic RNA. For one, since the expression of the viral proteins is completely artificial it will allow for a precise dissection of the processes involved in replication. Replication first involves the synthesis of positive sense template from the negative sense genomic RNA. This positive sense cRNA is then copied in order to amplify genomic sense RNP, which is then used for protein expression and packaging (Krung et al., 1989, supra). The system described herein demonstrate that only the influenza viral PB2, PB1, PA and NP proteins are required for the detection of expressed protein and for replication of RNP. Another advantage of this vaccinia vector driven replication scheme is that since the influenza polymerase proteins are expressed from cDNA integrated into the vaccinia virus, the mutagenesis of the polymerase proteins becomes a feasible and powerful method to further analyze structure-function relationships of the vital polymerase proteins. Also, we are currently attempting to rescue infectious influenza virus through the transfection of mixtures of reconstituted vital RNPs. This technique, if successful, should allow for the easy construction of defined recombinant viruses through the addition of defined RNPs, either naturally or synthetically derived. This technology should also be applicable for the analysis and dissection of the replication apparatus of other negative strand viruses.

10. DEPOSIT OF MICROORGANISMS

An *E. coli* cell line containing the plasmid pIVACAT is being deposited with the Agricultural Research Culture Collection (NRRL), Peoria, IL; and has the following accession number

| Strain | Plasmid | Accession Number |
|---|---|---|
| E. coli (DH5a) | pIVACAT | NRRL |

The present invention is not to be limited in scope by the specific embodiments described which are intended as single illustrations of individual aspects of the invention, and any constructs, viruses or enzymes which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

What is claimed is:

1. A method for engineering a recombinant negative-strand RNA virus, comprising:
   (a) transcribing a DNA molecule encoding a mutagenized gene of the negative-strand RNA virus operatively linked to the complement of the viral RNA-directed RNA polymerase binding site, to form a recombinant RNA molecule comprising the mutated viral gene operatively linked to the viral polymerase binding site, and combining the recombinant RNA molecule with the viral RNA-directed RNA polymerase to form a recombinant RNP;
   (b) culturing a host cell transfected with the recombinant RNP and infected with a parental strain of the negative strand virus; and
   (c) recovering chimeric viruses containing the mutated viral gene from the culture.

2. The method of claim 1 wherein the viral gene was mutagenized by site-directed mutagenesis.

3. A method for engineering a recombinant influenza virus, comprising:
   (a) transcribing a DNA molecule encoding a mutagenized gene of the influenza virus operatively linked to the complement of the viral RNA-directed RNA polymerase binding site, to form a recombinant RNA molecule comprising the mutated influenza gene operatively linked to the viral polymerase binding site, and combining the recombinant RNA molecule with the viral RNA-directed RNA polymerase to form the recombinant RNP;
   (b) culturing a host cell transfected with the recombinant RNP and infected with a parental strain of the influenza virus; and
   (c) recovering chimeric influenza viruses containing the mutated viral gene from the culture.

4. The method of claim 3 wherein the influenza gene was mutagenized by site-directed mutagenesis.

5. The method of claim 34 wherein the mutated influenza gene is the NA gene of the influenza genome.

6. The method of claim 3 wherein the mutated influenza gene is the NS gene of the influenza genome.

7. The method of claim 3 wherein the mutated influenza gene is the HA gene of the influenza genome.

8. The method of claim 3 wherein the mutated influenza gene is the PB1 gene or the PB2 gene of the influenza genome.

9. The method of claim 3 wherein the mutated influenza gene is the PA gene of the influenza genome.

10. The method of claim 3 wherein the mutated influenza gene is the M gene of the influenza genome.

11. The method of claim 3 wherein the mutated influenza gene is the NP gene of the influenza genome.

\* \* \* \* \*